(12) United States Patent
Ogawa et al.

(10) Patent No.: US 8,022,061 B2
(45) Date of Patent: Sep. 20, 2011

(54) N-ARYL PYRAZOLE COMPOUNDS, COMPOSITIONS, AND METHODS FOR THEIR USE

(75) Inventors: Yasuyuki Ogawa, Tokyo (JP); Ryo Okuyama, Tokyo (JP); Satoshi Shibuya, Tokyo (JP); Narihiro Toda, Tokyo (JP); Zhaodan Cao, Brisbane, CA (US); Zice Fu, Foster City, CA (US); Xiaolin Hao, Foster City, CA (US); Yong-Jae Kim, Foster City, CA (US); Leping Li, Burlingame, CA (US); Sarah E. Lively, San Carlos, CA (US); Mike Lizarzaburu, San Diego, CA (US); Hui Tian, Foster City, CA (US); Ming Yu, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 972 days.

(21) Appl. No.: 11/973,900

(22) Filed: Oct. 9, 2007

(65) Prior Publication Data

US 2008/0153778 A1    Jun. 26, 2008

Related U.S. Application Data

(60) Provisional application No. 60/851,083, filed on Oct. 10, 2006.

(51) Int. Cl.
*C07D 403/04* (2006.01)
*C07D 417/14* (2006.01)
*A61K 31/506* (2006.01)

(52) U.S. Cl. ........... 514/214.02; 514/221; 514/235.8; 514/275; 540/568; 540/578; 544/122; 544/331

(58) Field of Classification Search ......... 540/568, 540/578; 544/122, 331; 514/214.02, 221, 514/235.8, 275
See application file for complete search history.

(56) References Cited

U.S. PATENT DOCUMENTS

| | | | |
|---|---|---|---|
| 3,723,433 | A | 3/1973 | Ueno et al. |
| 6,051,574 | A | 4/2000 | Anthony |
| 6,169,086 | B1 | 1/2001 | Ejima et al. |
| 6,818,631 | B1 | 11/2004 | Nakagawa et al. |
| 7,223,782 | B2 | 5/2007 | Atkinson et al. |
| 7,282,469 | B2 | 10/2007 | Hoffman et al. |
| 2004/0198758 | A1 | 10/2004 | Rapado et al. |
| 2009/0275586 | A1* | 11/2009 | Govek et al. ............ 514/249 |

FOREIGN PATENT DOCUMENTS

| | | |
|---|---|---|
| EP | 0784055 A1 | 7/1997 |
| EP | 1329160 A2 | 7/2003 |
| JP | 2004-145081 | 5/1992 |
| JP | 2004-339080 | 12/2004 |
| WO | WO 98/24782 | 6/1998 |
| WO | WO 98/40379 | 9/1998 |
| WO | WO 01/87849 A2 | 11/2001 |
| WO | WO 2004/099156 A1 | 11/2004 |
| WO | WO 2005/058883 A1 | 6/2005 |
| WO | WO 2005/110994 A2 | 11/2005 |
| WO | WO 2007/008541 A1 | 1/2007 |

OTHER PUBLICATIONS

Sekiguchi et al., CAPLUS Abstract No. 138:321285 (2003).*
Simone, Oncology: Introduction, Cecil Textbook of Medicine, 20th Edition, vol. 1, pp. 1004-1010, 1996.*
Damasio, Alzheimer's Disease and Related Dementias, Cecil Textbook of Medicine, 20th Edition, vol. 2, pp. 1992-6, 1996.*
Layzer, Degenerative System Disorders of the Nervous System, Cecil Textbook of Medicine, 20th Edition, vol. 2, 2050-7, 1996.*
PCT/US2007/021678—PCT International Search Report, mailed, Feb. 26, 2008.
Naito et al., "Synthesis and Antitumor Activity of Novel Pyrimidinyl Pyrazole Derivatives," *Chem. Pharm Bull.*, 1999, vol. 47:1679-1684.
Ohki et al., "Synthesis and Mechanism of Action of Novel Pyrimidinyl Pyrazole Derivatives Possessing Antiproliferative Activity," *Bioorganic & Medicinal Chemistry Letters*, 2002, vol. 12:3191-3193.
Shirakawa et al., "Pyrimidine Derivatives, XI. 2-(1-Pyrazolyl)pyrimidines," *Takeda Kenkyusho Nempo*, 1964, vol. 22:19-22, as reported in *Chemical Abstracts*, 1964, vol. 60(10), col. 12009-12012 (abstract only attached).
Zhang et al., "Fluorous Synthesis of Disubstituted Pyrimidines," *Organic Letters* 2003, vol. 5:1011-1013.

* cited by examiner

*Primary Examiner* — Deepak Rao
(74) *Attorney, Agent, or Firm* — Jones Day

(57) ABSTRACT

Compounds having formula I:

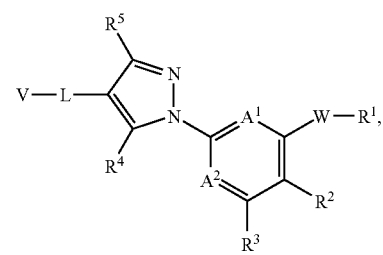

Figure 1:
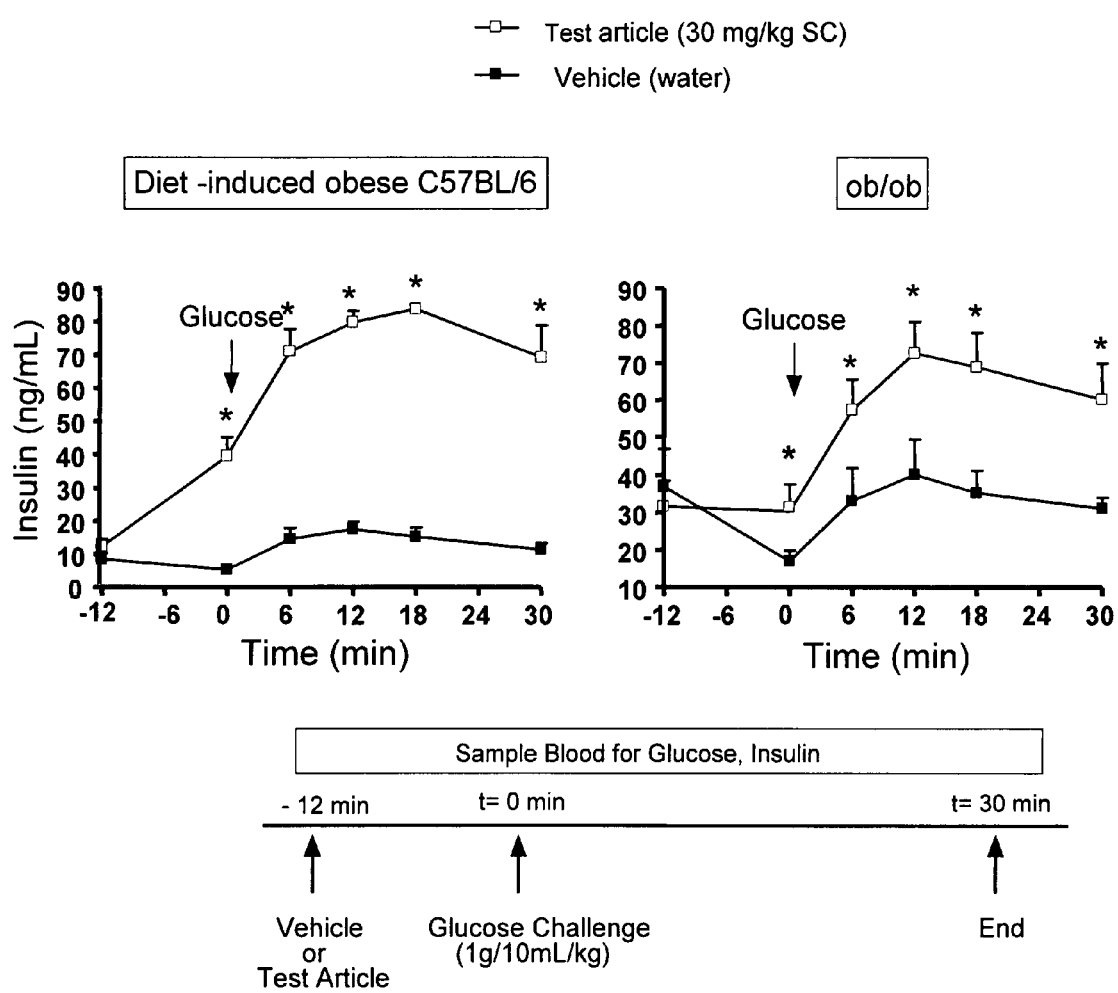

where $A^1$, $A^2$, L, V, W, $R^1$, $R^2$, $R^3$, $R^4$ and $R^5$ are as described herein, compositions thereof, and their use for the treatment or prevention of type 2 diabetes and type 2 diabetes-related conditions are provided herein.

15 Claims, 2 Drawing Sheets

Insulin secretion data

N-ARYL PYRAZOLE COMPOUNDS, COMPOSITIONS, AND METHODS FOR THEIR USE

1. CROSS-REFERENCE TO RELATED APPLICATIONS

This application claims the benefit of U.S. Provisional Application No. 60/851,083, filed Oct. 10, 2006, the contents of which are incorporated herein by references in its entirety for all purposes.

2. FIELD OF THE INVENTION

The present invention is directed to compounds, compositions and methods useful for treating insulin related diseases and conditions associated with insufficient insulin production, including diabetes and especially type 2 diabetes and type 2 diabetes-related conditions or symptoms thereof.

3. BACKGROUND OF THE INVENTION

Type 2 diabetes is the most common form of diabetes, a condition in which the amount of glucose in the blood of a subject is not regulated properly. Diabetes can result when the body no longer responds adequately to insulin or when the production of insulin is inadequate. An estimated 135 million people worldwide are affected by type 2 diabetes. The number of Americans diagnosed with type 2 diabetes is estimated to range between 11.6 million to 14 million people. Although onset of type 2 diabetes is primarily observed in people over 40 years of age, the typical age at diagnosis of type 2 diabetes has decreased over the last decades as increasing numbers of youths and young adults have been affected. See Koopman et al. (2005) *Ann. Fam. Med.* 3:60-63.

Contributing factors to the rising incidence of type 2 diabetes include obesity and increasingly sedentary lifestyles. It is also recognized that insulin secretagogue therapy is appropriate for type 2 diabetes management when diet and lifestyle modifications fail. Typically, secretagogue therapy is intended to augment circulating insulin levels in patients with a moderate degree of β-cell dysfunction. Sulfonylureas, which stimulate insulin secretion and reduce hyperglycemia, have been used as insulin secretagogues when administered to patients with type 2 diabetes. Nevertheless, the long plasma half-life and the long-lasting effect of some sulfonylureas increase the risk of hypoglycemia, and new candidate insulin secretagogues are sought.

Therapies for treating type 2 diabetes and type 2 diabetes-related conditions or symptoms are sought because the prevalence of type 2 diabetes is increasing. Novel compounds that display desirable activity for treating type 2 diabetes and type 2 diabetes-related conditions or symptoms are described herein.

4. SUMMARY OF THE INVENTION

Provided herein are compounds, pharmaceutical compositions and methods useful for treating or preventing a disease or condition associated with insufficient insulin production, in particular, type 2 diabetes and type 2 diabetes-related diseases or conditions including diabetic ketoacidosis, hyperglycemia and diabetic neuropathy and related conditions or disorders such as obesity and metabolic syndromes; a disease or condition associated with inflammation, such as, for example, asthma, psoriasis, arthritis, rheumatoid arthritis, and inflammatory bowel disease; a disease or condition including cancer and neurologic disorder; or a symptom of any of the foregoing diseases or conditions.

In one aspect, the invention provides compounds of formula I:

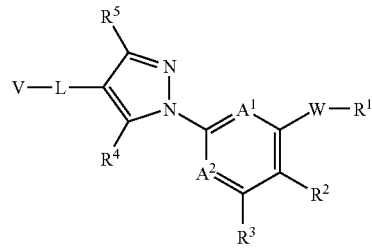

I wherein
$A^1$ and $A^2$ are each independently N or C(H);
L is a divalent linkage selected from the group consisting of a single bond, $(C_1-C_5)$alkylene, $(C_2-C_5)$alkenylene, $-(CH_2)_n-O-(CH_2)_p-$, $-(CH_2)_n-N(R^6)-(CH_2)_p-$, $-(CH_2)_n-CH(NR^6R^7)-(CH_2)_p-$, $-(CH_2)_n-CH(OR^6)-(CH_2)_p-$, $-(CH_2)_n-S(O)_kN(R^7)-(CH_2)_p-$, $-(CH_2)_n-C(O)N(R^7)-(CH_2)_p-$, $-(CH_2)_n-C(O)N(R^7)C(R^8)H-(CH_2)_p-$, $-(CH_2)_n-N(R^7)C(O)N(R^8)-(CH_2)_p-$, $-(CH_2)_n-C(O)-(CH_2)_p-$, $-(CH_2)_n-C(=NOR^6)-(CH_2)_p-$, $-(CH_2)_n-C(O)O-(CH_2)_p-$, $-(CH_2)_n-N(R^7)S(O)_kN(R^8)-(CH_2)_p-$, and $-(CH_2)_n-N(R^7)CO_2-(CH_2)_p-$, wherein each subscript n and subscript p is independently 0, 1, 2 or 3;
V is hydroxy, $(C_1-C_6)$alkoxy, cyclo$(C_3-C_7)$alkyl, heterocyclo$(C_3-C_7)$alkyl, aryl, heteroaryl, aryl$(C_1-C_4)$alkyl, or heteroaryl$(C_1-C_4)$alkyl;
W is a single bond, $(C_1-C_5)$alkylene, $(C_2-C_5)$alkenylene, $-O-$, $-S(O)_k-$, $-C(O)$, $-NR^6-$ or $-CH_2NR^6-$;
$R^1$ is $(C_1-C_6)$alkyl, $(C_1-C_6)$alkenyl, hetero$(C_2-C_6)$alkyl, cyclo$(C_3-C_7)$alkyl, heterocyclo$(C_3-C_7)$alkyl, aryl, heteroaryl, aryl$(C_1-C_4)$alkyl or heteroaryl$(C_1-C_4)$alkyl;
$R^2$ is hydrogen, hydroxyl, halogen, $(C_1-C_6)$alkyl, $-CN$, halo$(C_1-C_6)$alkyl, $(C_1-C_6)$alkoxy, halo$(C_1-C_6)$alkoxy or $(C_2-C_6)$alkenyl;
each $R^3$ and $R^5$ is independently hydrogen, hydroxy, halogen, $-CN$, $(C_1-C_6)$alkyl, halo$(C_1-C_6)$alkyl, $(C_1-C_6)$alkyloxy, or halo$(C_1-C_6)$alkoxy;
$R^4$ is $(C_1-C_8)$alkyl, hetero$(C_2-C_8)$alkyl, cyclo$(C_3-C_7)$alkyl, aryl, heteroaryl, aryl$(C_1-C_4)$alkyl, or heteroaryl$(C_1-C_4)$alkyl;
$R^6$ is hydrogen, $(C_1-C_8)$alkyl, fluoro$(C_1-C_4)$alkyl, hetero$(C_2-C_8)$alkyl, aryl, heteroaryl, aryl$(C_1-C_4)$alkyl, $-C(O)R'$, $-CO_2R'$, $-C(O)NR'R''$, $-S(O)_kR'$ or $-S(O)_kNR'R''$;
each $R^7$ and $R^8$ is independently selected from hydrogen, $(C_1-C_8)$alkyl, fluoro$(C_1-C_4)$alkyl, hetero$(C_2-C_8)$alkyl, aryl, heteroaryl, and aryl$(C_1-C_4)$alkyl;
each R' and R" is independently hydrogen, $(C_1-C_6)$alkyl, cyclo$(C_3-C_8)$alkyl, aryl or aryl$(C_1-C_4)$alkyl; and
each subscript k is independently 0, 1 or 2.

In certain embodiments, further provided herein are compounds of formula II:

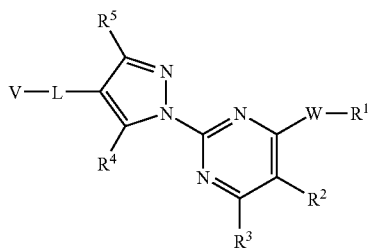

II wherein L, V, W, $R^1$, $R^2$, $R^3$, $R^4$ and $R^5$ are as defined above with regard to formula I.

In certain embodiments, provided herein are compounds of formula III:

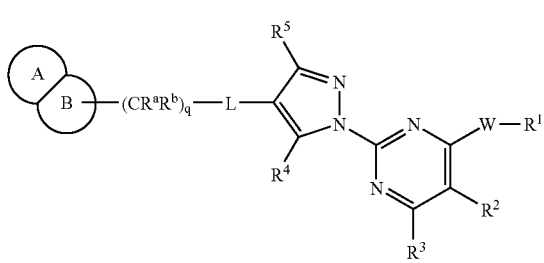

wherein L, W, R$^1$, R$^2$, R$^3$, R$^4$ and R$^5$ are as defined above with regard to formula I, and
each R$^a$ and R$^b$ is independently selected from the group consisting of hydrogen, (C$_1$-C$_5$)alkyl, cyclo(C$_3$-C$_5$)alkyl, halo(C$_1$-C$_5$)alkyl, aryl, heteroaryl, and aryl(C$_1$-C$_4$)alkyl;
subscript q is 0, 1, 2 or 3; and
structure

is a fused ring structure wherein ring A is a 5- or 6-membered ring containing 0, 1, 2 or 3 heteroatoms selected from O, S and N, and ring B is a 5-, 6-, 7- or 8-membered ring containing 0, 1, 2, 3 or 4 heteroatoms selected from O, S and N.

In some embodiments, the compounds provided have formula IV or V:

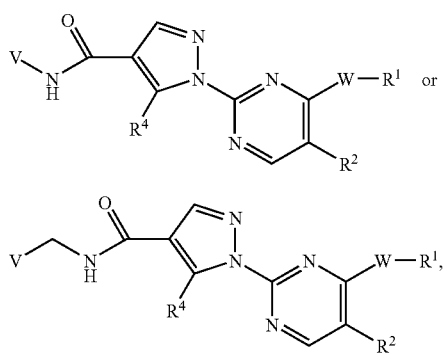

where V, W, R$^1$, R$^2$ and R$^4$ are as defined above with regard to formula I.

In some embodiments, the compounds provided have formula VI:

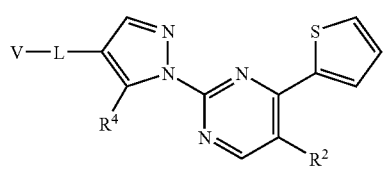

where V, L, R$^2$ and R$^4$ are as defined above with regard to formula I.

In certain embodiments, the compounds provided have formula VII:

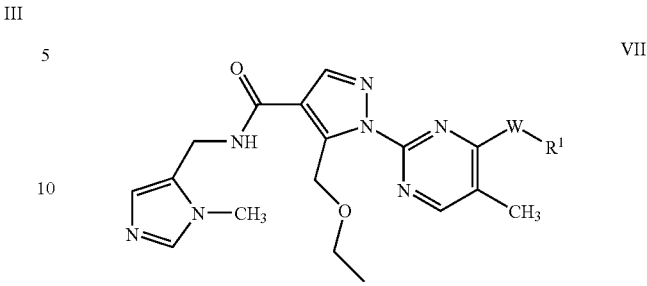

where W and R$^1$ are as defined above with regard to formula I.

Unless otherwise indicated, the compounds provided in the formulas provided herein are meant to include pharmaceutically acceptable salts, solvates and prodrugs thereof.

In another aspect, pharmaceutical compositions are provided herein comprising a compound of formula I-VII and a pharmaceutically acceptable carrier, excipient or diluent.

In one aspect, methods are provided for treating or preventing a disease or condition in a mammal in need thereof, comprising administering a therapeutically effective amount of a compound of any one of formula I-VII to the mammal. Diseases and conditions that can be treated or prevented include, for example, type 2 diabetes, diabetic ketoacidosis, hyperglycemia, diabetic neuropathy, obesity, metabolic syndrome, inflammation, inflammatory disorders including asthma, psoriasis, arthritis, rheumatoid arthritis, and inflammatory bowel disease, cancer, neurologic disorder, or a symptom thereof. The methods include the treatment of a human.

In one aspect, methods are provided for modulating insulin concentration in plasma of a mammal, comprising administering an amount of a compound of any one of formula I-VII effective to modulate insulin concentration in plasma.

In one aspect, methods are provided for increasing insulin concentration in plasma of a mammal, comprising administering an amount of a compound of any one of formula I-VII effective to increase insulin concentration in plasma.

In another aspect, methods are provided for modulating secretion, for example, secretion of insulin, by a pancreatic β-cell, in vitro or in vivo, comprising contacting the pancreatic β-cell with an amount of a compound of any one of formula I-VII effective to modulate the pancreatic islet cell secretion under conditions wherein the pancreatic β-cell secretion is modulated.

In yet another aspect, a use of a compound of any one of formula I-VII for use in treating a disease or condition, or for manufacture of a medicament for treating a disease or condition are provided, wherein the disease or condition are selected from type 2 diabetes, diabetic ketoacidosis, hyperglycemia, diabetic neuropathy, obesity, metabolic syndrome, inflammation, inflammatory disorders including asthma, psoriasis, arthritis, rheumatoid arthritis, and inflammatory bowel disease, cancer, and neurologic disorder, or a symptom thereof.

Other objects, features and advantages of the invention will become apparent to those skilled in the art from the following description and claims.

5. BRIEF DESCRIPTION OF THE FIGURES

FIG. 1 provides results from glucose-challenged animal models of diabetes demonstrating the increases in circulating insulin levels in animals treated with an exemplary compound relative to control animals.

Figure 2:
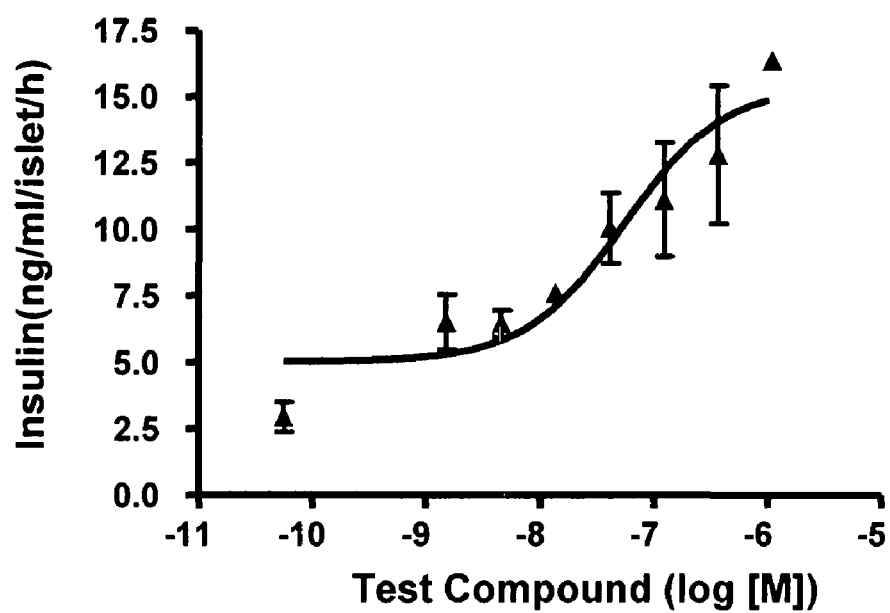

FIG. 2 provides concentrations of insulin secreted from islet pancreatic cells in response to an exemplary compound.

6. DETAILED DESCRIPTION

6.1. Definitions

The terms "modulate," "modulation," and the like, refer to the ability of a compound to increase or decrease the function of a cell, e.g., a pancreatic β-cell or a cell made using recombinant technology, leading to increased concentrations of insulin produced and/or secreted by a cell, where such function may include transcription regulatory activity, exocytosis, cell membrane excitability and/or protein binding. Modulation may occur in vitro or in vivo.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "therapeutically effective amount" refers to the amount of the subject compound that will elicit the biological or medical response of a cell, tissue, organ, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the disease or condition being treated, or to alleviate or ameliorate the disease or cause thereof. The therapeutically effective amount will vary depending on the compound, the disease and its severity and the age, weight, etc., of the mammal to be treated.

The terms "treat", "treating" and "treatment", as used herein, are meant to include alleviating or abrogating a disease and/or its attendant symptoms and/or alleviating or eradicating the cause of the disease itself.

The term "alkyl," by itself or as part of another substituent, means, unless otherwise stated, a straight or branched chain hydrocarbon radical, or combination thereof, which is fully saturated, having the number of carbon atoms designated (i.e., $C_1$-$C_8$ means one to eight carbons). Examples of alkyl groups include methyl, ethyl, n-propyl, isopropyl, n-butyl, t-butyl, isobutyl, sec-butyl, homologs and isomers of, for example, n-pentyl, n-hexyl, n-heptyl, n-octyl and the like.

The term "alkenyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1, 4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl and higher homologs and isomers thereof.

Straight or branched alkyl, alkenyl and alkynyl groups are each specifically contemplated.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain hydrocarbon radical, or combinations thereof, consisting of the stated number of carbon atoms and from one to three heteroatoms selected from O, N, Si and S, and wherein the nitrogen and sulfur atoms may optionally be oxidized and the nitrogen heteroatom may optionally be quaternized. The heteroatom(s) N and S may be placed at any interior position of the heteroalkyl group. The heteroatom(s) O and Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —O—$CH_2$—$CH_3$, —$CH_2$—$CH_2$—, —S(O)—$CH_3$, —$CH_2$—$CH_2$—S(O)$_2$—$CH_3$, —Si($CH_3$)$_3$, and —$CH_2$—CH=N—$OCH_3$. As such, it will be understood that "heteroalkyl" includes, for example, alkoxy and alkoxyalkyl groups such as ($C_2$-$C_8$)alkoxy and ($C_2$-$C_8$)alkoxyalkyl. Up to two heteroatoms in an "heteroalkyl" may be consecutive, such as, for example, —$CH_2$—NH—$OCH_3$ and —$CH_2$—O—Si($CH_3$)$_3$. When a prefix such as ($C_2$-$C_8$) is used to refer to a heteroalkyl group, the number of carbons (2-8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Thus, the terms "cycloalkyl" and "heterocycloalkyl" are meant to be included in the terms "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, purinyl, 2-benzimidazolyl, 5-indolyl, 1H-indazole, carbazole, α-carboline, β-carboline, γ-carboline, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl or quinolyl group which is unsubstituted or substituted.

In certain embodiments, the term "heteroaryl" includes a partially saturated heteroaryl. As used herein, the phrase "partially saturated heteroaryl" refers to a fused ring structure comprised of at least one polyunsaturated ring structure and at least one nonaromatic, polysaturated ring wherein the fused ring structure contains from one to four heteroatoms selected from the group consisting of N, O and S, wherein the nitrogen and sulfur atoms are optionally oxidized, and wherein the one to four heteroatoms can be located in a polyunsaturated ring, in a nonaromatic, polysaturated ring, or in both a polyunsaturated ring and a nonaromatic, polysaturated ring. It will be understood that the nonaromatic, polysaturated ring can have one or more unsaturated bonds within it. Non-limiting examples of partially saturated heteroaryls include: 5,6,7,8-tetrahydroisoquinoline; 1,2,3,4-tetrahydroisoquinoline; 6,7,8,9-tetrahydro-5H-[1,2,4]triazolo[4,3-a]azepine; 5,6,7,8-tetrahydro-[1,2,4]triazolo[4,3-a]pyrazine; 4,5,6,7-tetrahydro-1H-benzo[d]imidazole; 4,5,6,7-tetrahydroisoxazolo[4,5-c]pyridine; 5,6,7,8-tetrahydroimidazo[1,2-a]pyridine; 5,6,7,8-tetrahydroimidazo[1,5-a]pyridine; 6,7,8,9-tetrahydro-5H-imidazo[1,5-a][1,4]diazepine, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR"R'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R'", —CN and —NO$_2$, in a number ranging from zero to three, with those groups having zero, one or two substituents being particularly preferred. R', R" and R'" each independently refer to hydrogen, unsubstituted ($C_1$-$C_8$)alkyl and heteroalkyl, unsubstituted aryl, aryl substituted with one to three halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR'-halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R', R" and R'" are as defined above. Further preferred substituents are selected from: —OR', =O, —NR'R", -halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR"R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Otherwise, R' is as defined above.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

6.2. Embodiments

Provided herein are compounds that have utility as modulators of insulin levels. As such, the compounds find use as therapeutic agents for the treatment or prevention of type 2 diabetes and related conditions or symptoms thereof including diabetic ketoacidosis, hyperglycemia, diabetic neuropathy, obesity and metabolic syndrome. In certain embodiments, the compounds provided herein can be used as therapeutic agents for the treatment or prevention of a disease or condition associated with inflammation, such as, for example, asthma, psoriasis, arthritis, rheumatoid arthritis, and inflammatory bowel disease; a disease or condition including cancer and neurologic disorder; or a symptom of any of the foregoing diseases or conditions.

Compounds contemplated by the invention include, but are not limited to, the exemplary compounds provided herein.

6.2.1. Compounds

In one aspect, the invention provides compounds of formula I:

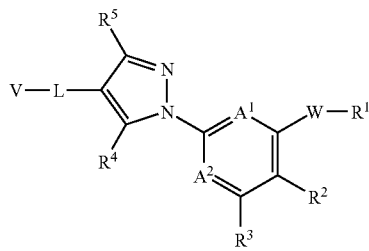

wherein $A^1$, $A^2$, L, V, W, $R^1$, $R^2$, $R^3$, $R^4$ and $R^5$ are as defined below.

In formula I, $A^1$ and $A^2$ are each independently N or C(H).

In certain embodiments, $A^1$ is N and $A^2$ is C(H). In some embodiments, $A^1$ is C(H) and $A^2$ is N. In certain embodiments, at least one of $A^1$ and $A^2$ is C(H).

L is a divalent linkage selected from the group consisting of a single bond, $(C_1$-$C_5)$alkylene, $(C_2$-$C_5)$alkenylene, —$(CH_2)_n$—O—$(CH_2)_p$—, —$(CH_2)_n$—N($R^6$)—$(CH_2)_p$—, —$(CH_2)_n$—CH($NR^6R^7$)—$(CH_2)_p$—, —$(CH_2)_n$—CH($OR^6$)—$(CH_2)_p$—, —$(CH_2)_n$—S(O)$_k$N($R^7$)—$(CH_2)_p$—, —$(CH_2)_n$—C(O)N($R^7$)—$(CH_2)_p$—, —$(CH_2)_n$—C(O)N($R^7$)C($R^8$)H—$(CH_2)_p$—, —$(CH_2)_n$—N($R^7$)C(O)N($R^8$)—$(CH_2)_p$—, —$(CH_2)_n$—C(O)—$(CH_2)_p$—, —$(CH_2)_n$—C(=NOR$^6$)—$(CH_2)_p$—, —$(CH_2)_n$—C(O)O—$(CH_2)_p$—, —$(CH_2)_n$—N($R^7$)S(O)$_k$N($R^8$)—$(CH_2)_p$—, and —$(CH_2)_n$—N($R^7$)CO$_2$—$(CH_2)_p$—, wherein each subscript n and subscript p is independently 0, 1, 2 or 3. Exemplary L groups are —$CH_2CH_2$—, —CH=CHCH$_2$—, —$CH_2$—O—$CH_2$—, —NHCH$_2$—, —C(O)NH—, —$CH_2C(CH_3)_2CH_2$—, —C(O)NHCH$_2$—, —NHC(O)NH— and —NHCO$_2$—.

Those of skill will understand that the orientation of L, when linked to V and the pyrazole core of formula I, can be in either direction. For example, when L is —$(CH_2)_n$—C(O)N($R^7$)—$(CH_2)_p$—, subscript n is 1 and subscript p is 0, then L can be attached to its adjacent moieties in either orientation as shown:

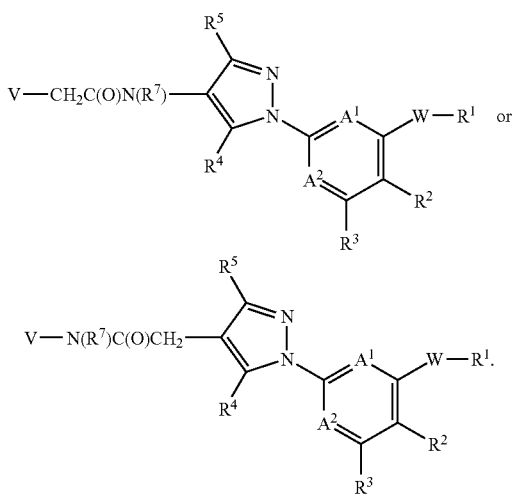

V is hydroxy, $(C_1$-$C_6)$alkoxy, cyclo$(C_3$-$C_7)$alkyl, heterocyclo$(C_3$-$C_7)$alkyl, aryl, heteroaryl, aryl$(C_1$-$C_4)$alkyl, or heteroaryl$(C_1$-$C_4)$alkyl. In certain embodiments, V is cyclo$(C_3$-$C_7)$alkyl, heterocyclo$(C_3$-$C_7)$alkyl, aryl, heteroaryl, aryl$(C_1$-$C_4)$alkyl, or heteroaryl$(C_1$-$C_4)$alkyl.

In certain embodiments, V is a monocyclic ring group. In some embodiments, V is a fused bicyclic ring group. In some embodiments, V is a partially saturated heteroaryl.

In certain embodiments, V comprises a substituted or unsubstituted 5- or 6-membered ring structure containing 0, 1, 2, 3 or 4 heteroatoms selected from O, S or N. In some embodiments, V comprises an aromatic ring. In other embodiments, V comprises a non-aromatic ring. One or more substituents can be attached to the 5- or 6-membered ring structure of the V group including, for example, $(C_1$-$C_8)$alkyl, halo$(C_1$-$C_4)$alkyl, halo, cyclo$(C_3$-$C_7)$alkyl, hetero$(C_2$-$C_8)$alkyl, aryl, heteroaryl, aryl$(C_1$-$C_4)$alkyl, hydroxyl, =O, —CN, —C(O)R', —CO$_2$R', —C(O)NR'R'', —NR'R'', —S(O)$_k$R' or —S(O)$_k$NR'R''. Exemplary V groups include the following, where the dotted line represents a bond attaching the exemplary V group to L, or to the pyrazole core where L is a single bond, as depicted in formula I:

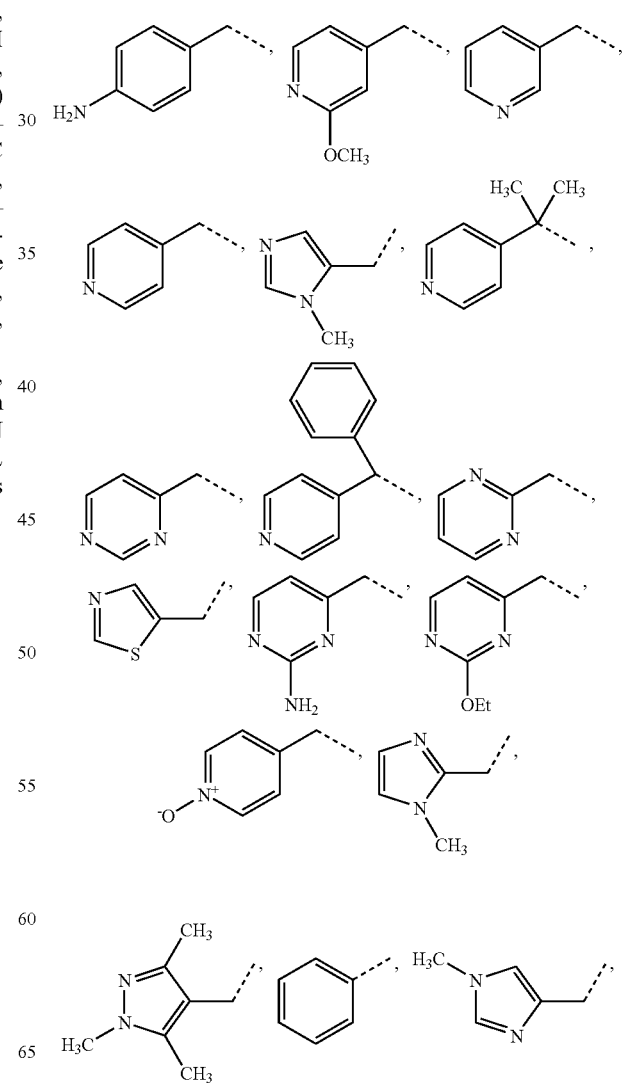

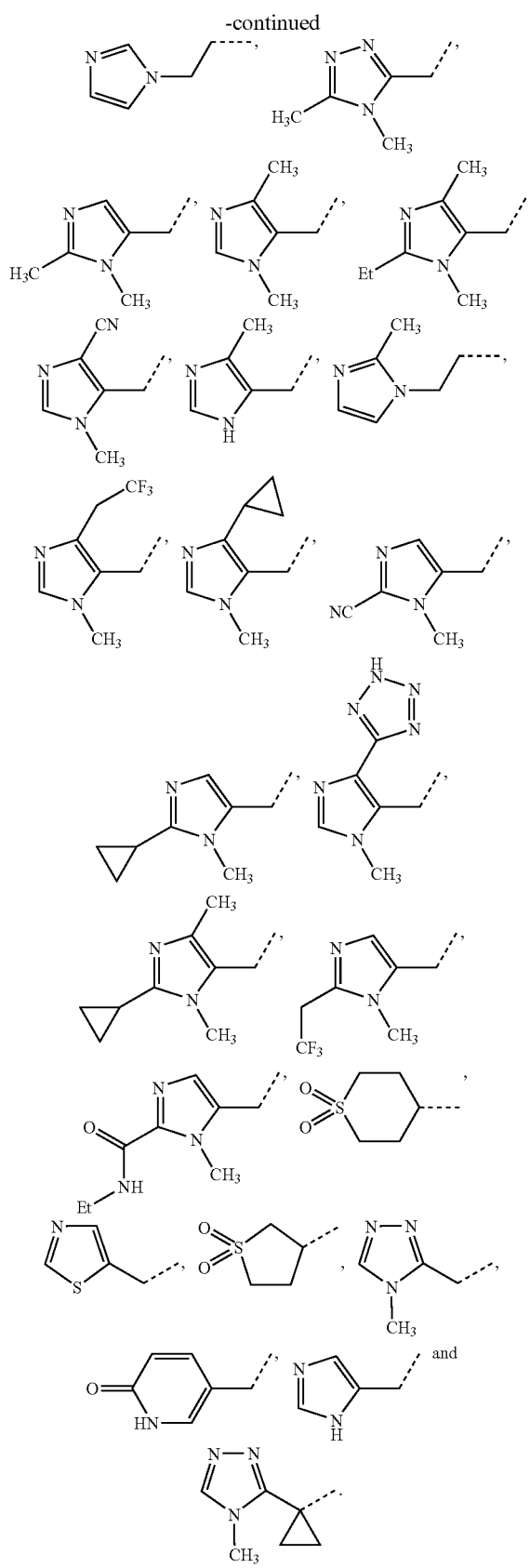

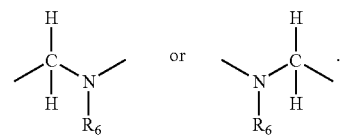

In formula I, W is a single bond, $(C_1-C_5)$alkylene, $(C_2-C_5)$ alkenylene, —O—, —S(O)$_k$—, —C(O), —NR$^6$— or —CH$_2$NR$^6$—. Exemplary W groups other than a single bond include methylene, ethylene, propylene, —S(O)$_2$—, —N(CH$_3$)— and —NH—.

Those of skill will understand that the orientation of W, when linked to R$^1$ and the pyrimidine core of formula I, can be in either direction. For example, when W is —CH$_2$NR$^6$—, then W can be attached to its adjacent moieties in either orientation as shown:

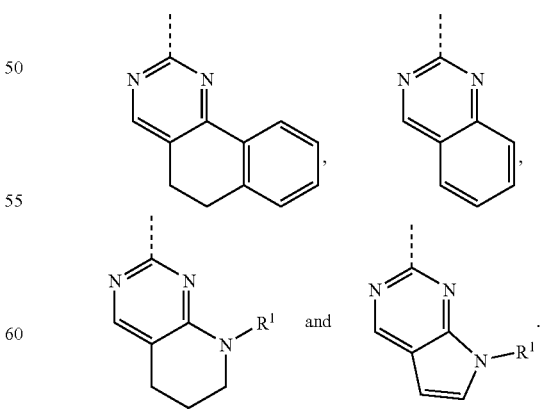

R$^1$ is $(C_1-C_6)$alkyl, $(C_1-C_6)$alkenyl, hetero$(C_2-C_6)$alkyl, cyclo$(C_3-C_7)$alkyl, heterocyclo$(C_3-C_7)$alkyl, aryl, heteroaryl, aryl$(C_1-C_4)$alkyl or heteroaryl$(C_1-C_4)$alkyl. Exemplary R$^1$ groups include thiophenyl, furyl, oxazolyl, pyrrolyl, thiazolyl, cyclohexyl, cyclopentyl, cyclobutyl, cyclopropyl, methyl, ethyl, isopropyl, ethenyl, propenyl, pyrrolidinyl, thienyl, piperidinyl and phenyl.

In some embodiments, R$^1$ is a partially saturated heteroaryl.

In certain embodiments, R$^1$ is unsubstituted. In other embodiments, R$^1$ is substituted with, for example, one or more substituents selected from $(C_1-C_8)$alkyl, halo$(C_1-C_4)$alkyl, halo, cyclo$(C_3-C_7)$alkyl, hetero$(C_2-C_8)$alkyl, aryl, heteroaryl, aryl$(C_1-C_4)$alkyl, hydroxyl, =O, —CN, —C(O)R', —CO$_2$R', —C(O)NR'R", —NR'R", —S(O)$_k$R' and —S(O)$_k$NR'R".

In some embodiments, —W—R$^1$ taken together are selected from $(C_1-C_6)$alkyl, cyclo$(C_3-C_7)$alkyl, heterocyclo$(C_3-C_7)$alkyl, aryl, or heteroaryl.

R$^2$ is hydrogen, halogen, $(C_1-C_6)$alkyl, —CN, halo$(C_1-C_6)$alkyl, $(C_1-C_6)$alkoxy, halo$(C_1-C_6)$alkoxy or $(C_2-C_6)$alkenyl. Exemplary R$^2$ groups include fluoro, chloro, methyl, ethyl, trifluoromethyl and trifluoromethoxy.

Optionally, R$^2$ and W taken together, or R$^2$ and R$^1$ taken together, form a 5- or 6-membered fused ring containing 0, 1, 2 or 3 heteroatoms selected from O, S, and N. Exemplary embodiments where R$^2$ and W, or R$^2$ and R$^1$, form a fused ring include the following, where the dashed line depicts a bond to the pyrazole core of formula I:

R$^3$ and R$^5$ are independently selected from hydrogen, hydroxy, halogen, —CN, $(C_1-C_6)$alkyl, halo$(C_1-C_6)$alkyl, $(C_1-C_6)$alkyloxy, and halo$(C_1-C_6)$alkoxy.

$R^4$ is $(C_1-C_8)$alkyl, hetero$(C_2-C_8)$alkyl, cyclo$(C_3-C_7)$alkyl, aryl, heteroaryl, aryl$(C_1-C_4)$alkyl or heteroaryl$(C_1-C_4)$alkyl. Exemplary $R^4$ groups include methyl, ethyl, propyl, butyl, pentyl, hexyl, heptyl, isopropyl, 2-methylpropyl, 3-methylbutyl, trifluoromethyl, methoxyl, methoxymethyl, methoxyethyl, ethoxyl, ethoxymethyl, ethoxyethyl, cyclopropylmethyl, 2-cyclopropylethyl, 3-cyclopropylpropyl, 4-chlorophenyl, 4-fluorophenyl, 4-methoxyphenyl, benzyl, 2-phenylethyl, 3-phenylpropyl, pyridin-2-yl, pyridin-3-yl, pyridin-3-yl-methyl and 2-pyridin-3-yl-ethyl.

In certain embodiments, $R^4$ is $(C_4-C_6)$alkyl, hetero$(C_4-C_6)$alkyl or cyclo$(C_4-C_6)$alkyl.

In some embodiments, $R^4$ is $(C_2-C_8)$alkoxy or $(C_3-C_8)$alkoxyalkyl.

$R^6$ is hydrogen, $(C_1-C_8)$alkyl, fluoro$(C_1-C_4)$alkyl, hetero$(C_2-C_8)$alkyl, aryl, heteroaryl, aryl$(C_1-C_4)$alkyl, —C(O)R', —CO$_2$R', —C(O)NR'R", —S(O)$_k$R' or —S(O)$_k$NR'R".

$R^7$ and $R^8$ independently are selected from hydrogen, $(C_1-C_8)$alkyl, fluoro$(C_1-C_4)$alkyl, hetero$(C_2-C_8)$alkyl, aryl, heteroaryl, and aryl$(C_1-C_4)$alkyl.

Each R' and R" is independently hydrogen, $(C_1-C_6)$alkyl, cyclo$(C_3-C_8)$alkyl, aryl or aryl$(C_1-C_4)$alkyl.

Each subscript k is 0, 1 or 2.

In certain embodiments of formula I, $R^2$ is methyl, trifluoromethyl or chloro, $R^3$ is hydrogen and $R^5$ is hydrogen. In some further embodiments, $R^4$ is $(C_4-C_6)$alkyl, hetero$(C_4-C_6)$alkyl or cyclo$(C_4-C_6)$alkyl.

In some embodiments, L is $(C_2-C_5)$alkenylene. In some embodiments L is —(CH$_2$)$_n$—C(O)N(R$^7$)—(CH$_2$)$_p$—, wherein $R^7$ is hydrogen, subscript n is 0 or 1 and subscript p is 0, 1 or 2. In some embodiments L is —(CH$_2$)$_n$—N(R$^7$)C(O)N(R$^8$)—(CH$_2$)$_p$—, wherein $R^7$ and $R^8$ are hydrogen and subscript n and subscript p are independently 0 or 1. In some embodiments, L is —CH=CHCH$_2$—, —C(O)NH—, —C(O)NHCH$_2$— or —C(O)NHCH$_2$CH$_2$—.

In some embodiments, V and L taken together are selected from the following, where the dashed line depicts a bond to the pyrazole core of formula I:

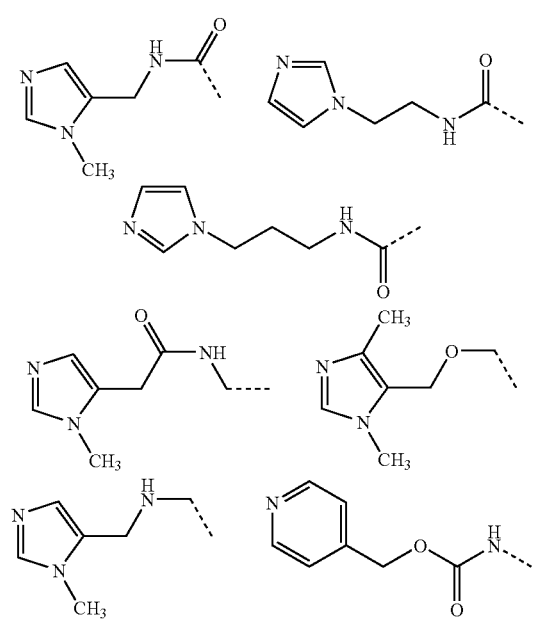

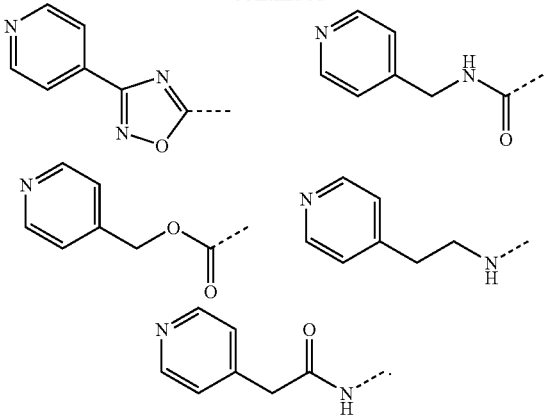

In some embodiments, W is a single bond, $(C_1-C_5)$alkylene or $(C_2-C_5)$alkenylene.

In some embodiments, W and $R^1$ taken together are selected from the following, where the dashed line depicts a bond to the pyrimidine core of formula I:

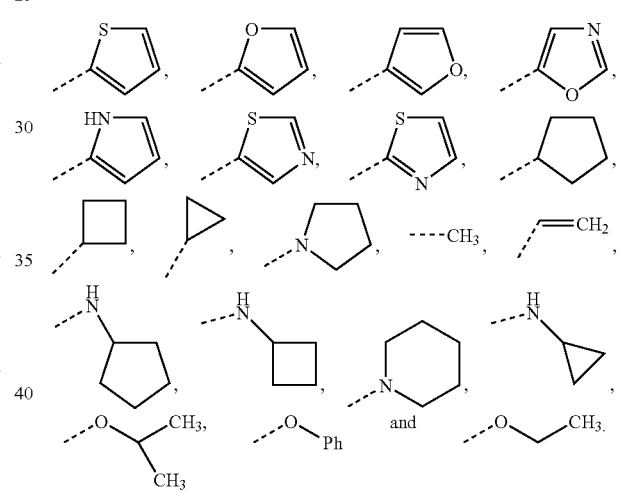

In certain embodiments, the invention provides compounds of formula II:

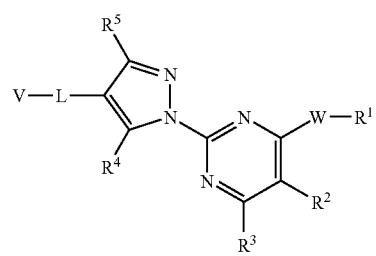

II wherein L, V, W, $R^1$, $R^2$, $R^3$, $R^4$ and $R^5$ are as defined above with regard to formula I.

In some embodiments, $R^4$ is $(C_2-C_8)$alkoxy or $(C_3-C_8)$alkoxyalkyl.

In certain embodiments of formula II, $R^2$ is methyl, trifluoromethyl or chloro, $R^3$ is hydrogen and $R^5$ is hydrogen. In some further embodiments, $R^4$ is $(C_4-C_6)$alkyl, hetero$(C_4-C_6)$alkyl or cyclo$(C_4-C_6)$alkyl.

In some embodiments, L is —CH=CHCH$_2$—, —C(O)NH—, —C(O)NHCH$_2$— or —C(O)NHCH$_2$CH$_2$—.

In some embodiments, V and L taken together are selected from the following, where the dashed line depicts a bond to the pyrazole core of formula II:

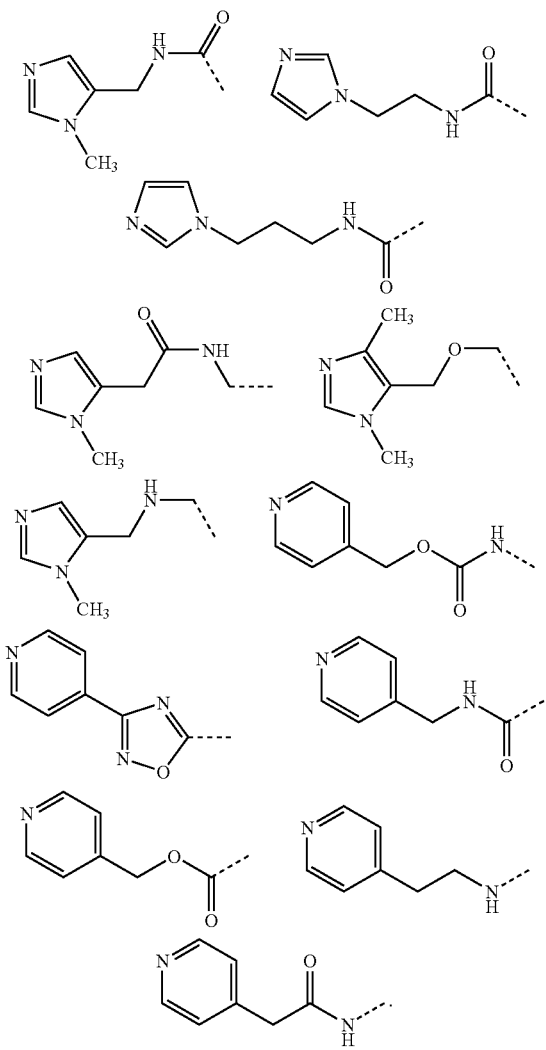

In some embodiments, W and $R^1$ taken together are selected from the following, where the dashed line depicts a bond to the pyrimidine core of formula II:

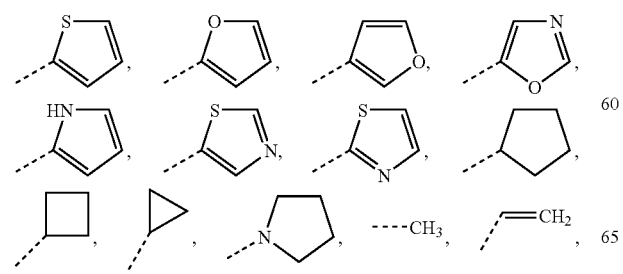

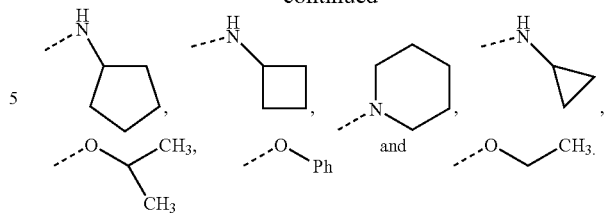

In certain embodiments, the present invention provides compounds of formula III:

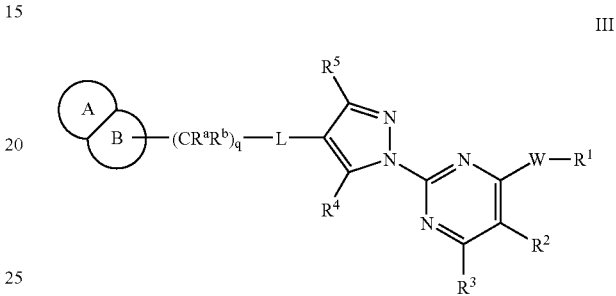

III wherein L, W, $R^1$, $R^2$, $R^3$, $R^4$ and $R^5$ are as defined above with regard to formula I.

In formula III, $R^a$ and $R^b$ are independently selected from hydrogen, $(C_1-C_5)$alkyl, cyclo$(C_3-C_5)$alkyl, halo$(C_1-C_5)$alkyl, aryl, heteroaryl, and aryl$(C_1-C_4)$alkyl.

Subscript q is 0, 1, 2 or 3.

Structure

is a fused ring structure wherein ring A is a 5- or 6-membered ring containing 0, 1, 2 or 3 heteroatoms selected from O, S and N, and ring B is a 5-, 6-, 7- or 8-membered ring containing 0, 1, 2, 3 or 4 heteroatoms selected from O, S and N.

In some embodiments, rings A and B are fully saturated.

In certain embodiments, rings A and B taken together comprise a partially saturated heteroaryl.

Examples of part

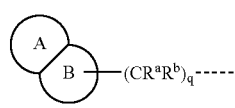

of formula III, where the dashed line indicates attachment to L or to the pyrazole core where L is a single bond in formula III, include the following:

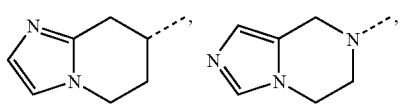

-continued

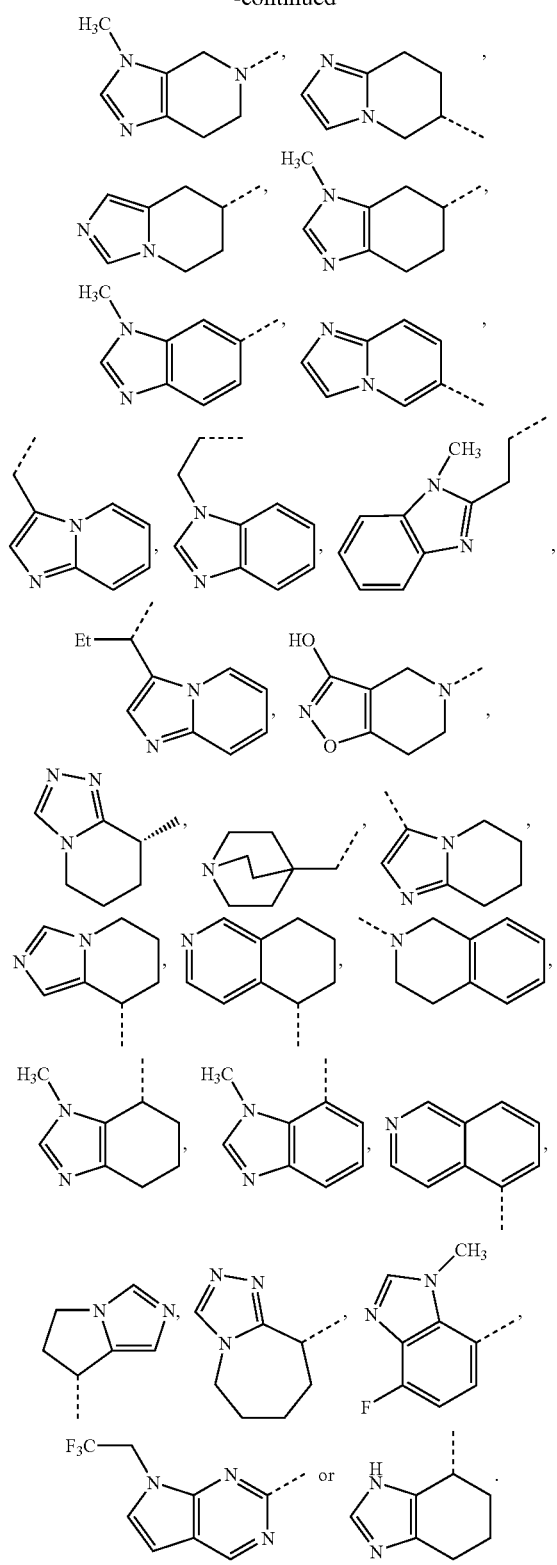

In some embodiments of formula III, L is —CH=CHCH$_2$—, —C(O)NH—, —C(O)NHCH$_2$— or —C(O)NHCH$_2$CH$_2$—.

In certain embodiments, R$^2$ is methyl, trifluoromethyl or chloro, R$^3$ is hydrogen and R$^5$ is hydrogen.

In certain embodiments, the compound provided has formula IV or V:

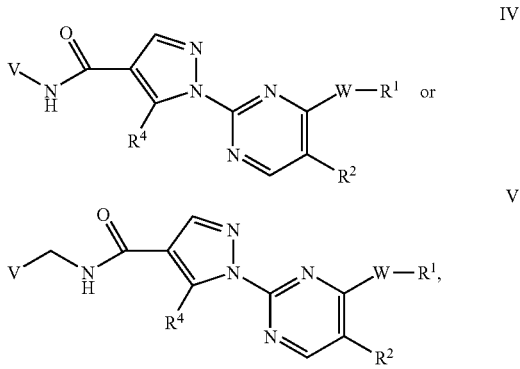

where V, W, R$^1$, R$^2$ and R$^4$ are as defined above with regard to formula I.

In some embodiments of formula IV or V, R$^2$ is methyl, trifluoromethyl, chloro or fluoro.

In some embodiments, W is a single bond.

In some embodiments, R$^1$ is group selected from furyl, thiophenyl, thienyl, piperidinyl, isoxazolyl, oxazolyl, thiazolyl, pyrrolyl, cyclobutyl and cyclopentyl.

In certain embodiments, the compound provided has formula VI:

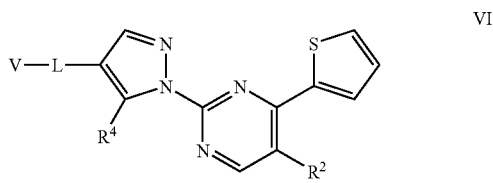

where V, L, R$^2$ and R$^4$ are as defined above with regard to formula I.

In certain embodiments, the compound provided has formula VII:

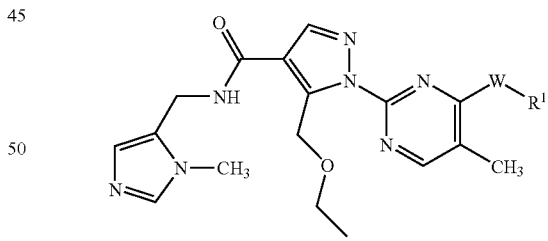

where W and R$^1$ are as defined above with regard to formula I.

In certain embodiments, W is a single bond.

In some embodiments, R$^1$ is group selected from furyl, thiophenyl, thienyl, piperidinyl, isoxazolyl, oxazolyl, thiazolyl, pyrrolyl, cyclobutyl and cyclopentyl. In some embodiments, R$^1$ is unsubstituted. In certain embodiments, R$^1$ is substituted with, for example, one or more substituents selected from (C$_1$-C$_8$)alkyl, halo(C$_1$-C$_4$)alkyl, halo, cyclo(C$_3$-C$_7$)alkyl, hetero(C$_2$-C$_8$)alkyl, aryl, heteroaryl, aryl(C$_1$-C$_4$)alkyl, hydroxyl, =O, —CN, —C(O)R', —CO$_2$R', —C(O)NR'R", —NR'R", —S(O)$_k$R' and —S(O)$_k$NR'R", where R' and R" are as defined above with regard to formula I.

The compounds of formulas I-VII include pharmaceutically acceptable salts, solvates or prodrugs thereof.

The invention encompasses novel compounds, novel pharmaceutical compositions and/or novel methods of use.

6.2.2. Preparation of the Compounds

The compounds of the invention can be prepared by a variety of synthetic or semisynthetic techniques. For example, starting materials can be prepared as shown in general Schemes A and B for use in synthesizing compounds as shown in Scheme C, where $R^1$, $R^2$, $R^4$, V and W are as defined in formula I. Exemplary compounds prepared following the syntheses shown in Schemes A-C are discussed in Section 7.

Scheme A

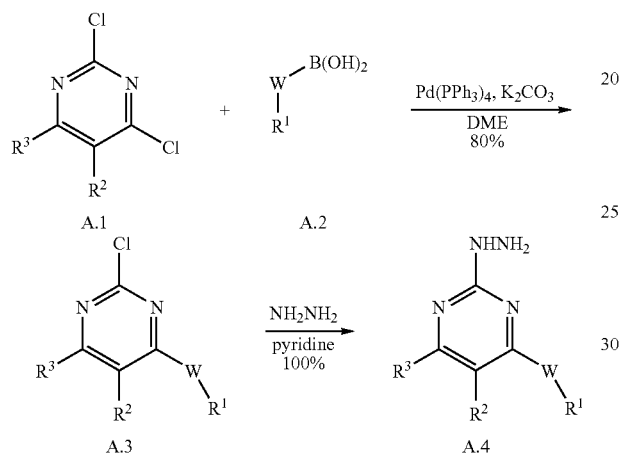

Scheme B

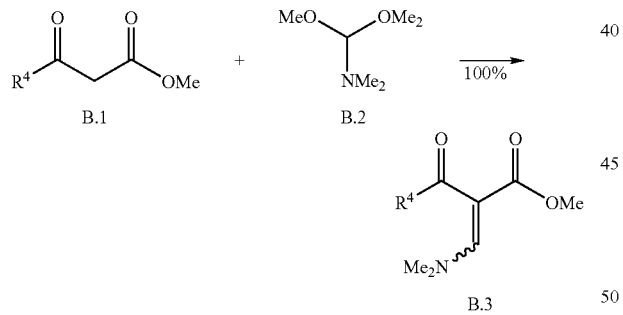

Scheme C

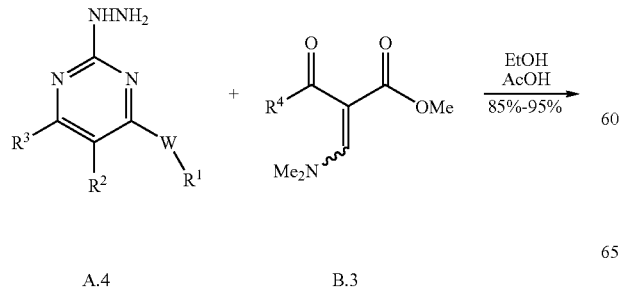

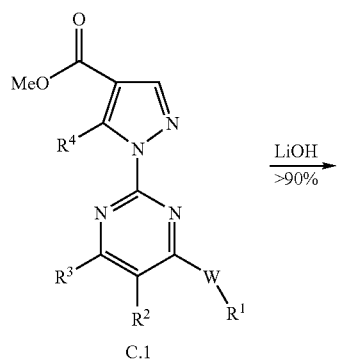

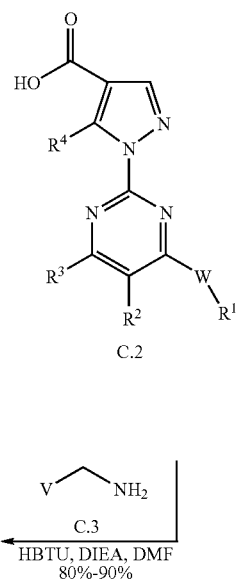

As another example, Scheme D provides a general synthesis for pyrazolyl pyrimidine compounds of the invention, where $R^1$, $R^2$, $R^4$, V and W are as defined in formula I.

Scheme D

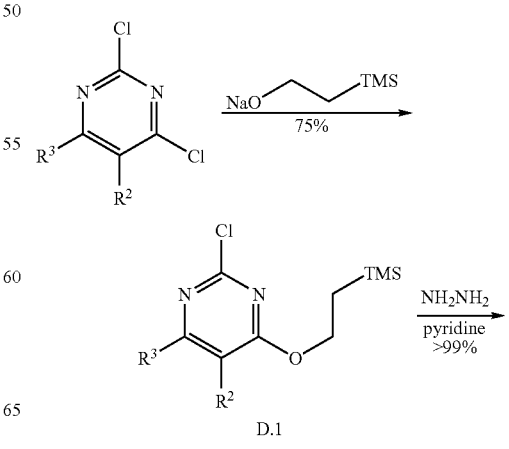

-continued

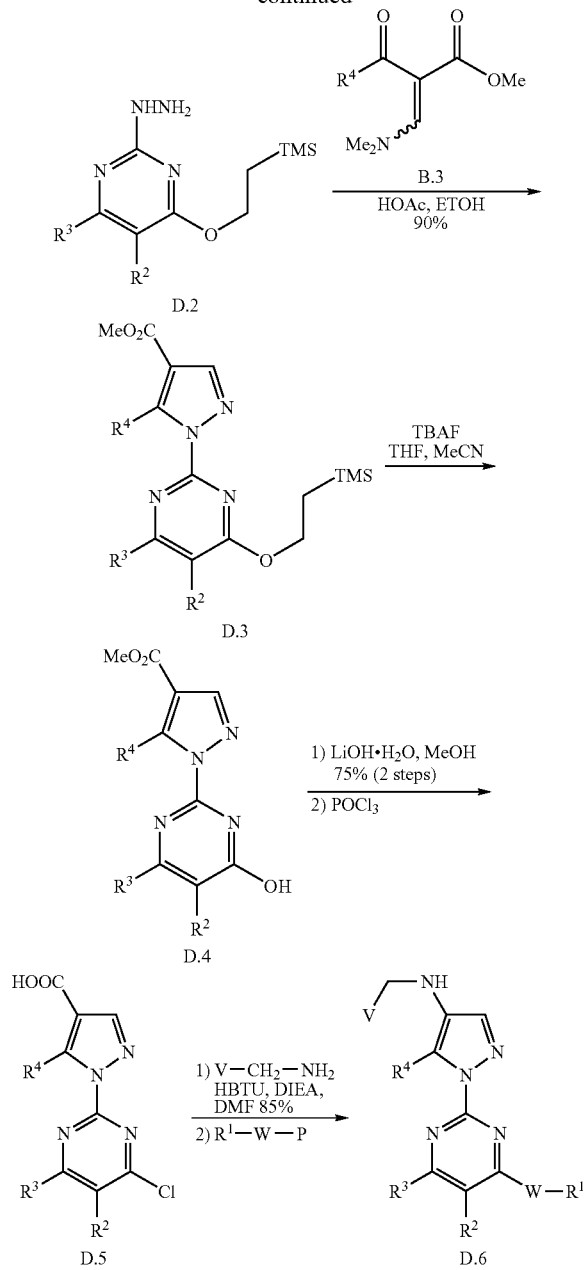

Additional exemplary synthesis routes to the compounds provided herein are described in the Examples below. Synthesis of appropriate starting materials can be prepared by techniques known or apparent to those of skill in the art or the starting materials may be commercially available. One of skill in the art will understand that the synthetic routes can be modified to use different starting materials and/or alternate reagents to accomplish the desired transformations, and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group. Accordingly, the methods and reagents described herein are all expressed as non-limiting embodiments.

6.2.3. Compositions

In one aspect, the invention provides pharmaceutical compositions suitable for pharmaceutical use comprising one or more compounds of the invention and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

Formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form, particularly single unit dosage form, suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452 and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions can contain the active materials in an admixture with excipients suitable for the manufacture of aqueous suspensions. Such excipients include, for instance, suspending agents, dispersing or wetting agents and the like, as known to those skilled in the art. Suspending agents include, for example, sodium carboxymethylcellulose, methylcellulose, hydroxy-propylmethylcellulose, sodium alginate, polyvinyl-pyrrolidone, gum tragacanth and gum acacia. Dispersing or wetting agents can, for example, be a naturally-occurring phosphatide such as lecithin, or condensation products of an alkylene oxide with fatty acids, for example, polyoxy-ethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions can contain one or more preservatives, for example ethyl, or n-propyl, p-hydroxybenzoate, one or more coloring agents, one or more flavoring agents, and/or one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical use, creams, ointments, jellies, solutions or suspensions, etc., containing the compounds of the invention are employed. As used herein, topical use is also meant to include the use of mouthwashes and gargles.

The pharmaceutical compositions and methods provided herein can further comprise other therapeutically active compounds, for example, as described in Section 6.2.4, useful in the treatment of diseases and conditions as described herein including type 2 diabetes, diabetic ketoacidosis, hyperglycemia, diabetic neuropathy, obesity, metabolic syndrome, inflammation, asthma, psoriasis, arthritis, rheumatoid arthritis, inflammatory bowel disease, cancer and neurologic disorder, or symptom thereof.

6.2.4. Methods of Use

In one aspect, methods are provided for treating or preventing a disease or condition associated with insufficient circulating insulin by administering to a subject having such a condition or disease, a therapeutically effective amount of a compound or composition of the invention. In one group of embodiments, diseases and conditions, including chronic diseases of humans or other species, can be treated with insulin secretagogues. These diseases and conditions include type 2 diabetes, ketoacidosis, hyperglycemia and diabetic neuropathy.

In one aspect, methods are provided for treating or preventing a disease or condition, or symptom thereof, in a subject in need of treatment or prevention, comprising administering an amount of a compound or composition as provided herein effective to treat or prevent the disease or condition. The methods of treatment or prevention can be utilized with any disease amenable to treatment or prevention by the compounds or compositions provided herein. In certain embodiments the disease or condition, or symptom thereof, to be treated or prevented is type 2 diabetes, diabetic ketoacidosis, hyperglycemia, diabetic neuropathy, obesity, metabolic syndrome, inflammation, asthma, psoriasis, arthritis, rheumatoid arthritis, inflammatory bowel disease, cancer or neurologic disorder.

In another aspect, the invention provides methods for modulating insulin concentration in plasma of a mammal, comprising administering an amount of a compound or composition as provided herein effective to modulate insulin concentration in plasma of the mammal.

In one aspect, the invention provides methods for increasing insulin concentration in plasma of a mammal, comprising administering an amount of a compound or composition as provided herein effective to increase insulin concentration in plasma of the mammal.

In one aspect, methods for modulating cellular function are provided. Cellular functions that can be modulated can, for example, include secretion of cell-signaling molecules, protein expression, proliferation, or cellular death. A cell whose function can be modified include, for example, a pancreatic β-cell, neuron, muscle cell or a cancer cell.

In one aspect, the invention provides methods for augmenting secretion by a pancreatic β-cell, comprising contacting the pancreatic β-cell with a composition or compound as provided herein.

In yet another aspect, the invention provides methods of treating or preventing a disease or condition responsive to insulin secretagogues, comprising administering to a subject having such a disease or condition, a therapeutically effective amount of one or more of the subject compounds or compositions.

Depending on the disease or symptom to be treated and the subject's condition, the compounds of the invention may be administered by oral, parenteral (e.g., intramuscular, intraperitoneal, intravenous, intracerebroventricular, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention of type 2 diabetes, ketoacidosis, hyperglycemia and diabetic neuropathy, or other diseases or conditions associated with insufficient circulating insulin, and diseases or conditions such as obesity, metabolic syndromes, inflammation, asthma, psoriasis, arthritis, rheumatoid arthritis, inflammatory bowel disease, cancer and neurologic disorders, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type 2 diabetes, ketoacidosis, hyperglycemia, diabetic neuropathy, obesity, metabolic syndrome, inflammation, asthma, psoriasis, arthritis, rheumatoid arthritis, inflammatory bowel disease, cancer or neurologic disorder. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of other therapeutic agents that may be combined with a compound of the invention, either administered separately or in the same pharmaceutical compositions, include, but are not limited to: sulfonylureas, for example, glibenclamide (DAONIL®), glimepiride (AMARYL®), glipizide (GLUCOTROL® or MINODIAB®), glyburide (MICRONASE®), and meglinitide; insulin and insulin mimetics; biguanides such as metformin (GLUCOPHAGE®); α-glucosidase inhibitors including acarbose (PRECOSE®) and miglitol (GLYSET®); meglitinides, for example, nateglinide (STARLIX®) and repaglinide (PRANDIN®); thiozolidinediones, for example, ciglitazone, englitazone, rosiglitazone (AVANDIA®), pioglitazone (ACTOS®) and troglitazone (REZULIN®); dipeptidyl-peptidase IV (DPP-IV) inhibitors, for example, sitagliptin (JANUVIA®), vildagliptin (GALVUS®), saxagliptin, denagliptin, and SYR-222; incretin mimetics such as exenatide (BYETTA™); cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat). The weight ratio of the compound of the invention to the second active ingredient may be varied and will depend upon the effective dose of each ingredient. Generally, an effective dose of each will be used. Thus, for example, when a compound of the invention is combined with a cholesterol lowering agent, the weight ratio of the compound of the invention to the cholesterol lowering agent will generally range from about 1000:1 to about 1:1000, preferably about 200:1 to about 1:200. Combinations of a compound of the invention and other active ingredients will generally also be within the aforementioned range, but in each case, an effective dose of each active ingredient should be used.

6.3. Assays

The antidiabetic effects of the compounds provided herein can be demonstrated using a variety of in vitro and in vivo assays including a number of animal models. Animal models for testing compounds include, for example, mouse strains in which type 2 diabetes characteristics have arisen spontaneously or were produced by selective breeding (see, e.g., Suzuki (1999) *Exp. Anim.* 48:181-189 and citations therein; Hamada et al. (2001) *Metabolism* 50:1282-1285 (spontaneously diabetic Nagoya-Shibata-Yasuda mice); Kawano et al. (1992) *Diabetes* 41, 1422-1428 (Otsuka Long Evans Tokushima Fatty (OLETF) rats); Miura et al. (2006) *Biol. Pharm. Bull.* 29:585-587 (strain KK-Ay mice, available, for instance, from The Jackson Laboratory (Bar Harbor, Me.) (JAX® GEMM® strain mice)), or were produced by transgenic technology (see, e.g., Butler et al. (2004) *Diabetes*

53:1509-1516 (describing Human Islet Amyloid Polypeptide (HIP) rats)). Non-genetic-based or induced animal models of diabetes are also available, including, for example, animals with diet-induced diabetes (see, e.g., Leibowitz et al. (2001) *Diabetes* 50:S113-S117 (describing the gerbil *Psammomys Obesus* model of type 2 diabetes)), induced by a combination of high-fat diet and streptozotocin (STZ) injections or by neonatal STZ injections (see, e.g., Zhang et al. (2003) *Exp. Anim.* 52:401-407; Reed et al. (2000) *Metabolism* 49:1390-1394; Wang et al. (1996) *J. Pharmacol. Exp. Ther.* 278:82-89; Kergoat et al. (1986) *Diabete Metab.* 12:79-82; Portha et al. (1989) *Diabete Metab.* 15:61-75). Compounds can be evaluated using assays that, for example, measure levels of circulating glucose and/or insulin and/or other pertinent component, such as C-peptide, in an animal model, or that measure secretion from perfused pancreatic preparations or secretion from isolated pancreatic cells (e.g., β or islet cells), as described, for example, in the references cited above and others including Portha et al. (1991) *Diabetes* 40:486-491; Latha et al. (2004) *Life Sci.* 75:2003-2014; Garcia-Lopez et al. (2004) *Eur. J. Pharmacol.* 504:139-142; Gunawardena et al. (2005) *BMC Endocr. Disord.* 5:9; Lupi et al. (1997) *Acta Diabetol.* 34:46-48; Gregario et al. (1992) *Diabetes Res. Clin. Pract.* 18:197-206. Additional examples of how compounds can be evaluated in isolated rodent islets, perfused and perifused islets and in a variety of diabetic animal models include Gotoh et al. (1987) *Transplantation* 43:725-730; Silvestre et al. (2001) *Horm. Metab. Res.* 33:379-381; and Young et al. (1999) *Diabetes* 48:1026-1034. In addition, modulation of secretion from isolated pancreatic cells can be assessed by measuring membrane voltage changes, second messenger activation (e.g., cAMP, $IP_3$ or $Ca^{2+}$) levels, ion flux, phosphorylation levels, transcription levels, and the like. Additional exemplary assays are described in the Section 7 below.

7. EXAMPLES

The following examples are offered by way of illustration and are not intended to limit the scope of the invention. Those of skill in the art will readily recognize a variety of noncritical parameters that could be modified to yield essentially similar results.

Reagents and solvents used below can be obtained from commercial sources such as Sigma-Aldrich Co. (St. Louis, Mo., USA). $^1$H-NMR spectra were recorded on a VARIAN GEMINI 400 MHz NMR spectrometer, VARIAN MERCURY 400 NMR spectrometer, or UNITINOVA 500 NMR spectrometer. Significant peaks are tabulated in the order: chemical shift, multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

7.1. Example 1

5-(Methoxymethyl)-1-(5-methyl-4-(thiophen-2-yl)pyrimidin-2-yl)-N-(pyridin-4-ylmethyl)-1H-pyrazole-4-carboxamide (1). The general synthetic Schemes A-C (see Section 6.2.2) are followed in Examples 1-13.

Step 1. A mixture of 2,4-dichloro-5-methylpyrimidine A.1 (2.1 g, 15.4 mmol, available from Aldrich Chemicals, Milwaukee, Wis.), thiophene-2-boronic acid A.2 (W—$R^1$=thiophen-2-yl in Scheme A) (1.98 g, 15.4 mmol), potassium carbonate (6.42 g, 46.4 mmol), Pd(PPh$_3$)$_4$ (1.79 g, 1.54 mmol) and DME (39 mL) in a sealed tube was allowed to stir at 110° C. for 20 hours. Upon completion, the mixture was filtered and the precipitate was washed with methylene chloride (50 mL×4). The combined organic phases were washed with 2 N hydrochloric acid, water, saturated sodium bicarbonate solution and brine, dried over anhydrous sodium sulfate and concentrated. The residue was purified by column chromatography eluted with 10% EtOAc/hexane to give 2.1 g (80%) of A.3 ($R^2$=Me, W—$R^1$=2-thiophenyl).

Step 2. A mixture of 2-chloro-5-methyl-4-(thiophen-2-yl) pyrimidine A.3 ($R^2$=Me, W—$R^1$=thiophen-2-yl, $R^3$=H, 96 mg, 0.457 mmol), anhydrous hydrazine (150 mg, 4.57 mmol) and pyridine (1 mL) was heated at 90° C. for 1 hour, At the completion of the reaction, the mixture was concentrated to give 94 mg (100%) of A.4 ($R^2$=Me, W—$R^1$=thiophen-2-yl, $R^3$=H), which was used directly in the next step.

Step 3. The synthesis of methyl 2-((dimethylamino)methylene)-4-methoxy-3-oxobutanoate B.3 ($R^4$=methoxymethyl) was accomplished by first mixing methyl 4-methoxy-3-oxobutanoate B.1 ($R^4$=methoxymethyl, 1 mL, 8.69 mmol) and dimethoxy-N,N-dimethylmethanamine B.2 (2.32 mL, 17.4 mmol) at room temperature for 24 hours followed by removing excess unreacted dimethoxy-N,N-dimethylmethanamine under vacuum to give B.3 ($R^4$=methoxymethyl, 1.55 g, 100%).

A mixture of 1-(5-methyl-4-(thiophen-2-yl)pyrimidin-2-yl)hydrazine A.4 ($R^2$=Me, W—$R^1$=thiophen-2-yl, $R^3$=H) and 2-((dimethylamino)methylene)-4-methoxy-3-oxobutanoate B.3 (R=methoxymethyl, 94 mg, 0.456 mmol) in 3 mL of ethanol in the presence of 90 µL of acetic acid was refluxed for 2 hours. Upon completion, the mixture was concentrated, and the residue was dissolved in 50 mL of ethyl acetate. The solution was washed with 2 N HCl solution, water, saturated sodium bicarbonate solution and brine, dried over anhydrous sodium sulfate and concentrated. The crude material was purified by column chromatography using 35% EtOAc/hexane as the eluent to give 110 mg of C.1 ($R^2$=Me, W—$R^1$=thiophen-2-yl, $R^3$=H, $R^4$=methoxymethyl).

Step 4. To a solution of methyl 5-(methoxymethyl)-1-(5-methyl-4-(thiophen-2-yl)pyrimidin-2-yl)-1H-pyrazole-4-carboxylate C.1 ($R^2$=Me, W—$R^1$=thiophen-2-yl, $R^3$=H, $R^4$=methoxymethyl) (110 mg, 0.319 mmoL) in 4 mL of dioxane was added a solution of lithium hydroxide monohydrate (67 mg, 1.60 mmol) in 1 mL of water. The resulting mixture was allowed to stir at room temperature for 16 hours. Upon completion, the mixture was concentrated and 10 mL of 2 N aqueous HCl solution was added to the residue. The resulting mixture was extracted with methylene chloride (30 mL×3). The combined extracts were washed with 2 N hydrochloric acid and water twice, dried over anhydrous sodium sulfate and concentrated. The residue was further dried to give 110 mg of C.2 ($R^2$=Me, W—$R^1$=thiophen-2-yl, $R^3$=H, $R^4$=methoxymethyl).

Step 5. The coupling reaction between C.2 and C.3 to compound 1 can be accomplished in a number of ways. Two typical methods are exemplified here.

Method A: A mixture of acid C.2 ($R^2$=Me, W—$R^1$=thiophen-2-yl, $R^3$=H, $R^4$=methoxymethyl, 1 mole equivalent), amine C.3 (2 mole equivalent), HBTU (1 mole equivalent) and diisopropylethylamine (4 equivalent) in DMF (1 M) is stirred at 50° C. The reaction is monitored by LCMS. The crude material is purified by HPLC to give the desired product 1.

Method B: A mixture of 5-(methoxymethyl)-1-(5-methyl-4-(thiophen-2-yl)pyrimidin-2-yl)-1H-pyrazole-4-carboxylic acid C.2 ($R^2$=Me, W—$R^1$=thiophen-2-yl, $R^3$=H, $R^4$=methoxymethyl) (110 mg, 0.332 mmol), pyridin-4-ylmethanamine C.3 (V=4-pyridinyl) (72 mg, 0.664 mmol), EDC (128 mg, 0.664 mmol), HOBT (43 mg, 0.132 mmol) and N-methylmorpholine (NMMP, 97 µL, 0.83 mmol) in 3 mL of methylene chloride was stirred at room temperature overnight (20 hours). Upon completion, an additional 50 mL of methylene chloride was added and the resulting mixture was washed with water and brine, dried over anhydrous sodium sulfate and concentrated. The crude material was purified by column chromatography using 10% $CH_3OH/CH_2Cl_2$ as the eluent to give 60 mg of 1. $^1$H NMR 400 MHz ($CDCl_3$) δ: 8.52 (s, 1H), 8.40 (d, J=5.90 Hz, 2H), 8.32 (br s, 1H), 8.09 (s, 1H), 7.69 (d, J=3.85 Hz, 1H), 7.50 (dd, J=5.09, 0.77 Hz, 1H), 7.15 (d, J=5.90 Hz, 2H), 7.10 (dd, J=5.0 Hz, 3.86 Hz, 1H), 5.25 (s, 2H), 4.45 (d, J=5.82 Hz, 2H), 3.15 (s, 3H), 2.50 (s, 3H). LCMS (ES+) m/z 421 (M+1).

7.2. Example 2

5-Butyl-N-(3-methoxypropyl)-1-(5-methyl-4-(thiophen-2-yl)pyrimidin-2-yl)-1H-pyrazole-4-carboxamide (2). Compound 2 was prepared by following the procedures described in Example 1 with the exception that B.1 was methyl 3-oxoheptanoate in place of methyl 4-methoxy-3-oxobutanoate in Step 3 and that 3-methoxypropylamine was used in place of pyridin-4-ylmethanamine with 3-methoxypropylamine in Step 5. $^1$H NMR 400 MHz ($CDCl_3$) δ 8.64 (s, 1H), 7.82 (s, 1H), 7.80 (dd, J=3.85, 0.94 Hz, 1H), 7.61 (dd, J=5.09, 0.93 Hz, 1H), 7.22 (dd, J=5.07, 3.87 Hz, 1H), 6.62 (br s, 1H), 3.52-3.63 (m, 6H), 3.38 (s, 3H), 2.61 (s, 3H), 1.87 (m, 2H), 1.63 (m, 2H), 1.37 (m, 2H), 0.839 (dd, J=7.31, 7.31 Hz, 3H). LCMS (ES+) m/z 414 (M+1).

7.3. Example 3

5-Butyl-1-(5-methyl-4-(thiophen-2-yl)pyrimidin-2-yl)-N-(3-(methylsulfonyl)propyl)-1H-pyrazole-4-carboxamide (3). The preparation of 3 was similar to that described in Example 1 where 3-methoxypropylamine was replaced with 3-methylsulfonylpropylamine. $^1$H NMR 400 MHz ($CDCl_3$) δ 8.62 (s, 1H), 7.94 (s, 1H), 7.79 (s 1H), 7.60 (br s, 1H), 7.21 (br s, 1H), 6.61 (br s, 1H), 3.60 (m, 4H), 3.14 (m, 2H), 2.93 (s, 3H), 2.60 (s, 3H), 2.18 (m, 2H), 1.60 (m, 2H), 1.37 (m, 2H), 0.835 (dd, J=7.01, 7.01 Hz, 3H). LCMS (ES+) m/z 462 (M+1).

7.4. Example 4

N-((1-Methyl-1H-imidazol-5-yl)methyl)-1-(5-methyl-4-(thiophen-2-yl)pyrimidin-2-yl)-5-phenyl-1H-pyrazole-4-carboxamide (4). Following procedures described in Example 1 with the exception of substituting methyl 4-methoxy-3-oxobutanoate with methyl 3-oxo-3-phenylpropanate as B.1 in Step 3 and substituting pyridin-4-ylmethanamine with (1-methyl-1H-imidazol-5-yl)methanamine in Step 5, the titled compound 4 was obtained. $^1$H NMR 400 MHz ($CDCl_3$) δ 8.55 (s, 1H), 8.29 (s, 1H), 7.45 (d, J=5.09 Hz, 1H), 7.34-7.41 (m, 7H), 7.04 (dd, J=4.20, 4.13 Hz, 1H), 6.66 (s, 1H), 5.32 (br s, 1H), 4.29 (d, J=5.40 Hz, 2H), 3.49 (s, 3H), 2.52 (s, 3H). LCMS (ES+) m/z 456 (M+1).

7.5. Example 5

5-(2-chlorophenyl)-N-((1-methyl-1H-imidazol-5-yl)methyl)-1-(5-methyl-4-(thiophen-2-yl)pyrimidin-2-yl)-1H-pyrazole-4-carboxamide (5). Compound 5 was prepared following similar procedures to those described in Example 1 with the exceptions of substituting methyl 4-methoxy-3-oxobutanoate with methyl 3-oxo-3-(2-chlorophenyl)propanate as B.1 in Step 3 and substituting pyridin-4-ylmethanamine with (1-methyl-1H-imidazol-5-yl)methanamine in Step 5. $^1$H NMR 400 MHz ($CDCl_3$) δ 8.56 (s, 1H), 8.30 (s, 1H), 7.33-7.44 (m, 7H), 7.05 (dd, J=4.89, 4.84 Hz, 1H), 6.70 (s, 1H), 5.28 (dd, J=4.55, 4.55 Hz, 1H), 4.14 (dd, J=5.36, 3.30 Hz, 2H), 3.51 (s, 3H), 2.52 (s, 3H). LCMS (ES+) m/z 490 (M+1).

7.6. Example 6

5-(4-fluorophenyl)-N-((1-methyl-1H-imidazol-5-yl)methyl)-1-(5-methyl-4-(thiophen-2-yl)pyrimidin-2-yl)-1H-pyrazole-4-carboxamide (6). Compound 6 was prepared following similar procedures described in Example 1 with the exception of substituting methyl 4-methoxy-3-oxobutanoate with methyl 3-oxo-3-(4-fluorophenyl)propanate as B.1 in Step 3 and substituting pyridin-4-ylmethanamine with (1-methyl-1H-imidazol-5-yl)methanamine in Step 5. $^1$H NMR 400 MHz ($CDCl_3$) δ 8.55 (s, 1H), 8.23 (s, 1H), 7.49 (d, J=4.61 Hz, 1H), 7.46 (d, J=3.70 Hz, 1H), 7.36-7.41 (m, 3H), 7.08-7.12 (m, 3H), 6.80 (s, 1H), 5.49 (br s, 1H), 4.45 (d, J=5.40 Hz, 2H), 3.54 (s, 3H), 2.53 (s, 3H). LCMS (ES+) m/z 462 (M+1).

7.7. Example 7

5-Butyl-1-(5-methyl-4-(thiophen-2-yl)pyrimidin-2-yl)-N-((4-methyl-4H-1,2,4-triazol-3-yl)methyl)-1H-pyrazole-4-carboxamide (7). A sample of the acid intermediate C.2 ($R^4$=n-butyl) from Example 1 was coupled with (4-methyl-4H-1,2,4-triazol-3-yl)methanamine to give 7. $^1$H NMR 400 MHz ($CDCl_3$) δ 8.60 (s, 1H), 8.19 (s, 1H), 8.10 (dd, J=5.1, 5.1 Hz, 1H), 8.04 (s, 1H), 7.76 (d, J=3.81 Hz, 1H), 7.58 (d, J=5.07 Hz, 1H), 7.20 (dd, J=4.54, 4.35 Hz, 1H), 4.78 (d, J=5.63 Hz, 2H), 3.76 (s, 3H), 3.62 (dd, J=7.57, 7.57 Hz, 2H), 2.58 (s, 3H), 1.59 (m, 2H), 1.36 (m, 2H), 0.819 (dd, J=7.23, 7.23 Hz, 3H). LCMS (ES+) m/z 437 (M+1).

7.8. Example 8

5-Butyl-N-((4,5-dimethyl-4H-1,2,4-triazol-3-yl)methyl)-1-(5-methyl-4-(thiophen-2-yl)pyrimidin-2-yl)-1H-pyrazole-4-carboxamide (8). Compound 8 was prepared similar to the procedure in Example 7, except that (4,5-dimethyl-4H-1,2,4-triazol-3-yl)methanamine was substituted for (4-methyl-4H-1,2,4-triazol-3-yl)methanamine in the final coupling step. $^1$H NMR 400 MHz ($CDCl_3$) δ 8.69 (s, 1H), 8.15 (s, 1H), 7.84 (d, J=3.76 Hz, 1H), 7.65 (d, J=5.09 Hz, 1H), 7.57 (dd, J=4.83, 4.48 Hz, 1H), 7.27 (dd, J=4.82, 4.07 Hz, 1H), 4.81 (d, J=5.59 Hz, 2H), 3.68 (obscured dd, J=7.78, 7.75 Hz, 2H), 3.67 (s, 3H), 2.66 (s, 3H), 2.46 (s, 3H), 1.66 (m, 2H), 1.42 (m, 2H), 0.873 (dd, J=7.30, 740 Hz, 3H). LCMS (ES+) m/z 451 (M+1).

7.9. Example 9

5-Butyl-1-(5-methyl-4-(thiophen-2-yl)pyrimidin-2-yl)-N-(6,7,8,9-tetrahydro-5H-[1,2,4]triazolo[4,3-a]azepin-9-yl)-1H-pyrazole-4-carboxamide (9). The 6,7,8,9-tetrahydro-5H-[1,2,4]triazolo[4,3-a]azepin-9-amine intermediate C.3

(see Scheme C) was prepared following procedures reported in the literature for similar systems, starting from 3-aminoazepan-2-one. The coupling step to C.2 was accomplished in the same manner as described in previous examples, to result in the compound 9. $^1$H NMR 500 MHz (CDCl$_3$) δ 8.64 (s, 1H), 8.09 (s, 1H), 8.08 (s, 1H), 7.80 (d, J=4.90 Hz, 1H), 7.66 (d, J=5.80 Hz, 1H), 7.59 (d, J=4.90 Hz, 1H), 7.21 (dd, J=4.66, 4.16 Hz, 1H), 5.22 (m, H), 4.30 (d, J=13.9 Hz, 1H), 3.84 (dd, J=13.2, 13.0 Hz, 1H), 3.61 (m, 2H), 2.61 (s, 3H), 2.50 (d, J=13.4 Hz, 1H), 2.17 (d, J=14.2 Hz, 1H), 2.10 (d, J=14.05 Hz, 1H), 1.92 (m, 1H), 1.65 (m, 2H), 1.49 (m, 2H), 1.36 (m, 2H), 0.827 (dd, J=7.23, 7.23 Hz, 3H). LCMS (ES+) m/z 477 (M+1).

7.10. Example 10

5-Butyl-1-(5-methyl-4-(thiophen-2-yl)pyrimidin-2-yl)-N-(1-(4-methyl-4H-1,2,4-triazol-3-yl)cyclopropyl)-1H-pyrazole-4-carboxamide (10). Compound 10 was prepared following the procedures in Example 1 by substituting 1-(4-methyl-4H-1,2,4-triazol-3-yl)cyclopropanamine for pyridine-4-ylmethylamine in Step 5. $^1$H NMR 400 MHz (CDCl$_3$) δ 8.69 (s, 1H), 8.62 (s, 1H), 8.16 (s, 1H), 8.08 (s, 1H), 7.84 (d, J=3.56 Hz, 1H), 7.65 (d, J=4.94 Hz, 1H), 7.27 (obscured dd, J=5.09, 4.17 Hz, 1H), 4.27 (s, 3H), +3.62 (dd, J=7.68, 7.68 Hz, 2H), 2.66 (s, 3H), 1.57-1.69 (m, 4H), 1.50 (m, 2H), 1.36 (m, 2H), 0.85 (dd, J=7.34, 7.34 Hz, 3H). LCMS (ES+) m/z 463 (M+1).

7.11. Example 11

5-Butyl-1-(5-chloro-4-(thiophen-2-yl)pyrimidin-2-yl)-N-((1-methyl-1H-imidazol-5-yl)methyl)-1H-pyrazole-4-carboxamide (11). The title compound was prepared following the steps described in Example 1 with the exceptions of substituting 2,4,5-trichloropyrimidine for 2,4-dichloro-5-methylpyrimidine in Step 1 and substituting (1-methyl-1H-imidazol-2-yl)methanamine for pyridine-4-ylmethylamine in Step 5. $^1$H NMR 500 MHz (CDCl$_3$) δ 8.77 (d, J=4.17 Hz, 1H), 8.41 (dd, J=3.90, 0.935 Hz, 1H), 7.99 (s, 1H), 7.71 (dd, J=2.74, 0.91 Hz, 1H), 7.40 (s, 1H), 7.26 (d, J=5.91, 4.2 Hz, 1H), 6.94 (s, 1H), 6.83 (br s, 1H), 4.64 (d, J=4.0 Hz, 2H), 3.66 (s, 3H), 1.66 (m, 2H), 1.42 (m, 2H), 0.870 (dd, J=7.30, 7.30 Hz, 3H). LCMS (ES+) m/z 456 (M+1).

7.12. Example 12

5-Butyl-1-(5-chloro-4-(thiophen-2-yl)pyrimidin-2-yl)-N-((4-methyl-1H-imidazol-5-yl)methyl)-1H-pyrazole-4-carboxamide (12). The preparation of compound 12 was similar to that in Example 11 with the substitution of (4-methyl-1H-imidazol-2-yl)methanamine for (1-methyl-1H-imidazol-2-yl)methanamine in the final coupling step. $^1$H NMR 500 MHz (CDCl$_3$) δ 8.79 (s, 1H), 8.38 (d, J=3.83 Hz, 1H), 7.95 (s, 1H), 7.69 (d, J=5.01 Hz, 1H), 7.58 (s, 1H), 7.24 (dd, J=4.82, 4.02 Hz, 1H), 6.92 (br s, 1H), 4.51 (d, J=5.14 Hz, 2H), 3.61 (dd, J=7.76, 7.76 Hz, 2H), 2.30 (s, 3H), 1.2 (m, 2H), 1.37 (m, 2H), 0.859 (dd, J=7.31, 7.31 Hz, 3H); LCMS (ES+) m/z 456 (M+1).

7.13. Example 13

5-Butyl-1-(5-chloro-4-(thiophen-2-yl)pyrimidin-2-yl)-N-(6,7,8,9-tetrahydro-5H-[1,2,4]triazolo[4,3-a]azepin-9-yl)-1H-pyrazole-4-carboxamide (13). Compound 13 was prepared, with appropriate modification, to the procedure in Example 9. $^1$H NMR 400 MHz (CDCl$_3$) δ 8.79 (s, 1H), 8.38 (dd, J=3.90, 0.69 Hz, 1H), 8.12 (s, 1H), 8.10 (s, 1H), 7.79 (d, J=6.2 Hz, 1H), 7.68 (dd, J=5.0, 0.68 Hz, 1H), 7.24 (dd, J=4.81, 4.81 Hz, 1H), 5.26 (m, 1H), 4.33 (ABd, J$_{AB}$=14.2 Hz, J=4.37 Hz, 1H), 3.87 (dd, J=12.94, 12.94 Hz, 1H), 3.64 (m, 2H), 2.52 (m, 1H), 2.10-2.21 (m, 2H), 1.96 (m, 1H), 1.68 (m, 2H), 1.56 (m, 2H), 1.42 (m, 2H), 0.86 (dd, J=7.30, 7.30 Hz, 3H). LCMS (ES+) m/z 498 (M+1).

7.14. Example 14

5-Butyl-1-(4-chloro-5-methylpyrimidin-2-yl)-N-((1-methyl-1H-imidazol-5-yl)methyl)-1H-pyrazole-4-carboxamide (14). Following the steps shown in Scheme D (see Section 6.2.2), this example describes the preparation of 14, an exemplary intermediate corresponding to D.5 in Scheme D, to which a diversity of —W—R$^1$ groups can be attached to prepare compounds according to formula I.

Step 1. A solution of 2-chloro-5-methyl-4-(2-trimethylsilanyl-ethoxy)-pyrimidine (2.1 g, 8.6 mmol, prepared from 2-chloro-5-methylpyrimidine according to Lluis et al., (1998) *Tetrahedron Lett.* 39:1807-1810) in pyridine, was treated with anhydrous hydrazine (4 mL, 15 eq) at 100° C. for 1 hour. At the completion of the reaction, the solvents were removed and the residue was diluted with 100 mL EtOAc and washed with water (5 mL×3). The organic layer was dried over anhydrous sodium sulfate, filtered and concentrated to give D.2 (R$^2$=methyl) as a white solid (2.17 g, 100%). $^1$H NMR (CDCl$_3$) δ 0.10 (s, 9H), 1.12 (t, J=7.0 Hz, 2H), 2.01 (s, 3H), 3.90 (s, br, 2H), 4.42 (t, J=7.0 Hz, 2H), 6.00 (s, 1H), 7.90 (s, 1H).

Step 2. A solution of D.2 (R$^2$=methyl, R$^3$=H) (2.1 g, 8.6 mmol) in EtOH (20 mL) was treated with (Z)-methyl 2-((dimethylamino)methylene)-3-oxoheptanoate (1.93 g, 1.1 eq) and acetic acid (0.2 mL). The mixture was heated at 90° C. for 2 hours before being cooled back to room temperature. The reaction mixture was concentrated, and the crude product was purified by column chromatography on silica gel with 1:1 EtOAc/Hexane as an eluent to give D.3 a colorless oil, (3 g, 90%). $^1$H NMR (CDCl$_3$) δ 0.12 (s, 9H), 0.91 (t, J=7.2 Hz, 3H), 1.20 (t, J=8.0 Hz, 2H), 1.37-1.41 (m, 2H), 1.58-1.62 (m, 2H), 2.21 (s, 3H), 3.52 (t, J=7.8 Hz, 2H), 3.89 (s, 3H), 4.57 (t, J=8.0 Hz, 2H), 8.13 (s, 1H), 8.56 (s, 1H). LCMS (ES+) m/z 391 (M+1).

Step 3. A solution of D.3 (2.84 g, 7.3 mmol) in MeCN (35 mL) was treated with TBAF (8 mL, 1M in THF, 1.1 equiv.) at room temperature overnight. The solvent was removed under reduced pressure and the residue was partitioned between water and EtOAc. The water layer was extracted with EtOAc. The combined organic layers were washed with sodium carbonate, dried over sodium sulfate, filtered and concentrated to give colorless oil. The crude material was dissolved in MeOH (30 mL) and water (30 mL) and treated with LiOH (650 mg) at 50° C. overnight. Majority of the solvent was removed under reduced pressure. The water layer was first washed twice with CH$_2$Cl$_2$, and then neutralized to pH 3 with 3N HCl. The resulted solid was collected by filtration, washed with water and dried (D.4, 1.5 g, 74%). $^1$H NMR (DMSO-d$^6$) δ 0.82 (t, J=7.5 Hz, 3H), 1.23-1.27 (m, 2H), 1.45-1.50 (m, 2H), 2.02 (s, 3H), 8.01 (s, 1H), 8.05 (brs, 1H), 12.8 (brs, 1H). LCMS (ES+) m/z 277 (M+1).

Step 4. A mixture of D.4 (7.5 g, 27 mmol) and POCl$_3$ (50 mL) was heated to 100° C. for 2 hours. POCl$_3$ was removed under reduced pressure and the residue was treated with ice water. The resulted white solid was filtered, washed with water and dried in the air (D.5, 8.3 g, 100%). $^1$H NMR (CDCl$_3$) δ 0.99 (t, J=7.4 Hz, 3H), 1.47-1.53 (m, 2H), 1.68-

1.70 (m, 2H), 2.52 (s, 3H), 3.48 (t, J=8 Hz, 2H), 8.36 (s, 1H), 8.74 (s, 1H), 10.7 (s, br, 1H). LCMS (ES+) m/z 295 (M+1).

Step 5. A mixture of D.5 (R=methyl, $R^4$=n-butyl), (1-methyl-1H-imidazol-5-yl)methanamine and a tertiary amine base was stirred at r.t. for 30 min. The reaction mixture was taken up in EtOAc and washed with sodium bicarbonate solution, water and brine. The organic layer was dried over anhydrous sodium sulfated, filtered, and concentrated. The crude product was purified by chromatography on silica gel to give 14.

7.15. Example 15

5-Butyl-N-((1-methyl-1H-imidazol-5-yl)methyl)-1-(5-methyl-4-phenoxypyrimidin-2-yl)-1H-pyrazole-4-carboxamide (15). A solution of 14 (16 mg, 0.04 mmol) in 3 mL DMF was mixed with phenol (15 mg, 0.17 mmol) and NaH (3.0 mg, 60% mineral oil dispersion, 0.12 mmol. The reaction mixture was stirred for overnight. At the completion of reaction as indicated by LCMS, the mixture was concentrated and purified by HPLC (Capcell Pak $C_{18}$ column, gradient of 20% A: 80% B to 80% A: 20% B over 45 minutes; A=0.1% TFA in water, B=0.1% TFA in MeCN) to give a white solid as 15. $^1$H NMR (CDCl$_3$) δ 0.89-0.92 (t, 3H), 1.36-1.41 (m, 2H), 1.60-1.63 (m, 2H), 2.24 (s, 3H), 3.52-3.55 (m, 2H), 3.69 (s, 3H), 4.67-4.69 (d, 2H), 6.80-6.83 (m, 2H), 6.92-6.95 (m, 3H), 7.02 (s, 1H), 7.52 (s, 1H), 7.86 (s, 1H), 8.36 (s, 1H). LCMS (ES+) m/z 446 (M+1).

7.16. Example 16

5-Butyl-1-(4-ethoxy-5-methylpyrimidin-2-yl)-N-((1-methyl-1H-imidazol-5-yl)methyl)-1H-pyrazole-4-carboxamide (16). Compound 16 was prepared following procedures described for compound 15 with the exception of substituting phenol with ethanol. $^1$H NMR (CDCl$_3$) δ 0.88-0.91 (t, 3H), 1.35-1.39 (m, 2H), 1.44-1.47 (t, J=7.0 Hz, 3H), 1.60-1.63 (m, 2H), 2.20 (s, 3H), 3.49-3.52 (m, 2H), 3.66 (s, 3H), 4.48-4.52 (q, 2H), 4.64-4.65 (d, J=5.5 Hz, 2H), 7.02 (s, 1H), 7.47 (s, 1H), 7.83 (s, 1H), 8.33 (s, 1H). LCMS (ES+) m/z 398 (M+1).

7.17. Example 17

5-Butyl-1-(4-(ethylamino)-5-methylpyrimidin-2-yl)-N-((1-methyl-1H-imidazol-5-yl)methyl)-1H-pyrazole-4-carboxamide (17). To a solution of 14 (35 mg, 0.09 mmol) in 3 mL DMF was added EtNH$_2$ (0.14 mL, 2 M in THF, 0.27 mmol) and TEA (37 μL, 0.27 mmol). The mixture was stirred at room temperature for 2 hours. Solvent was removed under reduced pressure. The residue was taken up with ethyl acetate and was washed with brine. The organic layer was dried over sodium sulfate, filtered and concentrated. The residual material was purified by column chromatography on silica gel (eluents: MeOH/DCM, 0-15%) gave 17. $^1$H NMR (CDCl$_3$) δ 0.87-0.90 (t, 3H), 1.29-1.32 (t, 3H), 1.36-1.39 (m, 2H), 2.09 (s, 3H), 3.49-3.52 (m, 2H), 3.57-3.60 (m, 2H), 3.65 (s, 3H), 4.64-4.65 (d, 2H), 4.73 (s, 1H), 6.01 (t, 1H), 7.02 (s, 1H), 7.45 (s, 1H), 7.79 (s, 1H), 8.06 (s, 1H), LCMS (ES+) m/z 397 (M+1).

7.18. Example 18

5-Butyl-N-((1-methyl-1H-imidazol-5-yl)methyl)-1-(5-methyl-4-(piperidin-1-yl)pyrimidin-2-yl)-1H-pyrazole-4-carboxamide (18). The title compound was prepared following procedures described for Example 17 with the exception of substituting ethylamine with piperidine. $^1$H NMR (CDCl$_3$) δ 0.86-0.89 (t, 3H), 1.33-1.36 (m, 2H), 1.32-1.43 (m, 3H), 1.57-1.61 (m, 2H), 2.27 (s, 3H), 3.09-3.13 (q, J=7.5 Hz, 3H), 3.46-3.50 (m, 6H), 3.75 (s, 1H), 4.63-4.64 (d, 2H), 6.84 (s, 1H), 7.12 (s, 1H), 7.85 (s, 1H), 7.97 (s, 1H), 8.16 (s, 1H). LCMS (ES+) m/z 437 (M+1).

7.19. Example 19

5-Butyl-1-(4-(cyclopropylamino)-5-methylpyrimidin-2-yl)-N-((1-methyl-1H-imidazol-5-yl)methyl)-1H-pyrazole-4-carboxamide (19). Compound 19 was prepared following procedures described in Example 17 with the exception of substituting ethylamine with cyclopropylamine. $^1$H NMR (CDCl$_3$) δ 0.65 (m, 2H), 0.87-0.93 (t, 3H), 1.35-1.37 (m, 2H), 1.43-1.46 (m, 3H), 1.63-1.64 (m, 2H), 2.10 (s, 3H), 2.93-2.95 (s, 1H), 3.12-3.22 (m, 3H), 3.67-3.70 (m, 2H), 3.70-3.72 (s, 3H), 4.67 (s, 2H), 5.11 (s, 1H), 6.67 (s, 1H), 7.09 (s, 1H), 7.67 (s, 1H), 7.96 (s, 1H), 8.10 (s, 1H), LCMS (ES+) m/z 409 (M+1).

7.20. Example 20

1-(4-(1H-Imidazol-1-yl)-5-methylpyrimidin-2-yl)-5-butyl-N-((1-methyl-1H-imidazol-5-yl)methyl)-1H-pyrazole-4-carboxamide (20). The title compound was prepared following procedures described in Example 17 with the exception of substituting ethylamine with imidazole. $^1$H NMR (CDCl$_3$) δ 0.92-0.95 (m, 3H), 1.41-1.46 (m, 2H), 2.63 (s, 3H), 3.56-3.58 (t, 2H), 3.73 (s, 3H), 4.70-4.71 (t, 2H), 6.10-6.11 (s, 1H), 7.09 (s, 1H), 7.54 (s, 1H), 7.69 (s, 1H), 7.94 (s, 1H), 8.30 (s, 1H), 8.85 (s, 1H). LCMS (ES+) m/z 420 (M+1).

7.21. Example 21

5-Butyl-1-(4-cyclobutyl-5-methylpyrimidin-2-yl)-N-((1-methyl-1H-imidazol-5-yl)methyl)-1H-pyrazole-4-carboxamide (21). To the suspension of fine-grinded Mg powder (36 mg, 1.5 mmol) over 2 mL anhydrous ether, bromocyclobutane (95 μL, 1.0 mmol) was dropped in closely to the Mg. After the Mg powder dissolved, ZnCl$_2$ (204 mg, 1.5 mmol) and the chloro intermediate 14 (40 mg, 0.10 mmol) were added to the solution followed with Pd(dppf)Cl$_2$ (7.31 mg, 0.01 mmol). The reaction mixture was then heated to 70° C. overnight. After removal of the solvent, the residue was partitioned between ethyl acetate and brine. The organic layer was dried over sodium sulfate, filtered, concentrated and purified by HPLC (Capcell Pak $C_{18}$ column, gradient of 20% A: 80% B to 80% A: 20% B over 45 minutes; A=0.1% TFA in water, B=0.1% TFA in MeCN) to give a white solid as compound 21. $^1$H NMR (CDCl$_3$) δ 0.93-0.95 (m, 3H), 1.443-1.45 (m, 4H), 1.61-1.63 (m, 2H), 2.34-2.35 (m, 1H), 2.44 (s, 1H), 2.57 (m, 2H), 3.50-3.52 (m, 2H), 4.12 (s, 3H), 4.68-4.76 (m, 6H), 7.56 (s, 1H), 8.70-8.85 (m, 2H), 9.23-9.26 (m, 1H). LCMS (ES+) m/z 408 (M+1).

7.22. Example 22

(5-Butyl-1-(5-chloro-4-cyclopentylpyrimidin-2-yl)-N-6,7,8,9-tetrahydro-5H-[1,2,4]triazolo[4,3-a]azepin-9-yl)-1H-pyrazole-4-carboxamide (22). Prepared similarly following reaction sequence and conditions described for compounds in Examples 12 and 21. $^1$H NMR 400 MHz (CDCl$_3$) δ 8.69 (s, 1H), 8.09 (s, 1H), 8.08 (s, 1H), 7.73 (s, 1H), 5.24 (br s, 1H), 4.30 (AB, $J_{AB}$=13.7 Hz, 1H), 3.85 (dd, J=12.9, 12.9 Hz, 1H), 3.51-3.72 (m, 4H), 1.24-2.51 (m, 17H), 0.875 (dd, J=7.1, 7.1 Hz, 3H). LCMS (ES+) m/z 483 (M+1).

7.23. Example 23

This example illustrates the preparation of (5-butyl-1-(5-methyl-4-(thiophen-2-yl)pyrimidin-2-yl)-1H-pyrazol-4-yl)methanol (23) useful as an intermediate. To a sample of methyl 5-(methoxymethyl)-1-(5-methyl-4-(thiophen-2-yl)pyrimidin-2-yl)-1H-pyrazole-4-carboxylate (1.0 g, 2.8 mmol), prepared as described in Example 1, in 50 mL of $CH_2Cl_2$, cooled to −78° C. was added 11.2 mL of DIBAL (1 M in THF, 11.2 mmol). The mixture was stirred at −78° C. for 3 hours. The reaction was then slowly warmed to room temperature. After 3 hours the reaction was quenched with 10 mL of MeOH and air was bubbled through the solution for 3 hours. The reaction mixture was partitioned between water and $CH_2Cl_2$, the organic layer was then concentrated and the crude mixture was purified by normal phase chromatograph on silica (19:1 $CH_2Cl_2$/MeOH) to provide 600 mg of 23 as a light yellow solid. $^1$H NMR (400 MHz, CDCl$_3$) δ 0.87 (t, J=7.1 Hz, 3H), 1.37 (m, 2H), 1.40 (m, 2H), 2.6 (s, 3H), 3.36 (t, J=7.3 Hz, 2H), 4.6 (s, 2H), 7.28 (m, 1H), 7.62 (d, J=4.6 Hz, 1H), 7.73 (s, 1H) 7.81 (s 1H), 8.66 (s, 1H). LCMS (ES+) m/z 329 (M+1).

7.24. Example 24

2-(5-Butyl-4-(((1,4-dimethyl-1H-imidazol-5-yl)methoxy)methyl)-1H-pyrazol-1-yl)-5-methyl-4-(thiophen-2-yl)pyrimidine (24). To a 20 mL vial was added alcohol 23 (1.0 g, 3.1 mmol) and 10 mL of POCl$_3$. The reaction was stirred at 70° C. for 4 hours at which time the excess POCl$_3$ was blown off with a stream of nitrogen. The crude material was partitioned between water and $CH_2Cl_2$, the organic layer dried with sodium sulfate and concentrated to provide 1 g of the semi crude intermediate 2-(5-butyl-4-(chloromethyl)-1H-pyrazol-1-yl)-5-methyl-4-(thiophen-2-yl)pyrimidine as a brown oil.

To a 20 mL vial was added (1,4-dimethyl-1H-imidazol-5-yl)methanol (32 mg, 0.26 mmol), NaH (10 mg, 60% in oil, 0.12 mmol) and 4 mL of DMF. The reaction mixture was stirred at room temperature for 30 minutes, at which time the reaction was cooled to 0° C., the crude intermediate 2-(5-butyl-4-(chloromethyl)-1H-pyrazol-1-yl)-5-methyl-4-(thiophen-2-yl)pyrimidine (60 mg, 0.17 mmol) was added, warmed to room temperature and stirred for an additional 2 hours. The crude reaction was partitioned between water and EtOAc, the organic layer was concentrated and was purified by reverse phase preparative HPLC to provide 1.4 mg of 24 as a clear film. $^1$H NMR (400 MHz, MeOD-d$_3$) δ 0.851 (t, J=5.9 Hz, 3H), 1.35 (q, J=5.9 Hz, 2H), 1.57 (t, J=6.2 Hz, 2H), 2.38 (s, 3H), 2.67 (s, 3H), 3.35 (t, J=4.8 Hz, 2H), 3.91 (s, 3H), 4.61 (s, 2H), 4.67 (s, 2H) 7.31 (t, J=3.6 Hz, 1H), 7.76 (s, 1H), 7.78 (d, J=4.1 Hz, 1H), 7.96 (d, J=3.1 Hz, 1H), 8.71 (s, 1H), 8.81 (s, 1H). LCMS (ES+) m/z 437 (M+1).

7.25. Example 25

2-(5-Butyl-4-((pyridin-4-yloxy)methyl)-1H-pyrazol-1-yl)-5-methyl-4-(thiophen-2-yl)pyrimidine (25). To a 20 mL vial was added alcohol 23 (100 mg, 0.30 mmol), 4-hydroxypyrdine (57 mg, 0.6 mmol), DEAD (105 mg, 0.6 mmol), PPh$_3$ (157 mg, 0.6 mmol), 5 mL THF and TEA (64 μL, 0.46 mmol). The reaction was stirred at room temperature for 6 hours, at which time the reaction mixture was partitioned between water and EtOAc. The organic layer was then concentrated and the crude mixture was purified first by reverse phase preparative HPLC and then by normal phase chromatography on silica (9:1 $CH_2Cl_2$/MeOH+1% NH$_4$OH) to provide 5.0 mg of 25 as an off white solid. $^1$H NMR (400 MHz, CDCl$_3$) δ 0.85 (t, J=7.3 Hz, 3H), 1.35 (q, J=7.6 Hz, 2H), 1.62 (t, J=7.1 Hz, 2H), 2.64 (s, 3H), 3.35 (t, J=7.2 Hz, 2H), 5.05 (s, 2H), 6.92 (d, J=5.1 Hz, 2H), 7.25 (m, 1H), 7.63 (d, J=4.7 Hz, 1H), 7.82 (m, 2H), 8.49 (d, J=4.7 Hz, 2H), 8.67 (s, 1H). LCMS (ES+) m/z 406 (M+1).

7.26. Example 26

4-((5-Butyl-1-(5-methyl-4-(thiophen-2-yl)pyrimidin-2-yl)-1H-pyrazol-4-yl)methoxy)quinoline (26). To a 20 mL vial was added DEAD (105 mg, 0.6 mmol), PPh$_3$ (157 mg, 0.6 mmol) 5 mL THF and TEA (64 μL, 0.46 mmol). The mixture was stirred for 30 minutes then alcohol 23 (100 mg, 0.30 mmol) and 8-hydroxyisoquinoline (87 mg, 0.6 mmol) were added. The reaction was stirred at room temperature for 6 hours, at which time the reaction mixture was partitioned between water and EtOAc. The organic layer was then concentrated and the crude mixture was purified first by reverse phase preparative HPLC to provide 12.0 mg of 26 as an off white solid. $^1$H NMR (400 MHz, CDCl$_3$) δ 0.78 (t, J=7.2 Hz, 3H), 1.35 (m, 2H), 1.62 (m, 2H), 2.64 (s, 3H), 3.38 (t, J=7.6 Hz, 2H), 5.26 (s, 2H), 7.25 (dd, J=5.0, 4.0 Hz, 1H), 7.55 (dd, J=6.6, 1.9 Hz, 1H), 7.63 (dd, J=5.1, 0.8 Hz, 1H), 7.83 (dd, J=3.9, 1.1 Hz, 1H), 7.89 (m, 3H), 8.52 (s, 2H), 8.67 (s, 1H), 9.66 (s, 1H). LCMS (ES+) m/z 456 (M+1).

7.27. Example 27

5-Butyl-1-(5-methyl-4-(thiazol-5-yl)pyrimidin-2-yl)-N-((4-methyl-4H-1,2,4-triazol-3-yl)methyl)-1H-pyrazole-4-carboxamide (27). Compound 27 was prepared from 5-butyl-1-(5-methyl-4-(thiazol-5-yl)pyrimidin-2-yl)-1H-pyrazole-4-carboxylic acid following procedures described in Example 1 with the exceptions of substituting thiophene-2-boronic acid with thiazole-5-boronic acid in Step 1 and substituting pyridine-4-ylmethylamine with (4-methyl-4H-1,2,4-triazol-3-yl)methanamine. $^1$H NMR (400 MHz, MeOD-d$_3$) δ 0.85 (t, J=7.3 Hz, 3H), 1.36 (m, 2H), 1.61 (m, 2H), 2.69 (s, 3H), 3.56 (t, J=7.4 Hz, 2H), 3.97 (s, 3H), 4.81 (s, 2H), 7.63 (s, 1H), 8.15 (s, 1H), 8.61 (s, 1H), 8.81 (s, 1H), 8.98 (s, 1H), 9.17 (s, 1H). LCMS (ES+) m/z 438 (M+1).

7.28. Example 28

5-Butyl-N-((4-methyl-1H-imidazol-5-yl)methyl)-1-(5-methyl-4-(thiazol-5-yl)pyrimidin-2-yl)-1H-pyrazole-4-carboxamide (28). A solution of 5-butyl-1-(5-methyl-4-(thiazol-5-yl)pyrimidin-2-yl)-1H-pyrazole-4-carboxylic acid (80 mg, 0.24 mmol), (4-methyl-1H-imidazol-5-yl)methanamine (72 mg, 0.48 mmol), HBTU (182 mg, 0.48 mmole) and 2 mL of DMF was prepared to which DIEA (167 μL, 0.96 mmol) was added. The reaction was stirred at 50° C. for 3 hours at which time the crude mixture was purified directly by reverse phase preparative HPLC to provide 21.1 mg of 28 as a white solid. $^1$H NMR (400 MHz, MeOD-d$_3$) δ 0.84 (t, J=3.4 Hz, 3H), 1.33 (q, J=7.5 Hz, 2H), 1.59 (t, J=6.6 Hz, 2H), 2.67 (s, 3H), 2.97 (s, 3H), 3.43 (s, 2H), 3.56 (t, J=7.7 Hz, 2H), 7.47 (s, 1 H), 8.07 (s, 1H), 8.58 (s, 1H), 8.77 (s, 1H), 9.12 (s, 1H). LCMS (ES+) m/z 437 (M+1).

7.29. Example 29

N-(2-(2-Amino-4-methylthiazol-5-yl)ethyl)-5-butyl-1-(5-methyl-4-(thiophen-2-yl)pyrimidin-2-yl)-1H-pyrazole-4-carboxamide (29). A solution of 5-butyl-1-(5-methyl-4-(thiazol-5-yl)pyrimidin-2-yl)-1H-pyrazole-4-carboxylic acid (45 mg, 0.13 mmol), 5-(2-aminoethyl)-4-methylthiazol-2-amine (50 mg, 0.16 mmol), HBTU (197 mg, 0.20 mmol), and 2 mL of DMF was prepared to which DIEA (68 µL, 0.39 mmol) was added. The reaction was stirred at room temperature for 4 hours at which time the crude mixture was purified directly by reverse phase preparative HPLC to provide 31.2 mg of 29 as a white solid. $^1$H NMR (400 MHz, MeOD-d$_3$) δ 0.84 (t, J=7.2 Hz, 3H), 1.35 (m, 2H), 1.61 (m, 2H), 2.20 (s, 3H), 3.27 (s, 3H), 2.90 (t, J=6.5 Hz, 2H), 3.54 (t, J=6.7 Hz, 2H), 3.60 (t, J=7.9 Hz, 2H), 7.29 (t, J=4.5 Hz, 1H), 7.40 (s, 1H), 7.73 (d, J=5.1 Hz, 1H), 7.92 (d, J=3.5 Hz, 1H), 8.04 (s, 1H), 8.71 (s, 1H). LCMS (ES+) m/z 482 (M+1).

7.30. Example 30

(5-Butyl-1-(5-methyl-4-(thiophen-2-yl)pyrimidin-2-yl)-1H-pyrazol-4-yl)(5,6-dihydro-[1,2,4]triazolo[4,3-a]pyrazin-7(8H)-yl)methanone (30). To a solution of 5-butyl-1-(5-methyl-4-(thiazol-5-yl)pyrimidin-2-yl)-1H-pyrazole-4-carboxylic acid (72 mg, 0.21 mmol), 5,6,7,8-tetrahydro-[1,2,4]triazolo[4,3-a]pyrazine (50 mg, 0.23 mmol), HBTU (119 mg, 0.32 mmol) and 4 mL of DMF was added DIEA (54 µL, 0.73 mmol). The reaction was stirred at room temperature for 2 hours at which time the crude mixture was purified directly by reverse phase preparative HPLC to provide 3.0 mg of 30 as a white solid. $^1$H NMR (400 MHz, MeOD-d$_3$) δ 0.78 (t, J=7.2 Hz, 3H), 1.35 (m, 2H), 1.61 (m, 2 H), 2.69 (s, 3H), 3.4 (t, J=7.7 Hz, 2H), 4.18 (t, J=5.1 Hz, 2H), 4.31 (t, J=5.5 Hz, 2H), 5.10 (s, 2H), 7.32 (t, J=4.5 Hz, 1H), 7.82 (d, J=5.1 Hz, 1H), 7.96 (s, 1H), 7.99 (d, J=2.7 Hz, 1H), 8.54 (s, 1H), 8.76 (s, 1H). LCMS (ES+) m/z 449 (M+1).

7.31. Example 31

N-(4-(1H-Imidazol-1-yl)phenyl)-5-butyl-1-(5-methyl-4-(thiophen-2-yl)pyrimidin-2-yl)-1H-pyrazole-4-carboxamide (31). Compound 31 was prepared following procedures described in Example 1 by replacing 3-methoxypropylamine with 4-(1H-imidazol-1-yl)benzenamine. $^1$H NMR (500 MHz, DMSO-d6) δ 10.11 (s, 1H), 8.89 (s, 1H), 8.38 (s, 1H), 8.22 (s, 1H), 7.98 (m, 2H), 7.90 (dd, J=8.80, 2.69 Hz, 2H), 7.73 (s, 1H), 7.65 (d, J=8.80 Hz, 2H), 7.35 (dd, J=5.13, 4.40 Hz, 1H), 7.12 (s, 1H), 3.43 (t, J=7.83 Hz, 2H), 2.65 (s, 3H), 1.56 (quint, J=7.58 Hz, 2H), 1.27 (sex, J=7.34 Hz, 2H), 0.80 (t, J=7.34 Hz, 3H). LCMS (ESI) m/z 484 (M+H) (M+1).

7.32. Example 32

5-Butyl-1-(5-methyl-4-(thiophen-2-yl)pyrimidin-2-yl)-N-((6-oxopiperidin-3-yl)methyl)-1H-pyrazole-4-carboxamide (32). Compound 32 was prepared following procedures described in Example 1 by replacing 3-methoxypropylamine with 5-(aminomethyl)piperidin-2-one. $^1$H NMR (400 MHz, CD$_3$OD) δ 8.76 (s, 1H), 8.16 (s, 1H), 7.99 (d, J=3.87 Hz, 1H), 7.82 (d, J=4.39 Hz, 1H), 7.43 (d, J=6.78 Hz, 1H), 7.32 (dd, J=5.06, 3.92 Hz, 1H), 6.51 (s, 1H), 6.45 (dd, J=6.78, 1.49 Hz, 1H), 4.51 (s, 2H), 3.60 (t, J=7.76 Hz, 2H), 2.69 (s, 3H), 1.61 (sept, J=7.50 Hz, 2H), 1.34 (sex, J=7.42 Hz, 2H), 0.85 (t, J=7.40 Hz, 3H). LCMS (ESI) m/z 449.2 (M+1).

7.33. Example 33

Pyridin-4-ylmethyl 5-butyl-1-(5-methyl-4-(thiophen-2-yl)pyrimidin-2-yl)-1H-pyrazole-4-carboxylate (33). Compound 33 was prepared following procedures described in Example 1 by replacing 3-methoxypropylamine with pyridin-4-ylmethanol. $^1$H NMR (500 MHz, CD$_3$OD) δ 8.86 (m 3H), 8.30 (bs, 1H), 8.13 (d, J=6.36 Hz, 2H), 1.98 (d, J=3.91 Hz, 1H), 7.82 (d, J=3.42 Hz, 1H), 7.32 (dd, J=4.89, 3.91 Hz, 1H), 5.68 (s, 2H), 3.58 (t, J=7.82 Hz, 2H), 2.69 (s, 3H), 1.67 (quint, J=7.83 Hz, 2H), 1.37 (sex, J=7.34 Hz, 2H), 0.86 (t, J=7.34 Hz, 3H). LCMS (ES+) m/z 434 (M+1).

7.34. Example 34

N-((5-Butyl-1-(5-methyl-4-(thiophen-2-yl)pyrimidin-2-yl)-1H-pyrazol-4-yl)methyl)-2-(1H-imidazol-5-yl)acetamide (34). Compound 34 was prepared in a fourstep synthesis.

Step 1. A solution of alcohol 23 (945 mg, 2.88 mmol, 1 equiv) in POCl$_3$ (15 mL) was heated to 70° C. and let stir for 7 h. Excess reagent was removed to afford 2-(5-butyl-4-(chloromethyl)-1H-pyrazol-1-yl)-5-methyl-4-(thiophen-2-yl)pyrimidine (870 mg, 87%), which was taken to the next step without further purification.

Step 2. To a solution of 2-(5-butyl-4-(chloromethyl)-1H-pyrazol-1-yl)-5-methyl-4-(thiophen-2-yl)pyrimidine (870 mg, 2.52 mmol, 1 equiv) in DMF (15 mL) was added NaN$_3$ (212 mg, 3.26 mmol, 1.2 equiv) and heated to 85° C. and let stir for 2 h. The reaction was diluted with H$_2$O (50 mL) and extracted with ethyl acetate (3×75 mL). The organic layer was combined, dried (over magnesium sulfate), concentrated and taken crude to the next step.

Step 3. The mixture of crude product from Step 2 and Pd/C (10%, 10 mg) in MeOH (15 mL) was charged with hydrogen gas (1 atm). After being stirred for 3.5 h at 44° C., the reaction mixture was filtered through a Celite pad and concentrated. The crude product was purified by silica gel flash column chromatography (10% methanol in dichloromethane with 1% ammonium hydroxide) to afford (5-butyl-1-(5-methyl-4-(thiophen-2-yl)pyrimidin-2-yl)-1H-pyrazol-4-yl)methanamine (730 mg, 90% yield) as a yellow solid. $^1$H NMR (500 MHz, CD$_3$OD) δ 8.59 (s 1H), 7.86 (d, J=3.42 Hz, 1H), 7.80 (s 1H), 7.73 (d, J=4.89 Hz, 1H), 7.24 (dd, J=5.13, 3.91 Hz, 1H), 3.72 (t, J=7.58 Hz, 2H), 2.56 (s 3H), 1.51 (quint, J=7.34 Hz, 2H), 1.34 (sex, J=7.58 Hz, 2H), 0.84 (t, J=7.34 Hz, 3H); LRMS (ESI) m/z: Calcd for C$_{17}$H$_{21}$N$_5$S (free base; M+H) 328.2. found 328.3.

Step 4. A mixture of (5-butyl-1-(5-methyl-4-(thiophen-2-yl)pyrimidin-2-yl)-1H-pyrazol-4-yl)methanamine and 2-(1H-imidazol-5-yl)acetic acid in 1:1 molar ratio was treated with EDC (1 equiv.), HOBT (1 equiv.) and N-methylmorpholine (2 equiv.) in methylene chloride (at a concentration of 0.5 M) at room temperature overnight (20 hours). Upon completion, an additional methylene chloride was added and the resulting mixture was washed with water and brine, dried over anhydrous sodium sulfate and concentrated. The crude material was purified by column chromatography using 10% CH$_3$OH/CH$_2$Cl$_2$ as the eluent to give the title compound 34. $^1$H NMR (400 MHz, CD$_3$OD) δ 8.79 (s 1H), 8.34 (t, J=5.48 Hz, 1H), 8.10 (s 1H), 7.94 (s 1H), 7.93 (s 1H), 7.62 (s 1H), 7.33 (D, J=4.69 Hz, 1H), 7.10 (s 1H), 4.18 (D, J=5.48 Hz, 2H), 3.49 (s 3H), 3.11 (t, J=7.83 Hz, 2H), 2.60 (s 3H), 1.40 (quint, J=7.43 Hz, 2H), 1.24 (sex, J=7.83 Hz, 2H), 0.77 (t, J=7.43 Hz, 3H). LCMS (ES+) m/z 436 (M+1).

7.35. Example 35

N-(5-Butyl-1-(5-methyl-4-(thiophen-2-yl)pyrimidin-2-yl)-1H-pyrazol-4-yl)-2-(pyridin-4-yl)acetamide (35). The following describes a three-step synthesis of 35.

Step 1. To a solution of 5-butyl-1-(5-methyl-4-(thiophen-2-yl)pyrimidin-2-yl)-1H-pyrazole-4-carboxylic acid (1.03 g, 3.01 mmol) and TEA (461 µL, 3.31 mmol, 1.1 equiv.) in toluene (15 mL) was injected DPPA (680 µL, 3.16 mmol, 1.05 equiv.). The mixture was heated to 90~100° C. and let stir for 1.5 h. When bubbling had ceased, t-butanol (1.0 mL, 10.66 mmol, 3.54 equiv) was injected and stirred for 17 h. The reaction was then evaporated and the resulting oil was subjected to silica gel flash column chromatography (gradient of 80% ethyl acetate in hexanes to 100% ethyl acetate) to afford protected amine intermediary tert-butyl 5-butyl-1-(5-methyl-4-(thiophen-2-yl)pyrimidin-2-yl)-1H-pyrazol-4-ylcarbamate as a white solid. $^1$H NMR (500 MHz, CD$_3$OD) δ 8.77 (s, 1H), 8.68 (bs, 1H), 7.92 (s, 2H), 7.74 (bs, 1H), 7.31 (m, 1H), 3.09 (t, J=7.83 Hz, 2H), 2.57 (s, 3H), 1.46 (s, 9H), 1.38 (m, 2H), 1.22 (m, 2H), 0.76 (t, J=7.34 Hz, 3H). LCMS (ES+) m/z 414 (M+1).

Step 2. To the solution of tert-butyl 5-butyl-1-(5-methyl-4-(thiophen-2-yl)pyrimidin-2-yl)-1H-pyrazol-4-ylcarbamate from step 1 in CHCl$_3$ (30 mL) cooled to 0° C. was injected trifluoroacetic acid (3 mL) and let stir for 23 h at 23° C. The reaction solvent was then evaporated and redissolved in CH$_2$Cl$_2$ and washed with saturated NaHCO$_3$ solution. The organic layer dried (sodium sulfate) and concentrated, whereupon the residue was purified by silica gel flash column chromatography (gradient from 2% methanol in dichloromethane to 10% methanol in dichloromethane) afford 5-butyl-1-(5-methyl-4-(thiophen-2-yl)pyrimidin-2-yl)-1H-pyrazol-4-amine (361 mg, 38% yield over 3 steps) as a yellow oil. $^1$H NMR (500 MHz, DMSO) δ 8.55 (s, 1H), 7.83 (dd, J=3.91, 0.98 Hz, 1H), 7.69 (dd, J=5.38, 0.98 Hz, 1H), 7.46 (s, 1H), 7.21 (dd, J=4.89, 3.91 Hz, 1H), 4.86 (bs, 2H), 3.19 (t, J=7.82 Hz, 2H), 2.53 (s, 3H), 4.53 (m, 2H), 1.36 (sex, J=7.83 Hz, 2H), 0.84 (t, J=7.34 Hz, 3H). LCMS (ES+) m/z 314 (M+1).

Step 3. To a solution of 5-butyl-1-(5-methyl-4-(thiophen-2-yl)pyrimidin-2-yl)-1H-pyrazol-4-amine (51 mg, 0.163 mmol, 1.0 equiv) and 2-(pyridin-4-yl)acetic acid (56 mg, 0.323 mmol, 2.0 equiv) in DMF (1 mL) was added HBTU (51 mg, 0.179 mmol, 1.1 equiv) and DIEA (91 µL, 0.520 mmol, 3.2 equiv) and heated to 40° C. and let stir for 15 h. The reaction was diluted with saturated NaHCO$_3$ solution (15 mL) and extracted with a solution of 30% IPA in CHCl$_3$ (3×20 mL). The organic layer dried (sodium sulfate), concentrated, and the residue was purified by silica gel flash column chromatography (10% methanol in dichloromethane) afford 35 (45 mg, 64% yield) as an off-white amorphous solid. $^1$H NMR (400 MHz, CD$_3$OD) δ 8.65 (s 1H), 8.51 (d, J=5.6 Hz, 2H), 7.91 (d, J=4.4 Hz, 2H), 7.75 (d, J=5.2 Hz, 1H), 7.48 (d, J=5.6 Hz, 2H), 7.27 (t, J=4.0 Hz, 1H), 3.83 (s, 2H), 3.22 (t, J=7.6 Hz, 2H), 2.60 (s, 3H), 1.48 (quint, J=7.6 Hz, 2H), 1.25 (sex, J=7.2 Hz, 2H), 0.77 (t, J=7.2 Hz, 3H). LCMS (ES+) m/z 433 (M+1).

7.36. Example 36

Pyridin-4-ylmethyl 5-butyl-1-(5-methyl-4-(thiophen-2-yl)pyrimidin-2-yl)-1H-pyrazol-4-ylcarbamate (36). Compound 36 was prepared following procedures described in step 1 for compound in Example 35 with the exception of substituting t-butanol with pyridin-4-ylmethanol. $^1$H NMR (500 MHz, CD$_3$OD) δ 8.60 (s, 1H), 8.54 (d, J=4.9 Hz, 2H), 7.86 (d, J=6.9 Hz, 2H), 7.72 (d, J=4.9 Hz, 1H), 7.48 (m, 2H), 7.23 (t, J=4.9 Hz, 1H), 5.28 (s, 2H), 3.22 (t, J=7.8 Hz, 2H), 2.55 (s, 3H), 1.5 (quint, J=7.3 Hz, 2H), 1.31 (sex, J=7.3 Hz, 2H), 0.80 (t, J=7.3 Hz, 3H). LCMS (ES+) m/z 449 (M+1).

7.37. Example 37

N-((5-Butyl-1-(5-methyl-4-(thiophen-2-yl)pyrimidin-2-yl)-1H-pyrazol-4-yl)methyl)-1,2-dimethyl-1H-imidazole-5-sulfonamide (37). The title compound was prepared by mixing a sample of (5-butyl-1-(5-methyl-4-(thiophen-2-yl)pyrimidin-2-yl)-1H-pyrazol-4-yl)methanamine, (from Step 3 of Example 36), 1,2-dimethyl-1H-imidazole-5-sulfonyl chloride and diisopropylethylamine in dichloromethane. $^1$H NMR (400 MHz, CD$_3$OD) δ 8.68 (s 1H), 7.94 (m, 1H), 7.78 (m, 1H), 7.56 (m, 1H), 7.37 (m, 1H), 7.29 (m, 1H), 4.09 (s 2H), 3.70 (s 3H), 3.18 (br t, 2H), 2.64 (s, 3H), 2.35 (s, 3H), 1.49 (m, 2H), 1.32 (m, 2H), 0.84 (m 3H). LCMS (ES+) m/z 486 (M+1).

7.38. Example 38

5-Butyl-1-(5-fluoro-4-(thiophen-2-yl)pyrimidin-2-yl)-N-(1-(4-methyl-4H-1,2,4-triazol-3-yl)cyclopropyl)-1H-pyrazole-4-carboxamide (38). Compound 38 was synthesized following procedures described in Example 1 with the exceptions of starting with 2,4-dicholoro-5-fluoropyrimidine instead of 2,4-dicholoro-5-methylpyrimidine in Step 1 and substituting 1-(4-methyl-4H-1,2,4-triazol-3-yl)cyclopropanamine for pyridine-4-ylmethylamine in Step 5. $^1$H NMR (500 MHz, CD$_3$OD) δ 8.98 (s, 1H), 8.86 (d, J=2.93 Hz, 1H), 8.15 (m, 2H), 7.92 (d, J=4.89, 0.73 Hz, 1H), 7.34 (dd, J=5.14, 3.91 Hz, 1H), 4.05 (s, 3H), 3.48 (m, 2H), 1.68 (dd, J=7.83, 5.14 Hz, 2H), 1.62 (m, 2H), 1.56 (dd, J=7.83, 5.62 Hz, 2H), 1.36 (sex, J=7.34 Hz, 2H), 0.87 (t, J=7.34 Hz, 3H). LCMS (ES+) m/z 467 (M+1).

7.39. Examples 39-97

The following examples were synthesized with slight modifications to the synthetic procedures described above.

5-(But-3-enyl)-N-((1-methyl-1H-imidazol-5-yl)methyl)-1-(5-methyl-4-(thiophen-2-yl)pyrimidin-2-yl)-1H-pyrazole-4-carboxamide (39). LCMS (ES+) m/z 434 (M+1).

5-Butyl-N-(1-methyl-1H-benzo[d]imidazol-7-yl)-1-(5-methyl-4-(thiophen-2-yl)pyrimidin-2-yl)-1H-pyrazole-4-carboxamide (40). $^1$H NMR (400 MHz, CD$_3$OD) δ 8.77 (s, 1H), 8.35 (s, 1H), 8.09 (s, 1H), 7.99 (d, J=3.52 Hz, 1H), 7.81 (d, J=5.08 Hz, 1H), 7.66 (d, J=8.21 Hz, 1H), 7.36-7.27 (m, 2H), 7.21 (d, J=7.43 Hz, 1H), 4.00 (s, 3H), 3.61 (t, J=7.83 Hz, 2H), 2.68 (s, 3H), 1.70-1.66 (m, 2H), 1.41-1.27 (m, 2H), 0.83 (t, J=7.43 Hz, 3H). LCMS (ES+) m/z 472 (M+1).

5-Butyl-N-(4,5,6,7-tetrahydro-1-methyl-1H-benzo[d] imidazol-7-yl)-1-(5-methyl-4-(thiophen-2-yl)pyrimidin-2-yl)-1H-pyrazole-4-carboxamide (41).

5-Butyl-1-(5-methyl-4-(thiophen-2-yl)pyrimidin-2-yl)-N-((thiazol-5-yl)methyl)-1H-pyrazole-4-carboxamide (42). $^1$H NMR (DMSO-d$^6$) δ 0.76 (t, J=7.0 Hz, 3H), 1.19-1.23 (m, 2H), 1.47-1.49 (m, 2H), 2.60 (s, 3H), 3.38 (t, J=7.5 Hz, 2H), 4.65 (d, J=5.5 Hz, 2H), 7.32 (t, J=4.5 Hz, 1H), 7.82 (s, 1H), 7.95 (d, J=4.5 Hz, 2H), 8.12 (s, 1H), 8.84 (s, 1H), 8.88 (t, J=5.5 Hz, 1H), 8.98 (s, 1H). LCMS (ES+) m/z 439 (M+1).

5-Butyl-1-(5-chloro-4-(thiophen-2-yl)pyrimidin-2-yl)-N-((thiazol-5-yl)methyl)-1H-pyrazole-4-carboxamide (43). $^1$H NMR (400 MHz, CD$_3$OD) δ 8.94 (s, 1H), 8.92 (s, 1H), 8.45 (d, J=3.91 Hz, 1H), 7.86 (m, 1H), 7.67 (s, 1H), 7.30 (t, J=4.3 Hz, 1H), 5.08 (t, J=7.87 Hz, 2H), 4.78 (s, 3H), 1.77 (quint, J=7.43 Hz, 2H), 1.32 (sex, J=7.43 Hz, 2H), 0.87 (t, J=7.43 Hz, 3H). LCMS (ES+) m/z 459 (M+1).

5-Butyl-N-(sulfolan-3-yl)-1-(5-methyl-4-(thiophen-2-yl) pyrimidin-2-yl)-1H-pyrazole-4-carboxamide (44).

(5-Butyl-1-(5-methyl-4-(thiophen-2-yl)pyrimidin-2-yl)-1H-pyrazol-4-yl)(6,7-dihydro-3-hydroxyisoxazolo[4,5-c] pyridin-5(4H)-yl)methanone (45).

2-(5-Butyl-4-((E)-3-(1-methyl-1H-imidazol-5-yl)prop-1-enyl)-1H-pyrazol-1-yl)-5-chloro-4-(thiophen-2-yl)pyrimidine (46). LCMS (ES+) m/z 419 (M+1).

2-(5-Butyl-4-(3-(1-methyl-1H-imidazol-5-yl)propyl)-1H-pyrazol-1-yl)-5-chloro-4-(thiophen-2-yl)pyrimidine (47). $^1$H NMR (400 MHz, CD$_3$OD) δ 8.71 (s, 1H), 7.90 (m, 1H), 7.74 (d, J=4.8 Hz, 1H), 7.54 (s, 1H), 7.28 (t, J=4.0 Hz, 1H), 7.01 (s, 1H), 7.61 (s, 1H), 4.63 (t, J=7.3 Hz, 1H), 3.63 (s, 3H), 2.77 (dt, J=12.13, 7.8 Hz, 1H), 2.63 (s, 3H), 2.08 (m, 2H), 1.69 (m, 2H), 1.32 (m, 2H), 0.86 (t, J=7.04 Hz, 3H. LCMS (ES+) m/z 421 (M+1).

1-[5-Methyl-4-(2-thienyl)pyrimidin-2-yl]-5-propyl-N-(1-pyridin-4-ylethyl)-1H-pyrazole-4-carboxamide (48). $^1$H NMR (500 MHz, DMSO-d$_6$) δ: 8.84 (s, 1H), 8.60 (d, J=7.81 Hz, 1H), 8.51 (d, J=5.86 Hz, 2H), 8.29 (s, 1H), 7.95 (m, 2H), 7.38 (d, J=5.86 Hz, 2H), 7.33 (dd, J=4.88, 3.91 Hz, 1H), 5.12 (m, 1H), 3.29 (m, 2H), 2.61 (s, 3H), 1.49 (m, 2H), 1.47 (d, J=7.32 Hz, 3H), 0.77 (t, J=7.33 Hz, 3H). LCMS (ES+) m/z 433 (M+1).

N-[(1-Methyl-1H-imidazol-5-yl)methyl]-1-[5-methyl-4-(2-thienyl)pyrimidin-2-yl]-5-propyl-1H-pyrazole-4-carboxamide (49). $^1$H NMR (400 MHz, DMSO-d$_6$) δ: 8.84 (s, 1H), 8.53 (t, J=5.47 Hz, 1H), 8.18 (s, 1H), 7.95 (d, J=5.08 Hz, 1H), 7.95 (d, J=3.91 Hz, 1H), 7.58 (s, 1H), 7.33 (dd, J=5.08, 3.91 Hz, 1H), 6.85 (s, 1H), 4.45 (d, J=5.48 Hz, 2H), 3.62 (s, 3H), 3.34 (m, 2H), 2.61 (s, 3H), 1.53 (m, 2H), 0.81 (t, J=7.43 Hz, 3H). LCMS (ES+) m/z 422 (M+1).

N-[2-(1-Methyl-1H-imidazol-5-yl)ethyl]-1-[5-methyl-4-(2-thienyl)pyrimidin-2-yl]-5-propyl-1H-pyrazole-4-carboxamide (50). $^1$H NMR (400 MHz, (DMSO-d$_6$) δ: 9.00 (s, 1H), 8.82 (s, 1H), 8.42 (t, J=5.86 Hz, 1H), 8.11 (s, 1H), 7.93 (m, 2H), 7.50 (s, 1H), 7.31 (dd, J=5.08, 3.91 Hz, 1H), 3.81 (s, 3H), 3.52 (d, J=5.86 Hz, 2H), 2.90 (t, J=6.64 Hz, 2H), 2.59 (s, 3H), 1.47 (q, J=7.43 Hz, 2H), 0.77 (t, J=7.43 Hz, 3H). LCMS (ES+) m/z 436 (M+1).

N-[(1-Methyl-1H-imidazol-5-yl)(pyridin-4-yl)methyl]-1-[5-methyl-4-(2-thienyl)pyrimidin-2-yl]-5-propyl-1H-pyrazole-4-carboxamide (51). $^1$H NMR (500 MHz, CDCl$_3$) δ: 8.67 (s, 1H), 8.64 (d, J=5.86 Hz, 2H), 7.99 (s, 1H), 7.82 (d, J=3.91 Hz, 1H), 7.63 (d, J=4.89 Hz, 1H), 7.50 (s, 1H), 7.33 (d, J=5.86 Hz, 2H), 7.24 (dd, J=4.88, 3.91 Hz, 1H), 6.59 (s, 1H), 6.52 (d, J=8.30 Hz, 1H), 3.66 (s, 3H), 3.60 (m, 2H), 2.64 (s, 3H), 1.70 (m, 2H), 0.93 (t, J=7.32 Hz, 3H). LCMS (ES+) m/z 499 (M+1).

N-[2-Hydroxy-1-(1-methyl-1H-imidazol-5-yl)ethyl]-1-[5-methyl-4-(2-thienyl)pyrimidin-2-yl]-5-propyl-1H-pyrazole-4-carboxamide (52). $^1$H NMR (400 MHz, CD$_3$OD) δ: 8.72 (s, 1H), 8.13 (s, 1H), 7.95 (dd, J=3.91, 0.78 Hz, 1H), 7.79 (d, J=5.08, 0.78 Hz, 1H), 7.60 (s, 1H), 7.29 (dd, J=5.08, 3.91 Hz, 1H), 7.04 (s, 1H), 5.36 (t, J=6.65 Hz, 1H), 3.94 (dd, J=6.65, 1.95 Hz, 2H), 3.73 (s, 3H), 3.56 (t, J=7.43 Hz, 2H), 2.65 (s, 3H), 1.65 (m, 2H), 0.90 (t, J=7.43 Hz, 3H). LCMS (ES+) m/z 452 (M+1).

1-[5-Methyl-4-(2-thienyl)pyrimidin-2-yl]-5-propyl-N-(5,6,7,8-tetrahydroisoquinolin-5-yl)-1H-pyrazole-4-carboxamide (53). $^1$H NMR (500, MHz (CDCl$_3$) δ 8.65 (s, 1H), 8.35 (d, J=5.00 Hz, 1H), 7.89 (s, 1H), 7.82 (d, J=5.00 Hz, 1H), 7.63 (d, J=5.00 Hz, 1H), 7.28-7.23 (m, 2H), 6.29-6.20 (m, 1H), 5.40 (dd, J=15.0, 10.0 Hz, 1H), 3.69-3.62 (m, 2H), 2.80 (t, J=10.0 Hz, 2H), 2.63 (3H, s), 2.28-2.19 (m, 1H), 2.03-1.66 (m, 5H), 0.99 (t, J=7.50 Hz, 3H). LCMS (ES+) m/z 459 (M+1).

5-(Methoxymethyl)-N-[(1-methyl-1H-imidazol-5-yl)methyl]-1-[5-methyl-4-(2-thienyl)pyrimidin-2-yl]-1H-pyrazole-4-carboxamide (54). $^1$H NMR (500 MHz, DMSO-d$_6$) δ: 8.82 (s, 1H), 8.66 (t, J=5.38 Hz, 1H), 8.19 (s, 1H), 7.96 (d, J=3.91 Hz, 1H), 7.94 (d, J=4.88 Hz, 1H), 7.56 (s, 1H), 7.32 (t, J=4.88, 3.91 Hz, 1H), 6.85 (s, 1H), 5.22 (s, 2H), 4.45 (d, J=5.37 Hz, 2H), 3.62 (s, 3H), 3.05 (s, 3H), 2.61 (s, 3H). LCMS (ES+) m/z 424 (M+1).

5-(Methoxymethyl)-N-(1-methyl-1-pyridin-4-ylethyl)-1-[5-methyl-4-(2-thienyl)pyrimidin-2-yl]-1H-pyrazole-4-carboxamide (55). $^1$H NMR (400Hz (DMSO-d$_6$) δ: 8.83 (s, 1H), 8.49 (s, 1H), 8.48 (dd, J=4.70, 1.57 Hz, 2H), 8.29 (s, 1H), 7.96 (d, J=3.91 Hz, 1H), 7.95 (d, J=5.09 Hz, 1H), 7.37 (dd, J=4.70, 1.57 Hz, 2H), 7.33 (dd, J=5.09, 3.91 Hz, 1H), 5.11 (s, 2H), 3.06 (s, 3H), 2.62 (s, 3H), 1.65 (s, 6H). LCMS (ES+) m/z 449 (M+1).

N-(Imidazo[1,2-a]pyridin-3-ylmethyl)-5-(methoxymethyl)-1-[5-methyl-4-(2-thienyl)pyrimidin-2-yl]-1H-pyrazole-4-carboxamide (56). $^1$H NMR (500 MHz, CDCl$_3$) δ: 8.65 (s, 1H), 8.34 (d, J=6.84 Hz, 1H), 8.23 (s, 1H), 7.88 (t, J=5.37 Hz, 1H), 7.80 (dd, J=3.90, 0.97 Hz, 1H), 7.64 (s, 1H), 7.62 (m, 2H), 7.23 (m, 2H), 6.88 (dd, J=6.84, 0.98 Hz, 1H), 5.17 (s, 2H), 4.99 (d, J=5.37 Hz, 2H), 3.16 (s, 3H), 2.62 (s, 3H). LCMS (ES+) m/z 460 (M+1).

5-(Ethoxymethyl)-1-[5-methyl-4-(2-thienyl)pyrimidin-2-yl]-N-(1-pyridin-4-ylethyl)-1H-pyrazole-4-carboxamide (57). $^1$H NMR (400 MHz, DMSO-d$_6$) δ: 8.84 (s, 1H), 8.75 (d, J=7.82 Hz, 1H), 8.51 (dd, J=4.30, 1.57 Hz, 2H), 8.29 (s, 1H), 7.98 (dd, J=3.91, 0.79 Hz, 1H), 7.94 (dd, J=5.08, 0.79 Hz, 1H), 7.39 (dd, J=4.30, 1.57 Hz, 2H), 7.33 (dd, J=5.08, 3.91 Hz, 1H), 5.18 (d, J=1.96 Hz, 2H), 5.12 (m, 1H), 3.23 (q, J=7.04 Hz, 2H), 2.62 (s, 3H), 1.48 (d, J=7.04 Hz, 3H), 0.77 (t, J=7.04 Hz, 3H). LCMS (ES+) m/z 449 (M+1).

5-(2-Methoxyethyl)-N-(1-methyl-1-pyridin-4-ylethyl)-1-[5-methyl-4-(2-thienyl)pyrimidin-2-yl]-1H-pyrazole-4-carboxamide (58). $^1$H NMR (400 MHz, CDCl$_3$) δ: 8.67 (s, 1H), 8.56 (dd, J=4.30, 1.56 Hz, 2H), 8.34 (s, 1H), 8.06 (s, 1H), 7.78 (d, J=3.91 Hz, 1H), 7.62 (dd, J=5.08, 0.78 Hz, 1H), 7.33 (dd, J=4.30, 1.56, 2H), 7.26 (dd, J=5.08, 3.91 Hz, 1H), 3.98 (t, J=5.47 Hz, 2H), 3.86 (t, J=5.47 Hz, 2H), 3.32 (s, 3H), 2.63 (s, 3H), 1.75 (s, 6H). LCMS (ES+) m/z 463 (M+1).

5-Butyl-1-[5-methyl-4-(2-thienyl)pyrimidin-2-yl]-N-(pyridin-4-ylmethyl)-1H-pyrazole-4-carboxamide (59). $^1$H NMR (400 MHz, DMSO-d$_6$) δ: 8.83 (s, 1H), 8.82 (t, J=5.47 Hz, 1H), 8.49 (ddd, J=5.86, 1.57, 1.56 Hz, 2H), 8.20 (d, J=1.17 Hz, 1H), 7.93 (m, 2H), 7.30 (m, 3H), 4.45 (d, J=5.86 Hz, 2H), 3.35 (t, J=7.04 Hz, 2H), 2.59 (s, 3H), 1.46 (m, 2H), 1.18 (m, 2H), 0.73 (t, J=7.43 Hz, 3H). LCMS (ES+) m/z 433 (M+1).

5-Butyl-N-(1-methyl-1-pyridin-4-ylethyl)-1-[5-methyl-4-(2-thienyl)pyrimidin-2-yl]-1H-pyrazole-4-carboxamide (60). $^1$H NMR (500 MHz, CDCl$_3$) δ: 8.67 (s, 1H), 8.57 (dd, J=4.39, 1.46 Hz, 2H), 7.92 (s, 1H), 7.81 (dd, J=3.91, 0.98 Hz, 1H), 7.62 (dd, J=4.88, 0.98 Hz, 1H), 7.33 (dd, J=4.39, 1.46, 2H), 7.23 (dd, J=4.88, 3.91 Hz, 1H), 6.09 (s, 1H), 3.56 (t, J=7.81 Hz, 2H), 2.63 (s, 3H), 1.77 (s, 6H), 1.56 (m, 2H), 1.28 (m, 2H), 0.78 (t, J=7.32 Hz, 3H). LCMS (ES+) m/z 461 (M+1).

5-Butyl-N-[(1,3-dimethyl-1H-pyrazol-5-yl)methyl]-1-[5-methyl-4-(2-thienyl)pyrimidin-2-yl]-1H-pyrazole-4-carboxamide (61). $^1$H NMR (400 MHz, CDCl$_3$) δ: 8.66 (d, J=0.78 Hz, 1H), 7.85 (s, 1H), 7.82 (dd, J=3.91, 1.17 Hz, 1H), 7.63 (dd, J=5.08, 1.17 Hz, 1H), 7.24 (dd, J=5.08, 3.91 Hz, 1H), 6.02 (s, 1H), 5.98 (t, J=5.48, 1H), 4.62 (d, J=5.48 Hz, 2H), 3.82 (s, 3H), 3.64 (dd, J=7.82, 7.82 Hz, 2H), 2.64 (s, 3H), 2.24 (s, 3H), 1.65 (m, 2H), 1.39 (m, 2H), 0.85 (t, J=7.42 Hz, 3H). LCMS (ES+) m/z 450 (M+1).

5-Butyl-N-(1H-imidazol-5-ylmethyl)-1-[5-methyl-4-(2-thienyl)pyrimidin-2-yl]-1H-pyrazole-4-carboxamide (62). $^1$H NMR (400 MHz, CD$_3$OD) δ: 8.73 (s, 1H), 8.10 (s, 1H), 7.96 (dd, J=3.91, 0.78 Hz, 1H), 7.80 (dd, J=5.08, 0.78 Hz, 1H), 7.64 (s, 1H), 7.30 (dd, J=5.08, 3.91 Hz, 1H), 7.03 (s, 1H), 4.50 (s, 2H), 3.58 (m, 2H), 2.66 (s, 3H), 1.59 (m, 2H), 1.32 (m, 2H), 0.83 (t, J=7.43 Hz, 3H). LCMS (ES+) m/z 422 (M+1).

N-[(1-Benzyl-1H-imidazol-5-yl)methyl]-5-butyl-1-[5-methyl-4-(2-thienyl)pyrimidin-2-yl]-1H-pyrazole-4-carboxamide (63). ¹H NMR (400 MHz, CDCl₃) δ: 8.66 (s, 1H), 7.81 (d, J=3.91 Hz, 1H), 7.63 (d, J=5.08 Hz, 1H), 7.60 (s, 1H), 7.28 (m, 5H), 7.13 (s, 1H), 7.09 (d, J=6.65 Hz, 1H), 5.52 (t, J=5.48 Hz, 1H), 5.21 (s, 2H), 4.57 (d, J=5.48 Hz, 2H), 3.57 (m, 2H), 2.63 (s, 3H), 1.60 (m, 2H), 1.36 (m, 2H), 0.84 (t, J=7.43 Hz, 3H). LCMS (ES+) m/z 512 (M+1).

5-Butyl-N-[(1R)-2-hydroxy-1-(1H-imidazol-5-ylmethyl) ethyl]-1-[5-methyl-4-(2-thienyl)pyrimidin-2-yl]-1H-pyrazole-4-carboxamide (64). ¹H NMR (500 MHz, DMSO-d₆) δ: 8.83 (s, 1H), 8.14 (s, 1H), 7.93 (m, 2H), 7.79 (s, 1H), 7.32 (dd, J=4.88, 3.90 Hz, 1H), 6.90 (s, 1H), 4.17 (m, 1H), 3.48 (dd, J=10.74, 5.37 Hz, 1H), 3.41 (dd, J=10.74, 5.86 Hz, 1H), 3.34 (t, J=7.81 Hz, 2H), 2.87 (dd, J=15.14, 5.37 Hz, 1H), 2.76 (dd, J=15.14, 8.30 Hz, 1H), 2.60 (s, 3H), 1.44 (m, 2H), 1.18 (m, 2H), 0.75 (t, J=7.33 Hz, 3H). LCMS (ES+) m/z 466 (M+1).

5-Butyl-N-[(1,2-dimethyl-1H-imidazol-5-yl)methyl]-1-[5-methyl-4-(2-thienyl)pyrimidin-2-yl]-1H-pyrazole-4-carboxamide (65). ¹H NMR 400 MHz (CDCl₃) δ: 8.66 (s, 1H), 7.85 (s, 1H), 7.82 (dd, J=3.91, 0.78 Hz, 1H), 7.63 (dd, J=5.08, 0.78 Hz, 1H), 7.24 (dd, J=5.08, 3.91 Hz, 1H), 6.92 (s, 1H), 5.91 (t, J=5.48 Hz, 1H), 4.62 (d, J=5.48 Hz, 2H), 3.64 (m, 2H), 3.54 (s, 3H), 2.64 (s, 3H), 2.40 (s, 3H), 1.65 (m, 2H), 1.38 (m, 2H), 0.86 (t, J=7.43 Hz, 3H). LCMS (ES+) m/z 450 (M+1).

5-Butyl-N-(imidazo[1,2-a]pyridin-3-ylmethyl)-1-[5-methyl-4-(2-thienyl)pyrimidin-2-yl]-1H-pyrazole-4-carboxamide (66). ¹H NMR (400 MHz, CDCl₃) δ: 8.63 (s, 1H), 8.33 (d, J=6.65 Hz, 1H), 7.93 (s, 1H), 7.82 (d, J=3.91 Hz, 1H), 7.62 (d, J=5.09 Hz, 1H), 7.57 (d, J=8.99 Hz, 1H), 7.50 (s, 1H), 7.24 (dd, J=5.09, 3.91 Hz, 1H), 7.19 (dd, J=8.99, 7.04 Hz, 1H), 6.83 (dd, J=7.04, 6.65 Hz, 1H), 6.61 (t, J=5.47 Hz, 1H), 4.98 (d, J=5.47 Hz, 2H), 3.68 (m, 2H), 2.62 (s, 3H), 1.86 (m, 2H), 1.39 (m, 2H), 0.86 (t, J=7.43 Hz, 3H). LCMS (ES+) m/z 472 (M+1).

5-Butyl-N-[1-(1-methyl-1H-imidazol-5-yl)ethyl]-1-[5-methyl-4-(2-thienyl)pyrimidin-2-yl]-1H-pyrazole-4-carboxamide (67). ¹H NMR (500 MHz, (DMSO-d₆) δ: 8.83 (s, 1H), 8.41 (d, J=8.79 Hz, 1H), 8.17 (s, 1H), 7.94 (m, 2H), 7.56 (s, 1H), 7.32 (dd, J=4.88, 3.91 Hz, 1H), 6.89 (s, 1H), 5.28 (m, 1H), 3.54 (s, 3H), 3.34 (m, 2H), 2.60 (s, 3H), 1.50 (d, J=6.84 Hz, 3H), 1.48 (m, 2H), 1.20 (m, 2H), 0.76 (t, J=7.32 Hz, 3H). LCMS (ES+) m/z 450 (M+1).

Methyl (5-{[({5-butyl-1-[5-methyl-4-(2-thienyl)pyrimidin-2-yl]-1H-pyrazol-4-yl}carbonyl)amino]methyl}-1H-imidazol-1-yl)acetate (68). ¹H NMR (400 MHz, CDCl₃) δ: 8.66 (s, 1H), 7.86 (s, 1H), 7.82 (d, J=3.91 Hz, 1H), 7.63 (d, J=5.08 Hz, 1H), 7.50 (s, 1H), 7.24 (dd, J=5.08, 3.91 Hz, 1H), 7.10 (s, 1H), 6.21 (t, J=5.48 Hz, 1H), 4.81 (s, 2H), 4.62 (d, J=5.48 Hz, 2H), 3.68 (s, 3H), 3.64 (t, J=7.83 Hz, 2H), 2.64 (s, 3H), 1.63 (m, 2H), 1.40 (m, 2H), 0.87 (t, J=7.43 Hz, 3H). LCMS (ES+) m/z 494 (M+1).

(5-{[({5-Butyl-1-[5-methyl-4-(2-thienyl)pyrimidin-2-yl]-1H-pyrazol-4-yl}carbonyl)amino]methyl}-1H-imidazol-1-yl)acetic acid (69). ¹H NMR (500 MHz, CD₃OD) δ: 8.97 (d, J=1.46 Hz, 1H), 8.74 (s, 1H), 8.07 (s, 1H), 7.97 (dd, J=3.91, 0.98 Hz, 1H), 7.80 (dd, J=4.89, 0.98 Hz, 1H), 7.61 (d, J=1.46 Hz, 1H), 7.30 (dd, J=4.89, 3.91 Hz, 1H), 5.25 (s, 2H), 4.66 (s, 2H), 3.56 (t, J=7.82 Hz, 2H), 2.66 (s, 3H), 1.60 (m, 2H), 1.35 (m, 2H), 0.84 (t, J=7.33 Hz, 3H). LCMS (ES+) m/z 480 (M+1).

5-Butyl-N-[2-hydroxy-1-(1-methyl-1H-imidazol-5-yl) ethyl]-1-[5-methyl-4-(2-thienyl)pyrimidin-2-yl]-1H-pyrazole-4-carboxamide (70). ¹H NMR (400 MHz, CD₃OD) δ: 8.73 (s, 1H), 8.13 (s, 1H), 7.95 (dd, J=3.91, 1.17 Hz, 1H), 7.79 (d, J=5.08, 1.17 Hz, 1H), 7.60 (s, 1H), 7.29 (dd, J=5.08, 3.91 Hz, 1H), 7.04 (s, 1H), 5.36 (t, J=6.65 Hz, 1H), 3.94 (dd, J=6.65, 1.95 Hz, 2H), 3.74 (s, 3H), 3.57 (t, J=7.43 Hz, 2H), 2.65 (s, 3H), 1.59 (m, 2H), 1.32 (m, 2H), 0.82 (t, J=7.43 Hz, 3H). LCMS (ES+) m/z 466 (M+1).

5-Butyl-N-(2-methoxy-1-pyridin-4-ylethyl)-1-[5-methyl-4-(2-thienyl)pyrimidin-2-yl]-1H-pyrazole-4-carboxamide (71). ¹H NMR (400 MHz, CDCl₃) δ: 8.68 (s, 1H), 8.58 (d, J=5.86 Hz, 2H), 7.98 (s, 1H), 7.82 (dd, J=3.91, 0.78 Hz, 1H), 7.63 (d, J=5.08, 0.78 Hz, 1H), 7.32 (d, J=5.86 Hz, 2H), 7.24 (dd, J=5.08, 3.91 Hz, 1H), 6.67 (d, J=7.43 Hz, 1H), 5.31 (dt, J=7.43, 4.30 Hz, 1H), 3.80 (dd, J=9.77, 3.91 Hz, 1H), 3.75 (dd, J=9.77, 4.30 Hz, 1H), 3.59 (m, 2H), 3.40 (s, 3H), 2.64 (s, 3H), 1.62 (m, 2H), 1.34 (m, 2H), 0.82 (t, J=7.43 Hz, 3H). LCMS (ES+) m/z 477 (M+1).

5-Butyl-1-[5-ethyl-4-(2-thienyl)pyrimidin-2-yl]-N-[(1-methyl-1H-imidazol-5-yl)methyl]-1H-pyrazole-4-carboxamide (72). ¹H NMR (400 MHz, CDC₃) δ: 8.69 (s, 1H), 7.94 (s, 1H), 7.76 (d, J=3.91 Hz, 1H), 7.61 (d, J=4.69 Hz, 1H), 7.52 (s, 1H), 7.22 (dd, J=4.69, 3.91 Hz, 1H), 7.01 (s, 1H), 6.55 (br s, 1H), 4.64 (d, J=5.48 Hz, 2H), 3.67 (s, 3H), 3.62 (t, J=7.43 Hz, 2H), 3.01 (q, J=7.43 Hz, 2H), 1.65 (m, 2H), 1.41 (t, J=7.43 Hz, 3H), 1.38 (m, 2H), 0.85 (t, J=7.43 Hz, 3H). LCMS (ES+) m/z 450 (M+1).

5-Butyl-N-(2-hydroxy-1-pyridin-4-ylethyl)-1-[5-methyl-4-(2-thienyl)pyrimidin-2-yl]-1H-pyrazole-4-carboxamide (73). ¹H NMR (400 MHz, CD₃OD) δ: 8.73 (d, J=0.78 Hz, 1H), 8.51 (dd, J=4.70, 1.57 Hz, 2H), 8.24 (s, 1H), 7.95 (dd, J=3.91, 0.78 Hz, 1H), 7.79 (d, J=5.08, 0.78 Hz, 1H), 7.50 (dd, J=4.70, 1.57 Hz, 2H), 7.29 (dd, J=5.08, 3.91 Hz, 1H), 5.18 (t, J=6.65 Hz, 1H), 3.90 (d, J=6.65 Hz, 2H), 3.52 (t, J=7.43 Hz, 2H), 2.65 (s, 3H), 1.55 (m, 2H), 1.28 (m, 2H), 0.78 (t, J=7.43 Hz, 3H). LCMS (ES+) m/z 463 (M+1).

5-Butyl-1-[5-methyl-4-(2-thienyl)pyrimidin-2-yl]-N-(5,6,7,8-tetrahydroimidazo[1,2-a]pyridin-3-ylmethyl)-1H-pyrazole-4-carboxamide (74). ¹H NMR (400 MHz, CDCl₃) δ: 8.66 (s, 1H), 7.85 (s, 1H), 7.82 (dd, J=3.91, 0.78 Hz, 1H), 7.63 (d, J=5.08, 0.78 Hz, 1H), 7.24 (dd, J=5.08, 3.91 Hz, 1H), 6.94 (s, 1H), 5.90 (t, J=5.48 Hz, 1H), 4.61 (d, J=5.48 Hz, 2H), 3.89 (t, J=6.26 Hz, 2H), 3.64 (t, J=7.82 Hz, 2H), 2.88 (t, J=6.26 Hz, 2H), 2.64 (s, 3H), 1.99 (m, 2H), 1.90 (m, 2H), 1.65 (m, 2H), 1.38 (m, 2H), 0.86 (t, J=7.43 Hz, 3H). LCMS (ES+) m/z 476 (M+1).

Methyl N-({5-butyl-1-[5-methyl-4-(2-thienyl)pyrimidin-2-yl]-1H-pyrazol-4-yl}carbonyl)-L-histidinate (75). ¹H NMR (400 MHz, CDCl₃) δ: 8.66 (s, 1H), 8.06 (s, 1H), 7.99 (br, 1H), 7.81 (d, J=3.91 Hz, 1H), 7.62 (m, 2H), 7.24 (m, 1H), 6.86 (s, 1H), 4.98 (m, 1H), 3.72 (s, 3H), 3.64 (m, 2H), 2.63 (s, 3H), 1.62 (m, 2H), 1.38 (m, 2H), 0.83 (t, J=7.43 Hz, 3H). LCMS (ES+) m/z 494 (M+1).

tert-Butyl (5-{[({5-butyl-1-[5-methyl-4-(2-thienyl)pyrimidin-2-yl]-1H-pyrazol-4-yl}carbonyl)amino]methyl}-4-methyl-1H-imidazol-1-yl)acetate (75). ¹H NMR (400 MHz, CD₃OD) δ: 8.73 (s, 1H), 8.05 (s, 1H), 7.96 (dd, J=3.91, 0.78 Hz, 1H), 7.79 (d, J=5.08, 0.78 Hz, 1H), 7.55 (s, 1H), 7.30 (dd, J=5.08, 3.91 Hz, 1H), 4.85 (s, 2H), 4.51 (s, 2H), 3.58 (t, J=7.43 Hz, 2H), 2.66 (s, 3H), 2.27 (s, 3H), 1.60 (m, 2H), 1.41 (s, 9H), 1.35 (m, 2H), 0.84 (t, J=7.43 Hz, 3H). LCMS (ES+) m/z 550 (M+1).

(5-{[({5-Butyl-1-[5-methyl-4-(2-thienyl)pyrimidin-2-yl]-1H-pyrazol-4-yl}carbonyl)amino]methyl}-4-methyl-1H-imidazol-1-yl)acetic acid (76). ¹H NMR (400 MHz, DMSO-d₆) δ: 8.84 (s, 1H), 8.53 (br, 1H), 8.10 (s, 1H), 7.95 (d, J=4.39 Hz, 2H), 7.57 (s, 1H), 7.33 (t, J=4.39 Hz, 1H), 4.79 (s, 2H), 4.35 (d, J=4.88 Hz, 2H), 3.36 (m, 2H), 2.61 (s, 3H), 2.17 (s, 3H), 1.48 (m, 2H), 1.21 (m, 2H), 0.76 (t, J=7.33 Hz, 3H). LCMS (ES+) m/z 494 (M+1).

(5-{[({5-Butyl-1-[5-methyl-4-(2-thienyl)pyrimidin-2-yl]-1H-pyrazol-4-yl}carbonyl)amino]methyl}-4-methyl-1H-imidazol-1-yl)acetic acid (77). $^1$H NMR (400 MHz, DMSO-d$_6$) δ: 9.06 (s, 1H), 8.85 (s, 1H), 8.80 (t, J=5.37 Hz, 1H), 8.13 (s, 1H), 7.96 (d, J=4.39 Hz, 2H), 7.33 (t, J=4.39 Hz, 1H), 5.22 (s, 2H), 4.45 (d, J=5.37 Hz, 2H), 3.36 (m, 2H), 2.62 (s, 3H), 2.41 (s, 3H), 1.48 (m, 2H), 1.21 (m, 2H), 0.76 (t, J=7.33 Hz, 3H). LCMS (ES+) m/z 494 (M+1).

N-{[1-(2-Amino-2-oxoethyl)-4-methyl-1H-imidazol-5-yl]methyl}-5-butyl-1-[5-methyl-4-(2-thienyl)pyrimidin-2-yl]-1H-pyrazole-4-carboxamide (78). $^1$H NMR (500 MHz, DMSO-d$_6$) δ: 8.84 (s, 1H), 8.32 (t, J=5.37 Hz, 1H), 8.08 (s, 1H), 7.95 (d, J=4.39 Hz, 2H), 7.58 (s, 1H), 7.45 (s, 1H), 7.33 (t, J=4.39 Hz, 1H), 7.32 (s, 1H), 4.68 (s, 2H), 4.33 (d, J=5.37 Hz, 2H), 3.38 (m, 2H), 2.61 (s, 3H), 2.14 (s, 3H), 1.48 (m, 2H), 1.21 (m, 2H), 0.76 (t, J=7.32 Hz, 3H). LCMS (ES+) m/z 493 (M+1).

5-Butyl-N-({4-methyl-1-[2-(methylamino)-2-oxoethyl]-1H-imidazol-5-yl}methyl)-1-[5-methyl-4-(2-thienyl)pyrimidin-2-yl]-1H-pyrazole-4-carboxamide (79). $^1$H NMR (400 MHz, DMSO-d$_6$) δ: 8.83 (s, 1H), 8.32 (t, J=5.48 Hz, 1H), 8.08 (s, 1H), 8.02 (m, 1H), 7.94 (d, J=4.69 Hz, 2H), 7.44 (s, 1H), 7.32 (t, J=4.69 Hz, 1H), 4.68 (s, 2H), 4.34 (d, J=5.08 Hz, 2H), 3.39 (m, 2H), 2.61 (s, 3H), 2.56 (d, J=4.30 Hz, 3H), 2.14 (s, 3H), 1.48 (m, 2H), 1.21 (m, 2H), 0.76 (t, J=7.32 Hz, 3H). LCMS (ES+) m/z 507 (M+1).

5-Butyl-N-({1-[2-(dimethylamino)-2-oxoethyl]-4-methyl-1H-imidazol-5-yl}methyl)-1-[5-methyl-4-(2-thienyl)pyrimidin-2-yl]-1H-pyrazole-4-carboxamide (80). $^1$H NMR (500 MHz, DMSO-d$_6$) δ: 8.84 (s, 1H), 8.27 (t, J=5.37 Hz, 1H), 8.07 (s, 1H), 7.95 (d, J=4.39 Hz, 2H), 7.37 (s, 1H), 7.33 (t, J=4.39 Hz, 1H), 4.95 (s, 2H), 4.33 (d, J=5.37 Hz, 2H), 3.39 (m, 2H), 3.00 (s, 3H), 2.74 (s, 3H), 2.61 (s, 3H), 2.15 (s, 3H), 1.49 (m, 2H), 1.22 (m, 2H), 0.77 (t, J=7.32 Hz, 3H). LCMS (ES+) m/z 521 (M+1).

(5-{[({1-[5-Bromo-4-(cyclobutylamino)pyrimidin-2-yl]-5-butyl-1H-pyrazol-4-yl}carbonyl)amino]methyl}-4-methyl-1H-imidazol-1-yl)acetic acid (81). $^1$H NMR (400 MHz, DMSO-d$_6$) δ: 8.45 (br, 1H), 8.44 (s, 1H), 8.02 (s, 1H), 7.71 (d, J=7.82 Hz, 1H), 7.57 (s, 1H), 4.79 (s, 2H), 4.56 (m, 1H), 4.33 (d, J=5.08 Hz, 2H), 3.29 (m, 2H), 2.21 (m, 4H), 2.16 (s, 3H), 1.65 (m, 2H), 1.47 (m, 2H), 1.24 (m, 2H), 0.82 (t, J=7.43 Hz, 3H). LCMS (ES+) m/z 545 (M+1).

5-Butyl-1-[5-methyl-4-(2-thienyl)pyrimidin-2-yl]-N-(4,5,6,7-tetrahydro-1H-benzimidazol-7-yl)-1H-pyrazole-4-carboxamide (82). $^1$H NMR (400 MHz, CD$_3$OD) δ 8.74 (s, 1H), 8.11 (s, 1H), 8.03 (s, 1H), 7.98 (d, J=3.91 Hz, 1H), 7.81 (d, J=5.08 Hz, 1H), 7.30 (dd, J=5.08, 3.91 Hz, 1H), 5.27-5.21 (m, 1H), 3.60 (t, J=7.82 Hz, 2H), 2.66 (s, 3H), 2.75-2.61 (m, 2H), 2.18-1.88 (m, 4H), 1.67-1.56 (m, 2H), 1.41-1.30 (m, 2H), 0.85 (t, J=7.43 Hz, 3H). LCMS (ES+) m/z 462 (M+1).

N-1H-Benzimidazol-7-yl-5-butyl-1-[5-methyl-4-(2-thienyl)pyrimidin-2-yl]-1H-pyrazole-4-carboxamide (83). $^1$H NMR (400 MHz, DMSO-d6) δ 8.88 (s, 1H), 8.43 (s, 1H), 8.24 (s, 1H), 8.01-7.95 (m, 3H), 7.49-7.32 (m, 2H), 7.20 (t, J=7.82 Hz, 1H), 3.43 (t, J=7.83 Hz, 2H), 2.64 (s, 3H), 1.61-1.51 (m, 2H), 1.31-1.21 (m, 2H), 0.78 (t, J=7.43 Hz, 3H). LCMS (ES+) m/z 458 (M+1).

5-Butyl-N-[2-(1H-imidazol-1-yl)ethyl]-1-[5-methyl-4-(2-thienyl)pyrimidin-2-yl]-1H-pyrazole-4-carboxamide (84). $^1$H NMR (500 MHz, (DMSO-d6) δ 9.10 (s, 1H), 8.84 (s, 1H), 8.35 (t, J=5.86 Hz, 1H), 8.07 (s, 1H), 7.96 (d, J=2.93 Hz, 1H), 7.76 (s, 1H), 7.66 (s, 1H), 7.84 (dd, J=5.86, 2.93 Hz, 1H), 4.35 (t, J=5.87 Hz, 2H), 3.69 (q, J=5.87 Hz, 2H), 3.31 (t, J=7.82 Hz, 2H), 2.62 (s, 3H), 1.48-1.40 (m, 2H), 1.24-1.14 (m, 2H), 0.76 (t, J=7.32 Hz, 3H). LCMS (ES+) m/z 436 (M+1).

N-[2-(1H-Benzimidazol-1-yl)ethyl]-5-butyl-1-[5-methyl-4-(2-thienyl)pyrimidin-2-yl]-1H-pyrazole-4-carboxamide (85). $^1$H NMR (400 MHz, CD$_3$OD) δ 8.73 (s, 1H), 8.21 (s, 1H), 7.96 (d, J=3.91 Hz, 1H), 7.87 (s, 1H), 7.82 (d, J=5.86 Hz, 1H), 7.70-7.62 (m, 2H), 7.35-7.24 (m, 3H), 4.54 (t, J=5.87 Hz, 2H), 3.73 (t, J=5.87 Hz, 2H), 3.48 (t, J=7.82 Hz, 2H), 2.65 (s, 3H), 1.57-1.46 (m, 2H), 1.35-1.23 (m, 2H), 0.82 (t, J=7.43 Hz, 3H). LCMS (ES+) m/z 486 (M+1).

8-({5-Butyl-1-[5-methyl-4-(2-thienyl)pyrimidin-2-yl]-1H-pyrazol-4-yl}carbonyl)-6,7,8,9-tetrahydro-5H-imidazo[1,5-a][1,4]diazepine (86). $^1$H NMR (400 MHz, DMSO-d6) δ 9.01 (s, 1H), 8.81 (s, 1H), 7.96-7.89 (m, 2H), 7.81 (s, 1H), 7.65 (brs, 1H), 7.31 (dd, J=5.08, 3.91 Hz, 1H), 4.90-4.78 (m, 2H), 4.56-4.46 (m, 2H), 3.94-3.81 (m, 2H), 3.08 (t, J=8.21 Hz, 2H), 2.59 (s, 3H), 2.02-1.91 (m, 2H), 1.40-1.25 (m, 2H), 1.17-1.05 (m, 2H), 0.66 (t, J=7.43 Hz, 3H). LCMS (ES+) m/z 462 (M+1).

5-Butyl-N-(6,7-dihydro-5H-pyrrolo[1,2-c]imidazol-7-yl)-1-[5-methyl-4-(2-thienyl)pyrimidin-2-yl]-1H-pyrazole-4-carboxamide (87). $^1$H NMR (400 MHz, CD$_3$OD) δ 8.73 (s, 1H), 8.08 (s, 1H), 7.97 (d, J=3.52 Hz, 1H), 7.80 (d, J=4.70 Hz, 1H), 7.64 (s, 1H), 7.30 (dd, J=4.70, 3.52 Hz, 1H), 6.89 (s, 1H), 5.50 (dd, J=8.21, 4.31 Hz, 1H), 4.34-4.24 (m, 1H), 4.19-4.10 (m, 1H), 3.59 (t, J=7.82 Hz, 2H), 3.17-3.04 (m, 1H), 2.66 (s, 3H), 2.66-2.56 (m, 1H), 1.66-1.54 (m, 2H), 1.41-1.29 (m, 2H), 0.85 (t, J=7.43 Hz, 3H). LCMS (ES+) m/z 448 (M+1).

5-Butyl-1-[5-methyl-4-(2-thienyl)pyrimidin-2-yl]-N-(5,6,7,8-tetrahydroimidazo[1,5-a]pyridin-8-yl)-1H-pyrazole-4-carboxamide (88). $^1$H NMR (400 MHz, CD$_3$OD) δ 8.72 (s, 1H), 8.08 (s, 1H), 7.96 (d, J=3.91 Hz, 1H), 7.80 (d, J=5.08 Hz, 1H), 7.75 (s, 1H), 7.29 (dd, J=5.08, 3.91 Hz, 1H), 6.99 (s, 1H), 5.35 (dd, J=7.43, 4.69 Hz, 1H), 4.22-4.12 (m, 1H), 4.12-4.01 (m, 1H), 3.60 (t, J=7.82 Hz, 2H), 2.66 (s, 3H), 2.29-2.18 (m, 2H), 2.09-1.86 (m, 2H), 1.67-1.55 (m, 2H), 1.42-1.31 (m, 2H), 0.86 (t, J=7.43 Hz, 3H). LCMS (ES+) m/z 462 (M+1).

{7-[({5-Butyl-1-[5-methyl-4-(2-thienyl)pyrimidin-2-yl]-1H-pyrazol-4-yl}carbonyl)amino]-1H-benzimidazol-1-yl}acetic acid (89). $^1$H NMR (500 MHz, CD$_3$OD) δ 8.81 (s, 1H), 8.75 (s, 1H), 8.31 (s, 1H), 7.96 (d, J=3.91 Hz, 1H), 7.79-7.74 (m, 2H), 7.54 (t, J=7.32 Hz, 1H), 7.39 (d, J=7.32 Hz, 1H), 7.30 (dd, J=4.88, 3.90 Hz, 1H), 5.24 (s, 2H), 3.64 (t, J=7.81 Hz, 2H), 2.70 (s, 3H), 1.72-1.64 (m, 2H), 1.42-1.33 (m, 2H), 0.85 (t, J=7.32 Hz, 3H). LCMS (ES+) m/z 516 (M+1).

Methyl 1-{2-[({5-butyl-1-[5-methyl-4-(2-thienyl)pyrimidin-2-yl]-1H-pyrazol-4-yl}carbonyl)amino]ethyl}-1H-imidazole-5-carboxylate (90). $^1$H NMR (400 MHz, CD$_3$OD) δ 8.71 (s, 1H), 7.97 (s, 1H), 7.94 (d, J=3.91 Hz, 1H), 7.78 (s, 1H), 7.76 (d, J=5.08 Hz, 1H), 7.69 (s, 1H), 7.29 (dd, J=5.09, 3.91 Hz, 1H), 4.59 (t, J=5.86 Hz, 2H), 3.86 (s, 3H), 3.74 (t, J=5.86 Hz, 2H), 3.55 (t, J=7.82 Hz, 2H), 2.67 (s, 3H), 1.64-1.54 (m, 2H), 1.40-1.29 (m, 2H), 0.85 (t, J=7.43 Hz, 3H). LCMS (ES+) m/z 494 (M+1).

1-{2-[({5-Butyl-1-[5-methyl-4-(2-thienyl)pyrimidin-2-yl]-1H-pyrazol-4-yl}carbonyl)amino]ethyl}-1H-imidazole-5-carboxylic acid (91). $^1$H NMR (500 MHz, CD$_3$OD) δ 8.73 (s, 1H), 8.39 (s, 1H), 7.99 (s, 1H), 7.96 (dd, J=3.90, 0.97 Hz, 1H), 7.87 (s, 1H), 7.80 (dd, J=5.37, 0.97 Hz, 1H), 7.79 (dd, J=5.37, 3.91 Hz, 1H), 4.70 (t, J=5.37 Hz, 2H), 3.80 (q, J=5.86 Hz, 2H), 3.60 (t, J=7.82 Hz, 2H), 2.65 (s, 3H), 1.59-1.50 (m, 2H), 1.36-1.27 (m, 2H), 0.83 (t, J=7.32 Hz, 3H). LCMS (ES+) m/z 480 (M+1).

1-[5-Bromo-4-(cyclobutylamino)pyrimidin-2-yl]-5-butyl-N-(imidazo[1,2-a]pyridin-3-ylmethyl)-1H-pyrazole-4-carboxamide (92). $^1$H NMR (400 MHz, CDCl$_3$) δ 8.32 (s, 1H), 8.11 (s, 1H), 8.30 (d, J=6.80 Hz, 1H), 7.91 (br, 1H), 7.54 (m, 1H), 7.42 (br, 1H), 7.17 (t, J=7.20 Hz, 1H), 6.82 (t, J=6.80 Hz, 1H), 6.71 (br, 1H), 5.69 (d, J=8.00 Hz, 1H), 4.95 (d, J=5.60 Hz, 2H), 4.69-4.55 (m, 1H), 3.57 (t, J=7.6 Hz, 2H), 2.52-2.40 (m, 2H), 2.08-1.94 (m, 2H), 1.90-1.60 (m, 4H), 1.48-1.35 (m, 2H), 0.93 (t, J=7.20 Hz, 3H). LCMS (ES+) m/z 523 (M+1), 525 (M+1).

N-({5-Butyl-1-[5-methyl-4-(2-thienyl)pyrimidin-2-yl]-1H-pyrazol-4-yl}carbonyl)-L-histidine (93). $^1$H NMR (400 MHz, DMSO-d6) δ 8.98 (d, J=1.2 Hz, 1H), 8.85 (s, 1H), 8.62 (d, J=8.00 Hz, 1H), 8.27 (1H, s), 7.96 (dd, J=4.80, 1.20 Hz, 2H), 7.43 (1H, s), 7.36-7.31 (m, 1H), 4.80-4.70 (m, 2H), 3.40-3.10 (m, 4H), 2.62 (s, 3H), 1.53-1.36 (m, 2H), 1.28-1.10 (m, 2H), 0.75 (t, J=7.20 Hz, 3H). LCMS (ES+) m/z 480 (M+1).

5-Butyl-1-[5-methyl-4-(2-thienyl)pyrimidin-2-yl]-N-(5,6,7,8-tetrahydroisoquinolin-5-yl)-1H-pyrazole-4-carboxamide (94). $^1$H NMR (400 MHz, CDCl$_3$) δ 8.66 (s, 1H), 8.39 (s, 1H), 8.37 (s, 1H), 7.87 (s, 1H), 7.82 (d, J=4.00 Hz, 1H), 7.63 (d, J=4.00 Hz, 1H), 7.29-7.22 (m, 2H), 6.11 (d, J=8.00 Hz, 1H), 5.45-5.36 (m, 1H), 3.66 (t, J=8.00 Hz, 2H), 2.82 (t, J=8.00 Hz, 2H), 2.64 (s, 3H), 2.29-2.19 (m, 1H), 2.03-1.78 (m, 3H), 1.74-1.63 (m, 2H), 1.46-1.35 (m, 2H), 0.87 (t, J=8.00 Hz, 3H). LCMS (ES+) m/z 473 (M+1).

5-Butyl-N-isoquinolin-5-yl-1-[5-methyl-4-(2-thienyl)pyrimidin-2-yl]-1H-pyrazole-4-carboxamide (95). $^1$H NMR (400 MHz, CDCl$_3$) δ 9.30 (s, 1H), 8.69 (s, 1H), 8.60 (d, J=4.00 Hz, 1H), 8.22 (d, J=8.00 Hz, 1H), 8.14 (s, 1H), 7.93-7.81 (m, 3H), 7.73-7.62 (m, 3H), 7.28-7.21 (m, 1H), 3.68 (t, J=8.00 Hz, 2H), 2.65 (s, 3H), 1.76-1.66 (m, 2H), 1.46-1.34 (m, 2H), 0.85 (t, J=8.00 Hz, 3H). LCMS (ES+) m/z 469 (M+1).

5-Butyl-1-[5-methyl-4-(2-thienyl)pyrimidin-2-yl]-N-(1-pyridin-4-ylpropyl)-1H-pyrazole-4-carboxamide (96). $^1$H NMR (500 MHz, CD$_3$OD) δ: 8.82 (d, J=6.84 Hz, 2H), 8.75 (s, 1H), 8.27 (s, 1H), 8.13 (d, J=6.84 Hz, 2H), 7.98 (d, J=3.91 Hz, 1H), 7.80 (d, J=4.88 Hz, 1H), 7.30 (dd, J=5.37, 3.91 Hz, 1H), 5.14 (t, J=7.34 Hz, 1H), 3.50 (t, J=7.81 Hz, 2H), 2.67 (s, 3H), 2.01 (m, 2H), 1.54 (m, 2H), 1.28 (m, 2H), 1.12 (t, J=7.32 Hz, 3H), 0.78 (t, J=7.33 Hz, 3H). LCMS (ES+) m/z 461 (M+1).

5-Isobutyl-1-[5-methyl-4-(2-thienyl)pyrimidin-2-yl]-N-(pyridin-4-ylmethyl)-1H-pyrazole-4-carboxamide (97). $^1$H NMR (500 MHz, CD$_3$OD) δ: 8.82 (d, J=6.84 Hz, 2H), 8.77 (s, 1H), 8.23 (s, 1H), 8.08 (d, J=6.35 Hz, 2H), 8.00 (d, J=3.91 Hz, 1H), 7.82 (d, J=4.88 Hz, 1H), 7.32 (dd, J=5.37, 3.91 Hz, 1H), 4.84 (s, 2H), 3.64 (d, J=7.33 Hz, 2H), 2.68 (s, 3H), 1.76 (m, 1H), 0.78 (d, J=6.84 Hz, 6H). LCMS (ES+) m/z 433 (M+1).

7.40. Example 98

5-(Ethoxymethyl)-N-((1-methyl-1H-imidazol-5-yl)methyl)-1-(5-methyl-4-(thiophen-2-yl)pyrimidin-2-yl)-1H-pyrazole-4-carboxamide (98). The title compound 98 was prepared by following the procedures described in Example 1 with the exceptions that B.1 was 4-ethoxy-3-oxobutanoate in place of methyl 4-methoxy-3-oxobutanoate in Step 3 and that (1-methyl-1H-imidazol-5-yl)methanamine was used in place of pyridin-4-ylmethanamine in Step 5. $^1$H NMR 400 MHz (DMSO-d6) δ 8.83 (s, 1H), 8.64 (t, J=4.0 Hz), 8.18 (s, 1H), 7.97 (d, J=4.0 Hz), 7.95 (d, J=4.0 Hz), 7.56 (s, 1H), 7.32 (dd, J=8.0, 4.0 Hz, 1H), 6.85 (s, 1H), 5.52 (s, 2H), 4.46 (d, J=4.0 Hz, 2H), 3.62 (s, 3H), 3.25 (q, J=4.0 Hz, 2H), 2.62 (s, 3H), 1.18 (t, J=4.0 Hz, 3H). LCMS (ES+) m/z 438 (M+1).

7.41. Example 99

5-(Ethoxymethyl)-N-((1-methyl-1H-imidazol-5-yl)methyl)-1-(5-methyl-4-(piperidin-1-yl)pyrimidin-2-yl)-1H-pyrazole-4-carboxamide (99). The title compound 99 was prepared by following the synthetic sequence and conditions described in Example 14 and Example 16 with the following modifications. First in Step 2 of Example 14, intermediate D.2 (R$^2$=methyl, R$^3$=H) was treated with (Z)-methyl 2-((dimethylamino)methylene)-4-ethoxy-3-oxobutanoate, instead of (Z)-methyl 2-((dimethylamino)methylene)-3-oxoheptanoate, to give D.3 (R$^2$=methyl, R$^4$=ethoxymethyl). This intermediate D.3 was converted to the corresponding D.5, 1-(4-chloro-5-methylpyrimidin-2-yl)-5-(ethoxymethyl)-N-((1-methyl-1H-imidazol-5-yl)methyl)-1H-pyrazole-4-carboxamide, in three steps (Steps 3-5).

Similar to what was described in Example 16, a solution of D.5 from above in DMF and an equivalent molar of piperidine was stirred overnight at room temperature. The resulting mixture was concentrated and purified by HPLC (Capcell Pak C$_{18}$ column, gradient of 20% A: 80% B to 80% A: 20% B over 45 minutes; A=0.1% TFA in water, B=0.1% TFA in MeCN) to give the title compound as a white solid. Mass Spectrum (ESI) m/e=439 (M+1). $^1$H NMR 400 MHz (CDCl$_3$) δ: 8.17 (s, 1H), 8.13 (s, 1H), 8.06 (br t, J=5.47 Hz, 1H), 7.50 (s, 1H), 7.04 (s, 1H), 5.13 (s, 2H), 4.63 (d, J=5.47 Hz, 2H), 3.68 (s, 3H), 3.57-3.49 (m, 4H), 3.46 (q, J=7.04 Hz, 2H), 2.28 (s, 3H), 1.75-1.65 (m, 6H), 1.02 (t, J=7.04 Hz, 3H).

7.42. Examples 100-132

The following examples were synthesized with slight modifications to the synthetic procedures described above.

N-{[4-(Hydroxymethyl)-1-methyl-1H-imidazol-5-yl]methyl}-1-[5-methyl-4-(2-thienyl)pyrimidin-2-yl]-5-propyl-1H-pyrazole-4-carboxamide (100). $^1$H NMR 400 MHz (CDCl$_3$) δ: 8.65 (s, 1H), 7.88 (s, 1H), 7.81 (dd, J=3.91, 0.78 Hz, 1H), 7.63 (dd, J=5.08, 0.78 Hz, 1H), 7.38 (s, 1H), 7.24 (dd, J=5.08, 3.91 Hz, 1H), 6.71 (br t, J=5.47 Hz, 1H), 4.71 (s, 2H), 4.68 (d, J=5.47 Hz, 2H), 3.68 (s, 3H), 3.65-3.58 (m, 2H), 2.62 (s, 3H), 1.75-1.64 (m, 2H), 0.95 (t, J=7.43 Hz, 3H). LCMS (ES+) m/z 452 (M+1).

1-[5-Chloro-4-(2-thienyl)pyrimidin-2-yl]-5-(ethoxymethyl)-N-{[4-(hydroxymethyl)-1-methyl-1H-imidazol-5-yl]methyl}-1H-pyrazole-4-carboxamide (101). 5-(Ethoxymethyl)-1-(5-methyl-4-(thiophen-2-yl)pyrimidin-2-yl)-1H-pyrazole-4-carboxylic acid (163 mg) and HBTU (204 mg) were dissolved in N,N-dimethylformamide at room temperature. To this solution, diisopropylethyl amine (139 mg) and 1-[4-({[tert-butyl(diphenyl)silyl]oxy}methyl)-1-methyl-1H-imidazol-5-yl]methanamine (125 mg) were added sequentially. After stirring for 1 hour, the reaction mixture was treated with water and extracted with ethyl acetate (×3). The combined organic layers were washed with water, brine, dried over sodium sulfate, then evaporated under reduced pressure. The residue was purified by silica gel column chromatography to give N-{[4-({[tert-butyl(diphenyl)silyl]oxy}methyl)-1-methyl-1H-imidazol-5-yl]methyl}-1-[5-chloro-4-(2-thienyl)pyrimidin-2-yl]-5-(ethoxymethyl)-1H-pyrazole-4-carboxamide (263 mg). This compound (263 mg) was dissolved in THF at room temperature. To this solution, 1M TBAF in THF (0.54 mL) was added. After stirring for 80 min, the reaction mixture was treated with water and extracted with dichloromethane (×2). The combined organic layers were washed with water, brine, dried over sodium sulfate, then evaporated under reduced pressure. The residue was purified by silica gel (NH) column chromatography to give 1-[5-chloro-4-(2-thienyl)pyrimidin-2-yl]-5-(ethoxymethyl)-N-{[4-(hydroxymethyl)-1-methyl-1H-imidazol-5-yl]methyl}-1H-pyrazole-4-carboxamide (80 mg). $^1$H NMR 400 MHz (CDCl$_3$) δ: 8.79 (s, 1H), 8.42 (dd, J=3.91, 0.78 Hz, 1H), 8.19 (s, 1H), 8.09 (br t, J=5.47 Hz, 1H), 7.70 (dd, J=5.08, 0.78 Hz, 1H), 7.40 (s, 1H), 7.26 (dd, J=5.08, 3.91 Hz, 1H), 5.31 (s, 2H), 4.69 (s, 2H), 4.67 (d, J=5.47 Hz, 2H), 3.69 (s, 3H), 3.53 (q, J=7.04 Hz, 2H), 1.04 (t, J=7.04 Hz, 3H). LCMS (ES+) m/z 488 (M+1).

1-[4-(3,4-Dihydroisoquinolin-2(1H)-yl)-5-methylpyrimidin-2-yl]-5-(ethoxymethyl)-N-{[4-(hydroxymethyl)-1-methyl-1H-imidazol-5-yl]methyl}-1H-pyrazole-4-carboxamide (102). $^1$H NMR 400 MHz (CDCl$_3$) δ: 8.18 (s, 1H), 8.14 (s, 1H), 8.10 (br t, J=5.47 Hz, 1H), 7.39 (s, 1H), 7.24-7.13 (m, 4H), 5.16 (s, 2H), 4.78 (s, 2H), 4.69 (s, 2H), 4.65 (d, J=5.47 Hz, 2H), 3.85 (t, J=5.87 Hz, 2H), 3.68 (s, 3H), 3.46 (q, J=7.04 Hz, 2H), 3.03 (t, J=5.87 Hz, 2H), 2.38 (s, 3H), 1.03 (t, J=7.04 Hz, 3H). LCMS (ES+) m/z 517 (M+1).

5-(Ethoxymethyl)-1-[4-(2-furyl)-5-methylpyrimidin-2-yl]-N-[(1-methyl-1H-imidazol-5-yl)methyl]-1H-pyrazole-4-carboxamide (103). $^1$H NMR 400 MHz (CDCl$_3$) δ: 8.64 (s, 1H), 8.22 (s, 1H), 8.05 (br t, J=5.47 Hz, 1H), 7.72 (dd, J=1.96, 0.78 Hz, 1H), 7.45 (s, 1H), 7.33 (dd, J=3.52, 0.78 Hz, 1H), 7.04 (s, 1H), 6.65 (dd, J=3.52, 1.96 Hz, 1H), 5.21 (s, 2H), 4.64 (d, J=5.47 Hz, 2H), 3.68 (s, 3H), 3.51 (q, J=7.04 Hz, 2H), 2.62 (s, 3H), 1.04 (t, J=7.04 Hz, 3H). LCMS (ES+) m/z 422 (M+1).

5-(Ethoxymethyl)-N-[(1-methyl-1H-imidazol-5-yl)methyl]-1-[5-methyl-4-(1,3-thiazol-2-yl)pyrimidin-2-yl]-1H-pyrazole-4-carboxamide (104). $^1$H NMR 400 MHz (CDCl$_3$) δ: 8.81 (s, 1H), 8.25 (s, 1H), 8.10 (d, J=3.13 Hz, 1H), 8.07 (br t, J=5.47 Hz, 1H), 7.62 (d, J=3.13 Hz, 1H), 7.45 (s, 1H), 7.04 (s, 1H), 5.26 (s, 2H), 4.65 (d, J=5.47 Hz, 2H), 3.68 (s, 3H), 3.52 (q, J=7.04 Hz, 2H), 2.85 (s, 3H), 1.03 (t, J=7.04 Hz, 3H). LCMS (ES+) m/z 439 (M+1).

5-(Ethoxymethyl)-N-{[4-(hydroxymethyl)-1-methyl-1H-imidazol-5-yl]methyl}-1-[5-methyl-4-(2-thienyl)pyrimidin-2-yl]-1H-pyrazole-4-carboxamide (105). $^1$H NMR 500 MHz (CD$_3$OD) δ: 8.72 (s, 1H), 8.10 (s, 1H), 7.98 (dd, J=3.91, 0.78 Hz, 1H), 7.79 (dd, J=5.08, 0.78 Hz, 1H), 7.58 (s, 1H), 7.29 (dd, J=5.08, 3.91 Hz, 1H), 5.35 (s, 2H), 4.66 (s, 2H), 4.63 (s, 2H), 3.73 (s, 3H), 3.41 (q, J=7.04 Hz, 2H), 2.66 (s, 3H), 0.90 (t, J=7.04 Hz, 3H). LCMS (ES+) m/z 468 (M+1).

1-[4-(Cyclohexylamino)-5-methylpyrimidin-2-yl]-5-(ethoxymethyl)-N-[(1-methyl-1H-imidazol-5-yl)methyl]-1H-pyrazole-4-carboxamide (106). $^1$H NMR 400 MHz (DMSO-d$_6$) δ: 8.53 (br t, J=5.47 Hz, 1H), 8.05 (s, 1H), 7.97 (s, 1H), 7.55 (s, 1H), 6.83 (s, 1H), 6.80 (d, J=8.60 Hz, 1H), 5.12 (s, 2H), 4.44 (d, J=5.47 Hz, 2H), 4.04-3.89 (m, 1H), 3.61 (s, 3H), 3.27 (q, J=7.04 Hz, 2H), 2.05 (s, 3H), 1.93-1.55 (m, 5H), 1.45-1.05 (m, 5H), 0.87 (t, J=7.04 Hz, 3H). LCMS (ES+) m/z 453 (M+1).

5-(2-Methoxyethyl)-N-[(1-methyl-1H-imidazol-5-yl)methyl]-1-(5-methyl-4-pyrrolidin-1-ylpyrimidin-2-yl)-1H-pyrazole-4-carboxamide (107). $^1$H NMR 400 MHz (CDCl$_3$) δ: 8.05-7.99 (m, 2H), 7.97 (s, 1H), 7.45 (s, 1H), 7.02 (s, 1H), 4.59 (d, J=5.47 Hz, 2H), 3.80-3.68 (m, 6H), 3.68 (s, 3H), 3.62 (t, J=5.47 Hz, 2H), 3.12 (s, 3H), 2.39 (s, 3H), 2.01-1.92 (m, 4H). LCMS (ES+) m/z 425 (M+1).

5-(Ethoxymethyl)-N-[(1-methyl-1H-imidazol-5-yl)methyl]-1-(5-methyl-4-pyrrolidin-1-ylpyrimidin-2-yl)-1H-pyrazole-4-carboxamide (108). $^1$H NMR 400 MHz (CDCl$_3$) δ: 8.15 (s, 1H), 8.12 (br t, J=5.08 Hz, 1H), 7.98 (s, 1H), 7.52 (s, 1H), 7.04 (s, 1H), 5.17 (s, 2H), 4.62 (d, J=5.08 Hz, 2H), 3.82-3.72 (m, 4H), 3.68 (s, 3H), 3.44 (q, J=7.04 Hz, 2H), 2.41 (s, 3H), 2.00-1.92 (m, 4H), 1.01 (t, J=7.04 Hz, 3H). LCMS (ES+) m/z 425 (M+1).

1-[5-Chloro-4-(cyclopropylamino)pyrimidin-2-yl]-5-(ethoxymethyl)-N-[(1-methyl-1H-imidazol-5-yl)methyl]-1H-pyrazole-4-carboxamide (109). $^1$H NMR 400 MHz (CDCl$_3$) δ: 8.26 (s, 1H), 8.20 (s, 1H), 8.12 (br t, J=5.08 Hz, 1H), 7.44 (s, 1H), 7.03 (s, 1H), 5.74 (br s, 1H), 5.29 (s, 2H), 4.63 (d, J=5.08 Hz, 2H), 3.67 (s, 3H), 3.47 (q, J=7.04 Hz, 2H), 2.94-2.87 (m, 1H), 1.01 (t, J=7.04 Hz, 3H), 0.97-0.91 (m, 2H), 0.71-0.65 (m, 2H). LCMS (ES+) m/z 431 (M+1).

5-(Ethoxymethyl)-N-[(1-methyl-1H-imidazol-5-yl)methyl]-1-[5-methyl-4-(3,3,4,4-tetrafluoropyrrolidin-1-yl)pyrimidin-2-yl]-1H-pyrazole-4-carboxamide (110). $^1$H NMR 400 MHz (CDCl$_3$) δ: 8.18 (s, 1H), 8.14 (s, 1H), 7.83 (br t, J=5.37 Hz, 1H), 7.48 (s, 1H), 7.03 (s, 1H), 5.07 (s, 2H), 4.63 (d, J=5.37 Hz, 2H), 4.35-4.21 (m, 4H), 3.67 (s, 3H), 3.46 (q, J=6.84 Hz, 2H), 2.41 (s, 3H), 1.04 (t, J=6.84 Hz, 3H). LCMS (ES+) m/z 497 (M+1).

5-(Ethoxymethyl)-N-[(1-methyl-1H-imidazol-5-yl)methyl]-1-(5-methyl-4-phenylpyrimidin-2-yl)-1H-pyrazole-4-carboxamide (111). $^1$H NMR 400 MHz (CDCl$_3$) δ: 8.72 (s, 1H), 8.22 (s, 1H), 7.96 (br t, J=5.47 Hz, 1H), 7.70-7.64 (m, 2H), 7.54-7.49 (m, 3H), 7.45 (s, 1H), 7.03 (s, 1H), 5.16 (s, 2H), 4.63 (d, J=5.47 Hz, 2H), 3.67 (s, 3H), 3.42 (q, J=7.04 Hz, 2H), 2.48 (s, 3H), 0.98 (t, J=7.04 Hz, 3H). LCMS (ES+) m/z 432 (M+1).

5-(Ethoxymethyl)-N-[(1-methyl-1H-imidazol-5-yl)methyl]-1-[5-methyl-4-(3-thienyl)pyrimidin-2-yl]-1H-pyrazole-4-carboxamide (112). $^1$H NMR 400 MHz (CDCl$_3$) δ: 8.68 (s, 1H), 8.22 (s, 1H), 7.97 (dd, J=2.74, 1.17 Hz, 1H), 7.95 (br t, J=5.08 Hz, 1H), 7.70 (dd, J=5.08, 1.17 Hz, 1H), 7.46 (dd, J=5.08, 2.74 Hz, 1H), 7.45 (s, 1H), 7.04 (s, 1H), 5.16 (s, 2H), 4.65 (d, J=5.08 Hz, 2H), 3.68 (s, 3H), 3.46 (q, J=7.04 Hz, 2H), 2.58 (s, 3H), 1.02 (t, J=7.04 Hz, 3H). LCMS (ES+) m/z 438 (M+1).

5-Butyl-N-[(2-methylimidazo[1,2-a]pyridin-3-yl)methyl]-1-(5-methyl-4-pyrrolidin-1-ylpyrimidin-2-yl)-1H-pyrazole-4-carboxamide (113). $^1$H NMR 400 MHz (CDCl$_3$) δ: 8.28 (d, J=6.84 Hz, 1H), 7.97 (s, 1H), 7.83 (s, 1H), 7.52 (d, J=8.79 Hz, 1H), 7.23 (dd, J=8.79, 7.81 Hz, 1H), 6.84 (d, J=7.81, 6.84 Hz, 1H), 6.36 (br s, 1H), 4.93 (d, J=5.37 Hz, 2H), 3.80-3.73 (m, 4H), 3.59-3.53 (m, 2H), 2.45 (s, 3H), 2.40 (s, 3H), 2.00-1.94 (m, 4H), 1.65-1.56 (m, 2H), 1.40-1.30 (m, 2H), 0.88 (t, J=7.32 Hz, 3H). LCMS (ES+) m/z 473 (M+1).

5-Butyl-N-[(1,4-dimethyl-1H-imidazol-5-yl)methyl]-1-(5-methyl-4-pyrrolidin-1-ylpyrimidin-2-yl)-1H-pyrazole-4-carboxamide (114). $^1$H NMR 400 MHz (CDCl$_3$) δ: 7.98 (s, 1H), 7.81 (s, 1H), 7.35 (s, 1H), 6.29 (br s, 1H), 4.57 (d, J=4.88 Hz, 2H), 3.80-3.71 (m, 4H), 3.60 (s, 3H), 3.55-3.49 (m, 2H), 2.40 (s, 3H), 2.20 (s, 3H), 2.00-1.92 (m, 4H), 1.64-1.54 (m, 2H), 1.39-1.29 (m, 2H), 0.87 (t, J=7.32 Hz, 3H). LCMS (ES+) m/z 437 (M+1).

5-(2-Methoxyethyl)-N-[(1-methyl-1H-imidazol-5-yl)methyl]-1-[5-methyl-4-(2-thienyl)pyrimidin-2-yl]-1H-pyrazole-4-carboxamide (115). $^1$H NMR 400 MHz (CDCl$_3$) δ: 8.65 (s, 1H), 8.30 (br t, J=5.47 Hz, 1H), 8.11 (s, 1H), 7.77 (dd, J=3.91, 0.78 Hz, 1H), 7.62 (dd, J=5.08, 0.78 Hz, 1H), 7.50 (s, 1H), 7.24 (dd, J=5.08, 3.91 Hz, 1H), 7.04 (s, 1H), 4.61 (d, J=5.27 Hz, 2H), 3.89 (t, J=5.27 Hz, 2H), 3.72 (t, J=5.47 Hz, 2H), 3.70 (s, 3H), 3.13 (s, 3H), 2.61 (s, 3H). LCMS (ES+) m/z 438 (M+1).

1-[5-Chloro-4-(2-thienyl)pyrimidin-2-yl]-N-[(1,4-dimethyl-1H-imidazol-5-yl)methyl]-5-(ethoxymethyl)-1H-pyrazole-4-carboxamide (116). $^1$H NMR 400 MHz (CDCl$_3$) δ: 8.80 (s, 1H), 8.42 (dd, J=3.90, 1.17 Hz, 1H), 8.24 (s, 1H), 7.90 (br t, J=5.08 Hz, 1H), 7.70 (dd, J=5.08, 1.17 Hz, 1H), 7.37 (s, 1H), 7.26 (dd, J=5.08, 3.90 Hz, 1H), 5.23 (s, 2H), 4.60 (d, J=5.08 Hz, 2H), 3.64 (s, 3H), 3.49 (q, J=7.04 Hz, 2H), 2.27 (s, 3H), 1.00 (t, J=7.04 Hz, 3H). LCMS (ES+) m/z 472 (M+1).

1-[4-({[tert-butyl(diphenyl)silyl]oxy}methyl)-1-methyl-1H-imidazol-5-yl]methanamine (117). Methyl 4-(hydroxymethyl)-1H-imidazole-5-carboxylate was dissolved in N,N-dimethylformamide, to this solution, tert-butyl(diphenyl)silyl chloride (1.94 g), imidazole (1.44 g), and catalytic amount of DMAP were added at room temperature. After stirring for 2 hours, the reaction mixture was treated with water and filtered. The residue was washed with water to give methyl 4-({[tert-butyl(diphenyl)silyl]oxy}methyl)-1H-imidazole-5-carboxylate (2.68 g). This compound (2.68 g) was dissolved in N,N-dimethylformamide, to this solution, methyl iodide (478 uL) and potassium carbonate (1.33 g) were added at room temperature. After stirring for overnight, the reaction mixture was treated with water and extracted with ethyl acetate (×3). The combined organic layers were washed with water (×3), and then dried over sodium sulfate, evaporated under reduced pressure. The residue was purified by silica gel column chromatography to give methyl 4-({[tert-butyl(diphenyl)silyl]oxy}methyl)-1H-imidazole-5-carboxylate (1.3 g). This compound (1 g) was dissolved in tetrahydrofuran and cooled by ice water. To this solution, lithium aluminum hydride (185 mg) was slowly added portionwise and stirred for further 10 min. To this solution, water (0.2 mL), 5N NaOH aq. (0.2 mL), water (0.2 mL×3), and sodium sulfate were added subsequently, then the residue was filtered and evaporated under reduced pressure to give [4-({[tert-butyl(diphenyl)silyl]oxy}methyl)-1-methyl-1H-imidazol-5-yl]methanol (807 mg). This compound (807 mg) was dissolved in N,N-dimethylformamide. To the solution, diphenylphosphoryl azide (770 mg) and 1,8-Diazabicyclo[5.4.0]undec-7-ene (425 mg) were added, then heated to 80 degrees. After stirring for 2 hours, the reaction mixture was evaporated, and then treated with water and extracted with ethyl acetate (×3). The combined organic layers was washed with brine, dried over sodium sulfate, evaporated under reduced pressure. The residue was purified by silica gel column chromatography to give 5-(azidomethyl)-4-({[tert-butyl(diphenyl)silyl]oxy}methyl)-1-methyl-1H-imidazole (454 mg). This compound (454 mg) was dissolved in Ethyl acetate and methyl alcohol. To this solution, 10% palladium-carbon (100 mg) was added and stirred for 1 hour under H$_2$ atmosphere. The reaction mixture was filtered and the filtrate was evaporated to give 1-[4-({[tert-butyl(diphenyl)silyl]oxy}methyl)-1-methyl-1H-imidazol-5-yl]methanamine (410 mg). $^1$H NMR 400 MHz (CDCl$_3$): 7.73-7.69 (m, 4H), 7.45-7.35 (m, 6H), 7.33 (s, 1H), 4.70 (s, 2H), 3.74 (s, 2H), 3.63 (s, 3H), 1.06 (s, 9H). LCMS (ES+) m/z 380 (M+1).

5-(Ethoxymethyl)-1-(5-methyl-4-(thiophen-2-yl)pyrimidin-2-yl)-1H-pyrazole-4-carboxylic acid (118). $^1$H NMR 400 MHz (CDCl$_3$) δ: 8.68 (s, 1H), 8.28 (s, 1H), 7.85 (dd, J=3.91, 0.78 Hz, 1H), 7.64 (dd, J=5.08, 0.78 Hz, 1H), 7.25 (dd, J=5.08, 3.91 Hz, 1H), 5.49 (s, 2H), 3.68 (q, J=7.04 Hz, 2H), 2.65 (s, 3H), 1.99 (t, J=7.04 Hz, 3H).

5-Butyl-N-(imidazo[1,2-a]pyridin-3-ylmethyl)-1-(5-methyl-4-pyrrolidin-1-ylpyrimidin-2-yl)-1H-pyrazole-4-carboxamide (119). $^1$H NMR 400 MHz (CDCl$_3$) δ: 8.33 (d, J=6.65 Hz, 1H), 7.99 (s, 1H), 7.75 (s, 1H), 7.62 (d, J=8.99 Hz, 1H), 7.58 (s, 1H), 7.21 (dd, J=8.99, 6.65 Hz, 1H), 6.83 (t, J=6.65 Hz, 1H), 6.10 (br t, J=5.87 Hz, 1H), 4.99 (d, J=5.87 Hz, 2H), 3.81-3.72 (m, 4H), 3.60-3.51 (m, 2H), 2.40 (s, 3H), 2.03-1.91 (m, 4H), 1.66-1.55 (m, 2H), 1.40-1.28 (m, 2H), 0.87 (t, J=7.04 Hz, 3H). LCMS (ES+) m/z 459 (M+1).

5-Butyl-N-[(2-methylimidazo[1,2-a]pyridin-3-yl)methyl]-1-[5-methyl-4-(2-thienyl)pyrimidin-2-yl]-1H-pyrazole-4-carboxamide (120). $^1$H NMR 400 MHz (CDCl$_3$) δ: 8.66 (s, 1H), 8.23 (d, J=7.04 Hz, 1H), 7.85 (s, 1H), 7.83 (d, J=3.52 Hz, 1H), 7.64 (d, J=4.69 Hz, 1H), 7.54 (d, J=8.99 Hz, 1H), 7.25 (dd, J=4.69, 3.52 Hz, 1H), 7.19 (dd, J=8.99, 7.04 Hz, 1H), 6.81 (t, J=7.04 Hz, 1H), 5.99 (br t, J=5.47 Hz, 1H), 4.98 (d, J=5.47 Hz, 2H), 3.71-3.64 (m, 2H), 2.64 (s, 3H), 2.50 (s, 3H), 1.72-1.60 (m, 2H), 1.45-1.34 (m, 2H), 0.87 (t, J=7.43 Hz, 3H). LCMS (ES+) m/z 486 (M+1).

Methyl 3-{[({5-butyl-1-[5-chloro-4-(cyclopropylamino)pyrimidin-2-yl]-1H-pyrazol-4-yl}carbonyl)amino]methyl}imidazo[1,2-a]pyridine-7-carboxylate (121). Methyl 2-aminoisonicotinate (5.64 g) and chloroacetaldehyde (6.1M, 12.2 mL) were dissolved in EtOH. To this solution, sodium hydrogen carbonate (6.23 g) was added and heated to 80 degrees. After stirring for 2 hours, the reaction mixture was evaporated and treated with water, extracted ethyl acetate, washed with brine, dried over sodium sulfate, then evaporated under reduced pressure to give methyl imidazo[1,2-a]pyridine-7-carboxylate (4.42 g). This compound (4.42 g) was dissolved in acetic acid. To this solution, formaldehyde (37%, 13.2 mL) and sodium acetate (7.82 g) were added and heated to 105 degrees. After stirring for 3 hours, the reaction mixture was treated with water, and NaOH aq., then the precipitate was filtered off. The filtrate was extracted with EtOAc-n-BuOH (×2), dried over sodium sulfate, then evaporated under reduced pressure to give methyl 3-(hydroxymethyl)imidazo[1,2-a]pyridine-7-carboxylate (2.22 g). This compound (2.22 g) was dissolved in N,N-dimethylformamide, to the solution, diphenylphosphoryl azide (6.14 g) and 1,8-Diazabicyclo[5.4.0]undec-7-ene (3.40 g) were added. After stirring for 2 hours at room temperature, the reaction mixture was evaporated, and then treated with water and extracted with ethyl acetate (×3). The combined organic layers were washed with brine, dried over sodium sulfate, evaporated under reduced pressure. The residue was purified by silica gel column chromatography to give methyl 3-(azidomethyl)imidazo[1,2-a]pyridine-7-carboxylate (1.91 g). This compound (1.91 g) was dissolved in THF (30 mL) and water (3 mL). To this solution, triphenylphosphine (4.33 g) was added and heated to 70 degrees. After stirring for 1.5 hours, the reaction mixture was evaporated and treated with 1N HCl. The water phase was washed with EtOAc (×2) to give methyl 3-(aminomethyl)imidazo[1,2-a]pyridine-7-carboxylate 2 hydrochloride (1.98 g).

Compound 121 was prepared by similar procedure in Example 35 with the exception of substituting methyl 3-(aminomethyl)imidazo[1,2-a]pyridine-7-carboxylate and 5-butyl-1-[5-chloro-4-(cyclopropylamino)pyrimidin-2-yl]-1H-pyrazole-4-carboxylic acid. $^1$H NMR 400 MHz (CD$_3$OD) δ: 8.63 (dd, J=7.43, 0.78 Hz, 1H), 8.26 (dd, J=1.56, 0.78 Hz, 1H), 8.23 (s, 1H), 7.97 (s, 1H), 7.79 (s, 1H), 7.51 (dd, J=7.43, 1.56 Hz, 1H), 4.95 (s, 2H), 3.96 (s, 3H), 3.63-3.57 (m, 2H), 2.95-2.88 (m, 1H), 1.61-1.51 (m, 2H), 1.32-1.22 (m, 2H), 0.91-0.78 (m, 5H), 0.73-0.66 (m, 2H). LCMS (ES+) m/z 523 (M+1).

5-Butyl-1-[5-chloro-4-(cyclopropylamino)pyrimidin-2-yl]-N-(imidazo[1,2-a]pyridin-3-ylmethyl)-1H-pyrazole-4-carboxamide (122). $^1$H NMR 400 MHz (CD$_3$OD) δ: 8.53 (d, J=6.84 Hz, 1H), 8.23 (s, 1H), 7.98 (s, 1H), 7.61 (s, 1H), 7.58 (d, J=9.28 Hz, 1H), 7.36 (dd, J=9.28, 6.84 Hz, 1H), 7.00 (t, J=6.84 Hz, 1H), 4.93 (s, 2H), 3.65-3.57 (m, 2H), 2.95-2.89 (m, 1H), 1.62-1.52 (m, 2H), 1.32-1.21 (m, 2H), 0.89-0.79 (m, 5H), 0.73-0.67 (m, 2H). LCMS (ES+) m/z 465 (M+1).

2-(5-{[({5-Butyl-1-[5-methyl-4-(2-thienyl)pyrimidin-2-yl]-1H-pyrazol-4-yl}carbonyl)amino]methyl}-4-methyl-1H-imidazol-1-yl)-2-methylpropanoic acid (123). $^1$H NMR 400 MHz (DMSO-d$_6$) δ: 9.15 (s, 1H), 8.85 (s, 1H), 8.47 (br t, J=4.88 Hz, 1H), 8.14 (s, 1H), 7.99-7.89 (m, 2H), 7.33 (dd, J=4.88, 3.91 Hz, 1H), 4.43 (d, J=4.88 Hz, 2H), 3.44-3.30 (m, 2H), 2.62 (s, 3H), 2.33 (s, 3H), 1.88 (s, 6H), 1.53-1.42 (m, 2H), 1.27-1.16 (m, 2H), 0.76 (t, J=7.32 Hz, 3H). LCMS (ES+) m/z 522 (M+1).

N-{[4-(Hydroxymethyl)-1-methyl-1H-imidazol-5-yl]methyl}-5-(methoxymethyl)-1-[5-methyl-4-(2-thienyl)pyrimidin-2-yl]-1H-pyrazole-4-carboxamide (124). $^1$H NMR 400 MHz (CDCl$_3$) δ: 8.65 (s, 1H), 8.16 (s, 1H), 8.03 (br t, J=5.47 Hz, 1H), 7.82 (dd, J=3.91, 1.17 Hz, 1H), 7.63 (dd, J=5.08, 1.17 Hz, 1H), 7.39 (s, 1H), 7.24 (dd, J=5.08, 3.91 Hz, 1H), 5.31 (s, 2H), 4.69 (s, 2H), 4.66 (d, J=5.47 Hz, 2H), 3.69 (s, 3H), 3.33 (s, 3H), 2.62 (s, 3H). LCMS (ES+) m/z 454 (M+1).

N-{[4-(Hydroxymethyl)-1-methyl-1H-imidazol-5-yl]methyl}-5-(methoxymethyl)-1-(5-methyl-4-piperidin-1-ylpyrimidin-2-yl)-1H-pyrazole-4-carboxamide (125). $^1$H NMR 400 MHz (CDCl$_3$) δ: 8.13 (s, 1H), 8.10 (s, 1H), 7.94 (br t, J=5.47 Hz, 1H), 7.38 (s, 1H), 5.15 (s, 2H), 4.69 (s, 2H), 4.64 (d, J=5.47 Hz, 2H), 3.68 (s, 3H), 3.56-3.48 (m, 4H), 3.29 (s, 3H), 2.27 (s, 3H), 1.75-1.62 (m, 6H). LCMS (ES+) m/z 455 (M+1).

N-{[4-(Hydroxymethyl)-1-methyl-1H-imidazol-5-yl]methyl}-1-(5-methyl-4-morpholin-4-ylpyrimidin-2-yl)-5-propyl-1H-pyrazole-4-carboxamide (126). $^1$H NMR 400 MHz (CDCl$_3$) δ: 8.22 (s, 1H), 7.83 (s, 1H), 7.35 (s, 1H), 7.00 (br s, 1H), 4.70-4.60 (m, 4H), 3.87-3.78 (m, 4H), 3.65 (s, 3H), 3.59-3.50 (m, 4H), 3.49-3.40 (m, 2H), 2.28 (s, 3H), 1.70-1.58 (m, 2H), 0.93 (t, J=7.43 Hz, 3H). LCMS (ES+) m/z 455 (M+1).

1-[4-(3-Furyl)-5-methylpyrimidin-2-yl]-N-[{4-(hydroxymethyl)-1-methyl-1H-imidazol-5-yl]methyl}-5-(methoxymethyl)-1H-pyrazole-4-carboxamide (127). $^1$H NMR 400 MHz (CDCl$_3$) δ: 8.64 (s, 1H), 8.14 (s, 1H), 8.10 (dd, J=1.56, 0.78 Hz, 1H), 7.90 (br t, J=5.47 Hz, 1H), 7.58 (dd, J=1.96, 1.56 Hz, 1H), 7.38 (s, 1H), 7.11 (dd, J=1.96, 0.78 Hz, 1H), 5.22 (s, 2H), 4.69 (s, 2H), 4.66 (d, J=5.47 Hz, 2H), 3.69 (s, 3H), 3.31 (s, 3H), 2.51 (s, 3H). LCMS (ES+) m/z 438 (M+1).

5-(2-Methoxyethyl)-N-[(1-methyl-1H-imidazol-5-yl)methyl]-1-[5-methyl-4-(3,3,4,4-tetrafluoropyrrolidin-1-yl)pyrimidin-2-yl]-1H-pyrazole-4-carboxamide (128). $^1$H NMR 400 MHz (CDCl$_3$) δ: 8.15 (s, 1H), 8.03 (s, 1H), 7.88 (br t, J=5.08 Hz, 1H), 7.44 (s, 1H), 7.02 (s, 1H), 4.60 (d, J=5.08 Hz, 2H), 4.32-4.20 (m, 4H), 3.76 (t, J=5.47 Hz, 2H), 3.67 (s, 3H), 3.55 (t, J=5.47 Hz, 2H), 3.14 (s, 3H), 2.40 (s, 3H). LCMS (ES+) m/z 497 (M+1).

5-Butyl-1-[5-chloro-4-(cyclopropylamino)pyrimidin-2-yl]-N-[(1-methyl-1H-imidazol-5-yl)methyl]-1H-pyrazole-4-carboxamide (129). $^1$H NMR 400 MHz (CD$_3$OD) δ: 8.23 (s, 1H), 8.01 (s, 1H), 7.59 (s, 1H), 6.95 (s, 1H), 4.56 (s, 2H), 3.72 (s, 3H), 3.59 (t, J=7.32 Hz, 2H), 2.96-2.87 (m, 1H), 1.63-1.51 (m, 2H), 1.35-1.24 (m, 2H), 0.89-0.79 (m, 5H), 0.73-0.65 (m, 2H). LCMS (ES+) m/z 429 (M+1).

1-[5-Chloro-4-(cyclopropylamino)pyrimidin-2-yl]-5-(2-methoxyethyl)-N-[(1-methyl-1H-imidazol-5-yl)methyl]-1H-pyrazole-4-carboxamide (130). $^1$H NMR 400 MHz (CDCl$_3$) δ: 8.25 (s, 1H), 8.09 (br d, J=5.08 Hz, 1H), 8.06 (s, 1H), 7.44 (s, 1H), 7.02 (s, 1H), 5.41 (br s, 1H), 4.60 (d, J=5.08 Hz, 2H), 3.81 (t, J=5.47 Hz, 2H), 3.69 (t, J=5.47 Hz, 2H), 3.67 (s, 3H), 3.11 (s, 3H), 2.87-2.80 (m, 1H), 0.96-0.88 (m, 2H), 0.71-0.65 (m, 2H). LCMS (ES+) m/z 431 (M+1).

1-[4-(3-Furyl)-5-methylpyrimidin-2-yl]-N-{[4-(hydroxymethyl)-1-methyl-1H-imidazol-5-yl]methyl}-5-propyl-1H-pyrazole-4-carboxamide (131). $^1$H NMR 400 MHz (CDCl$_3$) δ:8.62 (s, 1H), 8.08 (dd, J=1.17, 0.78 Hz, 1H), 7.88 (s, 1H), 7.57 (dd, J=1.96, 1.17 Hz, 1H), 7.37 (s, 1H), 7.09 (dd, J=1.96, 0.78 Hz, 1H), 6.98 (br t, J=5.47 Hz, 1H), 4.68 (s, 2H), 4.67 (d, J=5.47 Hz, 2H), 3.67 (s, 3H), 3.56-3.48 (m, 2H), 2.50 (s, 3H), 1.76-1.64 (m, 2H), 0.94 (t, J=7.43 Hz, 3H). LCMS (ES+) m/z 436 (M+1).

1-[5-Ethyl-4-(2-thienyl)pyrimidin-2-yl]-N-{[4-(hydroxymethyl)-1-methyl-1H-imidazol-5-yl]methyl}-5-(methoxymethyl)-1H-pyrazole-4-carboxamide (132). $^1$H NMR 400 MHz (CDCl$_3$) δ: 8.70 (s, 1H), 8.17 (s, 1H), 8.01 (br t, J=5.47 Hz, 1H), 7.78 (dd, J=3.91, 0.78 Hz, 1H), 7.62 (dd, J=5.08, 0.78 Hz, 1H), 7.40 (s, 1H), 7.23 (dd, J=5.08, 3.91 Hz, 1H), 5.30 (s, 2H), 4.70 (s, 2H), 4.66 (d, J=5.47 Hz, 2H), 3.70 (s, 3H), 3.33 (s, 3H), 3.03 (q, J=7.43 Hz, 2H), 1.42 (t, J=7.43 Hz, 3H). LCMS (ES+) m/z 468 (M+1).

7.43. Example 133

The following example describes how compounds can be evaluated in vivo in glucose-challenged animal models.

Art-recognized animal models of diabetes, such as type 2 diabetes, include diet-induced obese C57BL/6 ("B6") mice and ob/ob mice. See, e.g., Breyer et al., *J. Am. Soc. Nephrol.* 16:27-45 (2005) and references cited therein.

Rats (aged 5-20) weeks or mice (aged 6-20 weeks) are fasted overnight beginning at 4 pm. Between 9 and 10 am, glucose levels are determined with a glucometer using whole blood samples removed from the tail. The animals are placed into control and treatment groups having similar averages of glucose levels and body weights or similar averages of body weights (B6 mice). Animals are pre-dosed with vehicle (control group) or test article (5-10 mL/kg, p.o., s.c. or i.p.) and then challenged with glucose (1 g/kg, p.o. or i.p.). Blood samples are then collected from the tail and assay for glucose and insulin levels.

FIG. 1 provides results from glucose-challenged animal models of diabetes demonstrating the increases in circulating insulin levels in animals treated with 1-(5-methyl-4-(thiophen-2-yl)pyrimidin-2-yl)-5-propyl-N-(1-(pyridin-4-yl)ethyl)-1H-pyrazole-4-carboxamide relative to control animals, according to the experimental protocol described above.

7.44. Example 134

The following example describes an islet insulin secretion assay for evaluating compounds provided herein.

The pancreatic islets of Langerhans are isolated from 12-14 week old male C57BL/6 mice by collagenase digestion and histopaque fractionation as described in Gotoh et al. (1987) *Transplantation* 43:725-730. The isolated islets are cultured in RPMI 1640 medium plus 10% fetal bovine serum for 72 hours. For the assay, the islets are hand picked and separated into 8 treatment groups, each group containing 3 replicates of 5 islets. The islets are acclimated in 1.0 mL of Krebs-Ringer bicarbonate HEPES (KRBH) buffer plus 1.0 mM glucose, 0.625% (w/v) human serum albumin (HSA) for 1 hour. The islets are then transferred to 1.0 mL of KRBH assay buffer plus 16.7 mM glucose, 0.625% (w/v) HSA, and various concentrations of test compound. After one hour of treatment, to assess insulin secretion, supernatants are collected and concentrations of insulin in the supernatants are determined by an insulin ELISA method.

Results for exemplary compound 1-(5-methyl-4-(thiophen-2-yl)pyrimidin-2-yl)-5-propyl-N-(1-(pyridin-4-yl)ethyl)-1H-pyrazole-4-carboxamide are provided in FIG. 2.

7.45. Example 135

The results presented below exemplify that administration of the compounds as provided herein to an art-recognized animal model of human diabetes can lead to increased circulating insulin concentrations in the animal model.

Male ob/ob mice were weighed and bled from tail vein, and blood glucose levels were determined with a glucometer. Animals were placed into control and treatment groups having similar averages of glucose levels and body weights. In the morning of the following day, animals were dosed with vehicle (control group) or test article (5 ml/kg, p.o.). Blood samples were collected just before and 10 minutes after dosing, and the samples were assayed for insulin and glucose concentrations.

Table 1 provides exemplary data showing the increase of circulating insulin concentrations (expressed as ng/ml) in treated mice relative to control group at 10 minutes after dosing the treated mice. Concentrations of the exemplary compound tested in the mice are provided in the righthand column.

TABLE 1

Increases in Insulin Concentrations In Treated ob/ob Mice

| Example | Increase in Insulin (ng/ml) | Dose (mg/kg) |
|---|---|---|
| 1-(5-Methyl-4-(thiophen-2-yl)pyrimidin-2-yl)-5-propyl-N-(1-(pyridin-4-yl)ethyl)-1H-pyrazole-4-carboxamide | 3.9 | 10 |
| 5-Butyl-1-(5-methyl-4-(thiophen-2-yl)pyrimidin-2-yl)-N-((pyridin-4-yl)methyl)-1H-pyrazole-4-carboxamide | 4.1 | 30 |
| 5-Butyl-1-(5-methyl-4-(thiophen-2-yl)pyrimidin-2-yl)-N-(2-(pyridin-4-yl)propan-2-yl)-1H-pyrazole-4-carboxamide | 4.6 | 30 |
| N-((1-Methyl-1H-imidazol-5-yl)methyl)-1-(5-methyl-4-(thiophen-2-yl)pyrimidin-2-yl)-5-propyl-1H-pyrazole-4-carboxamide | 28.5 | 30 |
| 5-Butyl-1-(5-methyl-4-(thiophen-2-yl)pyrimidin-2-yl)-N-(1-(pyridin-4-yl)propyl)-1H-pyrazole-4-carboxamide | 3.1 | 10 |
| 5-(Ethoxymethyl)-1-(5-methyl-4-(thiophen-2-yl)pyrimidin-2-yl)-N-(1-(pyridin-4-yl)ethyl)-1H-pyrazole-4-carboxamide | 6.7 | 10 |
| N-(2-(1-Methyl-1H-imidazol-5-yl)ethyl)-1-(5-methyl-4-(thiophen-2-yl)pyrimidin-2-yl)-5-propyl-1H-pyrazole-4-carboxamide | 9.5 | 10 |
| N-(5,6,7,8-Tetrahydroisoquinolin-5-yl)-1-(5-methyl-4-(thiophen-2-yl)pyrimidin-2-yl)-5-propyl-1H-pyrazole-4-carboxamide | 8.8 | 10 |
| N-(1H-Benzo[d]imidazol-7-yl)-5-butyl-1-(5-methyl-4-(thiophen-2-yl)pyrimidin-2-yl)-1H-pyrazole-4-carboxamide | 0.9 | 10 |
| N-(2-(1H-Imidazol-1-yl)ethyl)-5-butyl-1-(5-methyl-4-(thiophen-2-yl)pyrimidin-2-yl)-1H-pyrazole-4-carboxamide | 2.9 | 10 |
| 5-Butyl-N-(imidazo[1,2-a]pyridin-3-ylmethyl)-1-[5-methyl-4-(2-thienyl)pyrimidin-2-yl]-1H-pyrazole-4-carboxamide | 8.5 | 10 |
| N-(Imidazo[1,2-a]pyridin-3-ylmethyl)-5-(methoxymethyl)-1-[5-methyl-4-(2-thienyl)pyrimidin-2-yl]-1H-pyrazole-4-carboxamide | 4.4 | 10 |
| 5-Butyl-N-(1-methyl-1H-benzo[d]imidazol-7-yl)-1-(5-methyl-4-(thiophen-2-yl)pyrimidin-2-yl)-1H-pyrazole-4-carboxamide | 4.3 | 10 |
| 5-Butyl-N-(1-(1-methyl-1H-imidazol-5-yl)ethyl)-1-(5-methyl-4-(thiophen-2-yl)pyrimidin-2-yl)-1H-pyrazole-4-carboxamide | 6.4 | 10 |
| Methyl 2-(5-((5-butyl-1-(5-methyl-4-(thiophen-2-yl)pyrimidin-2-yl)-1H-pyrazole-4-carboxamido)methyl)-1H-imidazol-1-yl)acetate | 4.3 | 10 |
| 2-(5-((5-Butyl-1-(5-methyl-4-(thiophen-2-yl)pyrimidin-2-yl)-1H-pyrazole-4-carboxamido)methyl)-1H-imidazol-1-yl)acetic acid | 3.8 | 10 |
| 5-Butyl-N-(2-hydroxy-1-(1-methyl-1H-imidazol-5-yl)ethyl)-1-(5-methyl-4-(thiophen-2-yl)pyrimidin-2-yl)-1H-pyrazole-4-carboxamide | 5.2 | 10 |
| 5-Butyl-N-(isoquinolin-5-yl)-1-(5-methyl-4-(thiophen-2-yl)pyrimidin-2-yl)-1H-pyrazole-4-carboxamide | 7.7 | 10 |
| 5-Butyl-N-(2-hydroxy-1-(pyridin-4-yl)ethyl)-1-(5-methyl-4-(thiophen-2-yl)pyrimidin-2-yl)-1H-pyrazole-4-carboxamide | 4.3 | 10 |
| 5-Butyl-N-(6,7-dihydro-5H-pyrrolo[1,2-e]imidazol-7-yl)-1-(5-methyl-4-(thiophen-2-yl)pyrimidin-2-yl)-1H-pyrazole-4-carboxamide | 2.2 | 10 |
| N-(2-Hydroxy-1-(1-methyl-1H-imidazol-5-yl)ethyl)-1-(5-methyl-4-(thiophen-2-yl)pyrimidin-2-yl)-5-propyl-1H-pyrazole-4-carboxamide | 3.1 | 10 |
| 5-Butyl-1-(5-methyl-4-(thiophen-2-yl)pyrimidin-2-yl)-N-(5,6,7,8-tetrahydroimidazo[1,5-a]pyridin-8-yl)-1H-pyrazole-4-carboxamide | 1.4 | 3 |
| 5-Butyl-N-(isoquinolin-5-yl)-1-(5-methyl-4-(thiophen-2-yl)pyrimidin-2-yl)-1H-pyrazole-4-carboxamide | 3.4 | 10 |
| 1-[5-Bromo-4-(cyclobutylamino)pyrimidin-2-yl]-5-butyl-N-(imidazo[1,2-a]pyridin-3-ylmethyl)-1H-pyrazole-4-carboxamide | 7.2 | 10 |
| 2-(5-((5-Butyl-1-(5-methyl-4-(thiophen-2-yl)pyrimidin-2-yl)-1H-pyrazole-4-carboxamido)methyl)-4-methyl-1H-imidazol-1-yl)acetic acid | 3.9 | 10 |
| N-((1-(2-Amino-2-oxoethyl)-4-methyl-1H-imidazol-5-yl)methyl)-5-butyl-1-(5-methyl-4-(thiophen-2-yl)pyrimidin-2-yl)-1H-pyrazole-4-carboxamide | 4 | 10 |
| N-((1-(((Methylcarbamoyl)methyl)-4-methyl-1H-imidazol-5-yl)methyl)-5-butyl-1-(5-methyl-4-(thiophen-2-yl)pyrimidin-2-yl)-1H-pyrazole-4-carboxamide | 9 | 10 |
| 5-Butyl-N-((1-(2-(dimethylamino)-2-oxoethyl)-4-methyl-1H-imidazol-5-yl)methyl)-1-(5-methyl-4-(thiophen-2-yl)pyrimidin-2-yl)-1H-pyrazole-4-carboxamide | 4.7 | 10 |
| 2-(5-Butyl-1-(5-methyl-4-(thiophen-2-yl)pyrimidin-2-yl)-1H-pyrazole-4-carboxamido)-3-(1H-imidazol-4-yl)propanoicacid | 4.5 | 10 |

TABLE 1-continued

Increases in Insulin Concentrations In Treated ob/ob Mice

| Example | Increase in Insulin (ng/ml) | Dose (mg/kg) |
|---|---|---|
| Methyl 1-(2-(5-butyl-N-methyl-1-(5-methyl-4-(thiophen-2-yl)pyrimidin-2-yl)-1H-pyrazole-4-carboxamido)ethyl)-1H-imidazole-5-carboxylate | 6.6 | 10 |
| 1-(2-(5-Butyl-1-(5-methyl-4-(thiophen-2-yl)pyrimidin-2-yl)-1H-pyrazole-4-carboxamido)ethyl)-1H-imidazole-5-carboxylic acid | 6.1 | 10 |
| 2-(5-((1-(5-bromo-4-(cyclobutylamino)pyrimidin-2-yl)-5-butyl-1H-pyrazole-4-carboxamido)methyl)-4-methyl-1H-imidazol-1-yl)acetic acid | 1.7 | 10 |

Over 100 exemplary compounds as provided herein were tested in an in vitro assay relevant to insulin secretion and found to have activity. See U.S. Provisional App. No. 60/851,083, filed Oct. 10, 2006, Section 6.43 including Table 1, which is incorporated by reference herein in its entirety for all purposes.

7.46. Example 136

The following example describes the glucose lowering effect of compounds observed in vivo.

Male C57B6 mice were placed into control and treatment groups having similar averages of body weights. Then, animals were dosed with vehicle (control group) or test article (5 ml/kg, p.o.). Thirty minutes after dosing, glucose (3 g/kg) was orally administered in each animal. Blood samples were collected just before, 20 minutes and 50 minutes after glucose challenge and glucose concentrations in the samples was assessed. The values in Table 2 represent the observed % AUC reduction of blood glucose in the treated animals relative to the control group.

TABLE 2

Reductions in Glucose Levels In Treated C57B6 Mice

| Example | % AUC reduction in glucose levels |
|---|---|
| 2-(5-((5-Butyl-1-(5-methyl-4-(thiophen-2-yl)pyrimidin-2-yl)-1H-pyrazole-4-carboxamido)methyl)-4-methyl-1H-imidazol-1-yl)acetic acid | 19 |
| 2-(5-{[({5-Butyl-1-[5-methyl-4-(2-thienyl)pyrimidin-2-yl]-1H-pyrazol-4-yl}carbonyl)amino]methyl}-4-methyl-1H-imidazol-1-yl)-2-methylpropanoic acid | 15 |
| 5-Butyl-1-[5-chloro-4-(cyclopropylamino)pyrimidin-2-yl]-N-[(1-methyl-1H-imidazol-5-yl)methyl]-1H-pyrazole-4-carboxamide | 7 |
| 5-Butyl-1-[5-chloro-4-(cyclopropylamino)pyrimidin-2-yl]-N-(imidazo[1,2-a]pyridin-3-ylmethyl)-1H-pyrazole-4-carboxamide | 32 |
| Methyl 3-{[({5-butyl-1-[5-chloro-4-(cyclopropylamino)pyrimidin-2-yl]-1H-pyrazol-4-yl}carbonyl)amino]methyl}imidazo[1,2-a]pyridine-7-carboxylate | 24 |
| 5-Butyl-N-[(2-methylimidazo[1,2-a]pyridin-3-yl)methyl]-1-[5-methyl-4-(2-thienyl)pyrimidin-2-yl]-1H-pyrazole-4-carboxamide | 35 |
| 5-Butyl-N-(imidazo[1,2-a]pyridin-3-ylmethyl)-1-(5-methyl-4-pyrrolidin-1-ylpyrimidin-2-yl)-1H-pyrazole-4-carboxamide | 34 |
| 5-(Ethoxymethyl)-N-((1-methyl-1H-imidazol-5-yl)methyl)-1-(5-methyl-4-(thiophen-2-yl)pyrimidin-2-yl)-1H-pyrazole-4-carboxamide | 16 |
| 5-(2-Methoxyethyl)-N-[(1-methyl-1H-imidazol-5-yl)methyl]-1-[5-methyl-4-(2-thienyl)pyrimidin-2-yl]-1H-pyrazole-4-carboxamide | 25 |
| 5-(Ethoxymethyl)-N-[(1-methyl-1H-imidazol-5-yl)methyl]-1-[5-methyl-4-(3-thienyl)pyrimidin-2-yl]-1H-pyrazole-4-carboxamide | 51 |
| 5-(Ethoxymethyl)-N-[(1-methyl-1H-imidazol-5-yl)methyl]-1-(5-methyl-4-phenylpyrimidin-2-yl)-1H-pyrazole-4-carboxamide | 35 |
| 5-(Ethoxymethyl)-N-((1-methyl-1H-imidazol-5-yl)methyl)-1-(5-methyl-4-(piperidin-1-yl)pyrimidin-2-yl)-1H-pyrazole-4-carboxamide | 42 |
| 5-(Ethoxymethyl)-N-[(1-methyl-1H-imidazol-5-yl)methyl]-1-[5-methyl-4-(3,3,4,4-tetrafluoropyrrolidin-1-yl)pyrimidin-2-yl]-1H-pyrazole-4-carboxamide | 11 |
| 5-(Ethoxymethyl)-N-[(1-methyl-1H-imidazol-5-yl)methyl]-1-(5-methyl-4-pyrrolidin-1-ylpyrimidin-2-yl)-1H-pyrazole-4-carboxamide | 18 |
| 1-[4-(Cyclohexylamino)-5-methylpyrimidin-2-yl]-5-(ethoxymethyl)-N-[(1-methyl-1H-imidazol-5-yl)methyl]-1H-pyrazole-4-carboxamide | 42 |
| 5-(Ethoxymethyl)-N-{[4-(hydroxymethyl)-1-methyl-1H-imidazol-5-yl]methyl}-1-[5-methyl-4-(2-thienyl)pyrimidin-2-yl]-1H-pyrazole-4-carboxamide | 35 |
| 5-(Ethoxymethyl)-N-[(1-methyl-1H-imidazol-5-yl)methyl]-1-[5-methyl-4-(1,3-thiazol-2-yl)pyrimidin-2-yl]-1H-pyrazole-4-carboxamide | 41 |
| 5-(Ethoxymethyl)-1-[4-(2-furyl)-5-methylpyrimidin-2-yl]-N-[(1-methyl-1H-imidazol-5-yl)methyl]-1H-pyrazole-4-carboxamide | 51 |
| 1-[4-(3,4-Dihydroisoquinolin-2(1H)-yl)-5-methylpyrimidin-2-yl]-5-(ethoxymethyl)-N-{[4-(hydroxymethyl)-1-methyl-1H-imidazol-5-yl]methyl}-1H-pyrazole-4-carboxamide | 63 |

TABLE 2-continued

Reductions in Glucose Levels In Treated C57B6 Mice

| Example | % AUC reduction in glucose levels |
|---|---|
| 1-[5-Chloro-4-(2-thienyl)pyrimidin-2-yl]-5-(ethoxymethyl)-N-{[4-(hydroxymethyl)-1-methyl-1H-imidazol-5-yl]methyl}-1H-pyrazole-4-carboxamide | 41 |
| N-{[4-(Hydroxymethyl)-1-methyl-1H-imidazol-5-yl]methyl}-1-[5-methyl-4-(2-thienyl)pyrimidin-2-yl]-5-propyl-1H-pyrazole-4-carboxamide | 35 |
| N-{[4-(Hydroxymethyl)-1-methyl-1H-imidazol-5-yl]methyl}-5-(methoxymethyl)-1-[5-methyl-4-(2-thienyl)pyrimidin-2-yl]-1H-pyrazole-4-carboxamide | 14 |
| N-{[4-(Hydroxymethyl)-1-methyl-1H-imidazol-5-yl]methyl}-5-(methoxymethyl)-1-(5-methyl-4-piperidin-1-ylpyrimidin-2-yl)-1H-pyrazole-4-carboxamide | 14 |
| N-{[4-(Hydroxymethyl)-1-methyl-1H-imidazol-5-yl]methyl}-1-(5-methyl-4-morpholin-4-ylpyrimidin-2-yl)-5-propyl-1H-pyrazole-4-carboxamide | 6 |
| 1-[4-(3-Furyl)-5-methylpyrimidin-2-yl]-N-{[4-(hydroxymethyl)-1-methyl-1H-imidazol-5-yl]methyl}-5-(methoxymethyl)-1H-pyrazole-4-carboxamide | 29 |
| 1-[4-(3-Furyl)-5-methylpyrimidin-2-yl]-N-{[4-(hydroxymethyl)-1-methyl-1H-imidazol-5-yl]methyl}-5-propyl-1H-pyrazole-4-carboxamide | 19 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having formula IV or V:

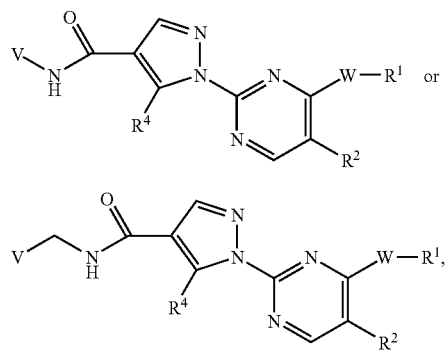

or a pharmaceutically acceptable salt thereof, wherein:
V is cyclo($C_3$-$C_7$)alkyl, heterocyclo($C_3$-$C_7$)alkyl, aryl, heteroaryl, aryl($C_1$-$C_4$)alkyl, or heteroaryl($C_1$-$C_4$)alkyl;
W is a single bond, ($C_1$-$C_5$)alkylene, ($C_2$-$C_5$)alkenylene, —O—, —S(O)$_k$—, —C(O)—, —NR$^6$— or —CH$_2$NR$^6$—;
R$^1$ is a substituted or unsubstituted member selected from furyl, isoxazolyl, oxazolyl, thiazolyl, pyrrolyl, thienyl, piperidinyl, cyclobutyl and cyclopentyl;
R$^2$ is halogen, ($C_1$-$C_6$)alkyl, —CN, halo($C_1$-$C_6$)alkyl, ($C_1$-$C_6$)alkoxy, halo($C_1$-$C_6$)alkoxy or ($C_2$-$C_6$)alkenyl; optionally, R$^2$ and W taken together form a 5- or 6-membered fused ring containing 0, 1, 2 or 3 heteroatoms selected from O, S, and N;
R$^4$ is ($C_1$-$C_8$)alkyl, hetero($C_2$-$C_8$)alkyl, cyclo($C_3$-$C_7$)alkyl, aryl, heteroaryl, aryl($C_1$-$C_4$)alkyl or heteroaryl($C_1$-$C_4$)alkyl;
R$^6$ is hydrogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —C(O)R', —CO$_2$R', —C(O)NR'R", —S(O)$_k$R' or —S(O)$_k$NR'R";
each R' and R" is independently hydrogen, ($C_1$-$C_6$)alkyl, cyclo($C_3$-$C_8$)alkyl, aryl or aryl($C_1$-$C_4$)alkyl; and
each subscript k is independently 0, 1 or 2.

2. The compound of claim 1, wherein R$^2$ is methyl, trifluoromethyl, chloro or fluoro.

3. The compound of claim 1, wherein R$^4$ is ($C_4$-$C_6$)alkyl, hetero($C_4$-$C_6$)alkyl or cyclo($C_4$-$C_6$)alkyl.

4. The compound of claim 1, wherein W is a single bond.

5. The compound of claim 4, wherein R$^1$ is thienyl.

6. The compound of claim 1, wherein R$^4$ is butyl or cyclopropylmethyl.

7. A pharmaceutical composition comprising a pharmaceutically acceptable carrier or excipient and a compound of claim 1.

8. A method for treating type 2 diabetes or symptom thereof, the method comprising administering to a subject in need thereof a therapeutically effective amount of a compound of claim 1.

9. The method of claim 8, wherein the compound is administered in combination with a second therapeutic agent.

10. The method of claim 9, wherein the second therapeutic agent is sulfonylurea, metformin, acarbose, nateglinide, pioglitazone or rosiglitazone.

11. The compound of claim 1, wherein V is a substituted or unsubstituted member selected from the group consisting of pyridine, imidazole, pyrimidine, 4-benzylpyridine, thiazole, benzene, triazole, pyrazole, and tetrazole.

12. The compound of claim 11, wherein V is substituted with one or more of ($C_1$-$C_8$)alkyl, halo($C_1$-$C_4$)alkyl, halo, cyclo($C_3$-$C_7$)alkyl, hetero($C_2$-$C_8$)alkyl, aryl, heteroaryl, aryl($C_1$-$C_4$)alkyl, hydroxyl, =O, —CN, —C(O)R', —CO$_2$R', —C(O)NR'R", —NR'R", —S(O)$_k$R' or —S(O)$_k$NR'R".

13. The compound of claim 1, wherein R$^1$ is substituted with one or more of ($C_1$-$C_8$)alkyl, halo($C_1$-$C_4$)alkyl, halo, cyclo($C_3$-$C_7$)alkyl, hetero($C_2$-$C_8$)alkyl, aryl, heteroaryl, aryl($C_1$-$C_4$)alkyl, hydroxyl, =O, —CN, —C(O)R', —CO$_2$R', —C(O)NR'R", —NR'R", —S(O)$_k$R' or —S(O)$_k$NR'R".

14. The compound of claim 1, wherein R⁴ is (C₃-C₆) alkoxyalkyl.

15. A compound selected from the group consisting of
- 5-(methoxymethyl)-1-(5-methyl-4-(thiophen-2-yl)pyrimidin-2-yl)-N-(pyridin-4-ylmethyl)-1H-pyrazole-4-carboxamide,
- N-((1-methyl-1H-imidazol-5-yl)methyl)-1-(5-methyl-4-(thiophen-2-yl)pyrimidin-2-yl)-5-phenyl-1H-pyrazole-4-carboxamide,
- 5-(2-chlorophenyl)-N-((1-methyl-1H-imidazol-5-yl)methyl)-1-(5-methyl-4-(thiophen-2-yl)pyrimidin-2-yl)-1H-pyrazole-4-carboxamide,
- N-((1-methyl-1H-imidazol-5-yl)methyl)-1-(5-methyl-4-(thiophen-2-yl)pyrimidin-2-yl)-5-propyl-1H-pyrazole-4-carboxamide,
- N-(2-(1H-imidazol-1-yl)ethyl)-5-butyl-1-(5-methyl-4-(thiophen-2-yl)pyrimidin-2-yl)-1H-pyrazole-4-carboxamide,
- 5-butyl-N-((1,2-dimethyl-1H-imidazol-5-yl)methyl)-1-(5-methyl-4-(thiophen-2-yl)pyrimidin-2-yl)-1H-pyrazole-4-carboxamide,
- 5-butyl-1-(5-methyl-4-(thiophen-2-yl)pyrimidin-2-yl)-N-((pyridin-4-yl)methyl)-1H-pyrazole-4-carboxamide, and
- 5-(ethoxymethyl)-N-((1-methyl-1H-imidazol-5-yl)methyl)-1-(5-methyl-4-(thiophen-2-yl)pyrimidin-2-yl)-1H-pyrazole-4-carboxamide, or a pharmaceutically acceptable salt thereof.

\* \* \* \* \*